US011446253B2

(12) United States Patent
Mitragotri et al.

(10) Patent No.: US 11,446,253 B2
(45) Date of Patent: Sep. 20, 2022

(54) IONIC LIQUIDS FOR INTERNAL DELIVERY

(71) Applicants: PRESIDENT AND FELLOWS OF HARVARD COLLEGE, Cambridge, MA (US); THE REGENTS OF THE UNIVERSITY OF CALIFORNIA, Oakland, CA (US)

(72) Inventors: Samir Mitragotri, Lexington, MA (US); Amrita Banerjee, Fargo, ND (US); Tyler Dwight Brown, Cambridge, MA (US); Kelly Ibsen, Brookline, MA (US); Christian Agatemor, Baltimore, MD (US)

(73) Assignees: PRESIDENT AND FELLOWS OF HARVARD COLLEGE, Cambridge, MA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/762,361

(22) PCT Filed: Nov. 16, 2018

(86) PCT No.: PCT/US2018/061532
§ 371 (c)(1),
(2) Date: May 7, 2020

(87) PCT Pub. No.: WO2019/099837
PCT Pub. Date: May 23, 2019

(65) Prior Publication Data
US 2020/0289421 A1    Sep. 17, 2020

Related U.S. Application Data

(60) Provisional application No. 62/681,866, filed on Jun. 7, 2018, provisional application No. 62/681,852, filed
(Continued)

(51) Int. Cl.
*A61K 9/48* (2006.01)
*A61K 38/26* (2006.01)
(Continued)

(52) U.S. Cl.
CPC ............... *A61K 9/48* (2013.01); *A61K 31/14* (2013.01); *A61K 31/201* (2013.01); *A61K 38/26* (2013.01);
(Continued)

(58) Field of Classification Search
CPC ...... A61K 31/14; A61K 31/201; A61K 47/12; A61K 47/186; A61K 9/0053; A61K 9/48
See application file for complete search history.

(56) References Cited

U.S. PATENT DOCUMENTS 5,124,061 A     6/1992  Geary, Sr.
2004/0258747 A1  12/2004  Ponzoni et al.
(Continued)

FOREIGN PATENT DOCUMENTS

CN      106420610 A     2/2017
KR      20170052278 A   5/2017
(Continued)

OTHER PUBLICATIONS

Sahvaz et al; "Transformation of Poorly Water-Soluble Drugs into Lipophilic Ionic Liquids Enhances Oral Drug Exposure from Lipid Based Formulations"; Mol. Pharmaceutics; 2015; 12:1980-1991 (Year: 2015).*

(Continued)

*Primary Examiner* — Timothy P Thomas
(74) *Attorney, Agent, or Firm* — Nixon Peabody LLP; David S. Resnick; Nicole D. Kling

(57) ABSTRACT

The technology described herein is directed to compositions comprising CAGE and at least one active compound, e.g., for oral or parenteral administration.

11 Claims, 36 Drawing Sheets

Specification includes a Sequence Listing.

Related U.S. Application Data on Jun. 7, 2018, provisional application No. 62/681,856, filed on Jun. 7, 2018, provisional application No. 62/681,861, filed on Jun. 7, 2018, provisional application No. 62/588,008, filed on Nov. 17, 2017.

(51) Int. Cl.

| | | |
|---|---|---|
| *A61K 38/28* | (2006.01) | |
| *A61K 47/12* | (2006.01) | |
| *A61K 47/18* | (2017.01) | |
| *A61K 31/201* | (2006.01) | |
| *A61K 31/14* | (2006.01) | |
| *A61K 9/00* | (2006.01) | |
| *A61P 3/10* | (2006.01) | |
| *A61P 35/04* | (2006.01) | |

(52) U.S. Cl.
CPC .............. *A61K 38/28* (2013.01); *A61K 47/12* (2013.01); *A61K 47/186* (2013.01); *A61P 3/10* (2018.01); *A61P 35/04* (2018.01); *A61K 9/0034* (2013.01); *A61K 9/0043* (2013.01); *A61K 9/0053* (2013.01)

(56) References Cited

U.S. PATENT DOCUMENTS

| | | | |
|---|---|---|---|
| 2015/0071922 A1 | 3/2015 | Larson et al. | |
| 2015/0164828 A1 | 6/2015 | Golini | |
| 2015/0328113 A1 | 11/2015 | Patel et al. | |
| 2016/0263225 A1* | 9/2016 | Zakrewsky | ............. A61P 17/10 |
| 2018/0093011 A1 | 4/2018 | Kellar et al. | |

FOREIGN PATENT DOCUMENTS

| | | |
|---|---|---|
| WO | 2004052340 A1 | 6/2004 |
| WO | 2015066647 A2 | 5/2015 |
| WO | 2016054259 A1 | 4/2016 |
| WO | 2017164627 A2 | 9/2017 |
| WO | 2018044920 A1 | 3/2018 |
| WO | 2018222924 A1 | 12/2018 |

OTHER PUBLICATIONS

Vllasaliu et al.; "Recent Advances in oral delivery of biologics: Nanomedicine and physical modes of delivery"; Expert opinion on drug delivery 2018; 15(8); 759-770 (Year: 2019).*
Hsu et al. "Delivery of siRNA and other macromolecules into skin and cells using a peptide enhancer." Proceedings of the National Academy of Sciences 108(38): 15816-15821 (2011).
Karande et al. "Discovery of transdermal penetration enhancers by high-throughput screening." Nature Biotechnology 22(2): 192-197 (2004).
Kumar et al. "Peptides as skin penetration enhancers: mechanisms of action." Journal of Controlled Release 199: 168-178 (2015).
Lane. "Skin penetration enhancers." International Journal of Pharmaceutics 447(1-2): 12-21 (2013).
Zeisel. "Choline: Human requirements and effects on human performance." In Food Components to Enhance Performance: An Evaluation of Potential Performance-Enhancing Food Components for Operational Rations. Institute of Medicine, Committee on Military Nutritional Research Food and Nutrition Board, B. M. Marriott, Ed. National Academies Press, Washington DC. Chapter 19: 381-406 (1994).
Araki et al. "Ionic liquid-mediated transcutaneous protein delivery with solid-in-oil nanodispersions." MedChemComm 6(12): 2124-2128 (2015).
Dobler et al. "Ionic liquids as ingredients in topical drug delivery systems." International Journal of Pharmaceutics 441(1-2): 620-627 (2013).
Goindi et al. "Development of novel ionic liquid-based microemulsion formulation for dermal delivery of 5-fluorouracil." AAPS PharmSciTech 15(4): 810-821 (2014).
Moniruzzaman et al. "Ionic liquid based microemulsion with pharmaceutically accepted components: Formulation and potential applications." Journal of Colloid and Interface Science 352(1): 136-142 (2010).
Hough et al., (The Third Evolution of Ionic Liquids: Active Pharmaceutical Ingredients New Journal of Chemistry 31 (8): 1429 (2014).
Abbott et al., "Deep eutectic solvents formed between choline chloride and carboxylic acids: versatile alternatives to ionic liquids." Journal of the American Chemical Society 126(29):9142-9147 (2004).
Adawiyah et al., "Ionic liquids as a potential tool for drug delivery systems." MedChemComm 7(10):1881-1897 (2016).
Chen et al. "Enhanced paracellular delivery of vaccine by hydrogel microparticles-mediated reversible tight junction opening for effective oral immunization." Journal of Controlled Release 311-312: 50-64 (2019).
Fan et al. "Functional nanoparticles exploit the bile acid pathway to overcome multiple barriers of the intestinal epithelium for oral insulin delivery." Biomaterials 151: 13-23 (2018).
Fiebig et al., "Quantitative evaluation of myoglobin unfolding in the presence of guanidinium hydrochloride and ionic liquids in solution." The Journal of Physical Chemistry B 118(2):406-412 (2013).
Kandimalla et al. "Effect of fatty acids on the permeation of melatonin across rat and pig skin in-vitro and on the transepidermal water loss in rats in-vivo." JPharmPharmacol 51(7): 783-790 (2010).
Kelley et al., "Understanding the effects of ionicity in salts, solvates, co-crystals, ionic co-crystals, and ionic liquids, rather than nomenclature, is critical to understanding their behavior." Crystal Growth and Design. 13(3):965-975 (2013).
Korkmaz et al., "Therapeutic intradermal delivery of tumor necrosis factor-alpha antibodies using tip-loaded dissolvable microneedle arrays." Acta Biomaterialia 24:96-105 (2015).
Lee et al. "Development of pH-responsive organic-inorganic hybrid nanocomposites as an effective oral delivery system of protein drugs." Journal of Controlled Release 311-312: 74-84 (2019).
Li et al., "Insights into the deactivation of bovine serum albumin with a thermo-responsive ionic liquid." Soft Matter 10 (33):6161-6171 (2014).
Li et al. "Micromotors Spontaneously Neutralize Gastric Acid for pH-Responsive Payload Release." Angewandte Chemie International Edition 56(8): 2156-2161 (2017).
Monti et al. "Ionic liquids as potential enhancers for transdermal drug delivery." Int J Pharm 516(1-2): 45-51 (2017).
Park et al. "Lidocaine-ibuprofen ionic liquid for dermal anesthesia." AIChE Journal 61(9): 2732-2738 (2015).
Patel et al., "Recent advances in the applications of ionic liquids in protein stability and activity: a review." Applied Biochemistry and Biotechnology 172(8):3701-3720 (2014).
Paul et al., "Deciphering the interaction of a model transport protein with a prototypical imidazolium room temperature ionic liquid: effect on the conformation and activity of the protein." Journal of Photochemistry and Photobiology B: Biology 133:99-107 (2014).
Rogers et al., "Ionic liquids—solvents of the future?." Science 302(5646):792-793 (2003).
Sahbaz et al., "Transformation of poorly water-soluble drugs into lipophilic ionic liquids enhances oral drug exposure from lipid based formulations." Molecular Pharmaceutics 12(6):1980-1991 (2015).
Shamshina et al., "Ionic liquids in drug delivery." Expert Opinion on Drug Delivery 10(10):1367-1381 (2013).
Sivapragasam et al., "Recent advances in exploiting ionic liquids for biomolecules: solubility, stability and applications." Biotechnology Journal 11(8):1000-1013 (2016).
Streit et al., "Topical application of the tumour necrosis factor-α antibody infliximab improves healing of chronic wounds." International Wound Journal 3(3):171-179 (2006).
Vllasaliu et al. "Recent advances in oral delivery of biologics: Nanomedicine and physical modes of delivery." Expert opinion on drug delivery 15(8): 759-770 (2018).

(56) References Cited

OTHER PUBLICATIONS

Wu et al. "Improving dermal delivery of hydrophilic macromolecules by biocompatible ionic liquid based on choline and malic acid." Int J Pharm 558: 380-387 (2019).
Zakrewsky et al., "Choline and geranate deep eutectic solvent as a broad-spectrum antiseptic agent for preventive and therapeutic applications." Advanced Healthcare Materials 5(11):1282-1289 (2016).
Zhang et al. "Evaluations of imidazolium ionic liquids as novel skin permeation enhancers for drug transdermal delivery." Pharm Dev Technol 22(4): 511-520 (2017).
Banerjee et al., "Transdermal protein delivery using choline and geranate (CAGE) deep eutectic solvent." Advanced Healthcare Materials 6(15):1601411 (2017).
Berton et al. "Transdermal Bioavailability in Rats of Lidocaine in the Forms of Ionic Liquids, Salts, and Deep Eutectic." ACS Med Chem Lett 8(5): 498-503 (2017).
Carrillo-Conde et al. "Complexation hydrogels as oral delivery vehicles of therapeutic antibodies: an in vitro and ex vivo evaluation of antibody stability and bioactivity." Industrial & engineering chemistry research 54(42): 10197-10205 (2015).
De Ávila et al. "Micromotor-enabled active drug delivery for in vivo treatment of stomach infection." Nature communications 8(1): 272 pp. 1-9 (2017).
Egorova et al., "Biological activity of ionic liquids and their application in pharmaceutics and medicine." Chemical Reviews 117(10):7132-7189 (2017).
Esteban-Fernández De Ávila et al. "Micromotors go in vivo: from test tubes to live animals." Advanced Functional Materials 28(25): 1705640 (2018).
Haidari et al., "Development of topical delivery systems for flightless neutralizing antibody." Journal of Pharmaceutical Sciences 106(7):1795-1804 (2017).
Jain et al., "Effect of trehalose on protein structure." Protein Science 18(1):24-36 (2009).
Jean. "Esters et sels de la choline et de quelues acides derives du phosphore." Bulletin de la Societe Chimique de France 5: 783-786 (1957).
Karande et al., "Design principles of chemical penetration enhancers for transdermal drug delivery." PNAS 102 (13):4688-4693 (2005).
Khan et al., "Key interactions of surfactants in therapeutic protein formulations: A review." European Journal of Pharmaceutics and Biopharmaceutics 97 97(Pt A):60-67 (2015).
Kharroubi et al., "Diabetes mellitus: The epidemic of the century." World Journal of Diabetes 6(6):850-867 (2015).
Korkmaz et al., "Topically applied flightless I neutralizing antibodies improve healing of blistered skin in in a murine model of epidermolysis bullosa acquisita." Journal of Investigative Dermatology 133(4):1008-1016 (2013).
Lei et al., "Introduction: ionic liquids." Chem Rev 117(10):6633-6635 (2017).
Lesch et al., "Peptides in the presence of aqueous ionic liquids-tunable co-solutes as denaturants or protectants?" Physical Chemistry Chemical Physics 17(39):26049-26053 (2015).
Marrucho et al., "Ionic liquids in pharmaceutical applications." Annual Review of Chemical and Biomolecular Engineering 5:527-546 (2014).
Muheem et al. "A review on the strategies for oral delivery of proteins and peptides and their clinical perspectives." Saudi Pharmaceutical Journal 24(4): 413-428 (2016).
Shao "On the influence of hydrated imidazolium-based ionic liquid on protein structure stability: a molecular dynamics simulation study." The Journal of Chemical Physics 139(11):115102 (2013).
Singh et al., "Effect of polysorbate 20 and polysorbate 80 on the higher-order structure of a monoclonal antibody and its Fab and Fc fragments probed using 2D nuclear magnetic resonance spectroscopy." Journal of Pharmaceutical Sciences 106(12):3486-3498 (2017).
Veselinovic et al., "Topical gel formulation of broadly neutralizing anti-HIV-1 monoclonal antibody VRC01 confers protection against HIV-1 vaginal challenge in a humanized mouse model." Virology 432(2):505-510 (2012).
Wang et al., "Stabilizing two IgG1 monoclonal antibodies by surfactants: Balance between aggregation prevention and structure perturbation." European Journal of Pharmaceutics and Biopharmaceutics 114:263-277 (2017).
Wei, et al. "Biomimetic Micromotor Enables Active Delivery of Antigens for Oral Vaccination." Nano letters 19(3): 1914-1921 (2019).
Williams et al., "Ionic liquids provide unique opportunities for oral drug delivery: structure optimization and in vivo evidence of utility." Chemical Communications 50(14):1688-1690 (2014).
Yang et al., "Using ionic liquids in whole-cell biocatalysis for the nucleoside acylation." Microbial Cell Factories 13 (1):143 (2014).
Zakrewsky et al., "Ionic liquids as a class of materials for transdermal delivery and pathogen neutralization." PNAS 111(37):13313-13318 (2014).
O'Toole et al. "Diphosphonium ionic liquids as broad spectrum antimicrobial agents." Cornea 31(7): 810-816 (2012).
Petkovic et al. "Novel biocompatible cholinium-based ionic liquids—toxicity and biodegradability." Green Chemistry 12(4): 643-649 (2010).

* cited by examiner

(56) # IONIC LIQUIDS FOR INTERNAL DELIVERY

CROSS-REFERENCE TO RELATED APPLICATIONS

This application is a 35 U.S.C. § 371 National Phase Entry Application of International Application No. PCT/US2018/061532 filed Nov. 16, 2018, which designates the U.S. and claims benefit under 35 U.S.C. § 119(e) of U.S. Provisional Application No. 62/588,008 filed Nov. 17, 2017, U.S. Provisional Application No. 62/681,852 filed Jun. 7, 2018, U.S. Provisional Application No. 62/681,856 filed Jun. 7, 2018, U.S. Provisional Application No. 62/681,861 filed Jun. 7, 2018, U.S. Provisional Application No. 62/681,866 filed Jun. 7, 2018, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 7, 2020, is named 002806-090490WOPT_SL.txt and is 3,127 bytes in size.

TECHNICAL FIELD

The technology described herein relates to ionic liquids, e.g., CAGE, for stabilization and delivery of active compounds.

BACKGROUND

The uptake of many active compounds, e.g., pharmaceutically active compounds, can be improved by delivering the compounds in solvents. However, such approaches are often unsuitable for in vivo use because most such solvents demonstrate toxic side effects and/or act as irritants to the point of delivery. These toxic and irritant effects are severe enough to mitigate any increase in the uptake or performance of the active compound.

SUMMARY

As demonstrated herein, the inventors have found that a particular ionic liquid, CAGE, provides improved active compound uptake kinetics while surprisingly not causing deleterious side effects. This surprising effect holds for a number of delivery routes which are typically susceptible to toxicity and irritation caused by carrier solvents. This lack of toxic side effects is particularly surprising as CAGE is known to have antimicrobial properties.

In one aspect of any of the embodiments, described herein is a method of oral delivery of at least one active compound, the method comprising orally administering the active compound in combination with a composition comprising an ionic liquid of Choline And GEranate (CAGE). In one aspect of any of the embodiments, described herein is a method of delivery of at least one active compound, the method comprising subcutaneously, intradermally or intravenously administering the active compound in combination with CAGE. In one aspect of any of the embodiments, described herein is a method of delivery of at least one active compound, the method comprising administering the active compound in combination with CAGE to a mucus membrane.

In one aspect of any of the embodiments, described herein is a method of parenteral delivery of at least one active compound, the method comprising parenterally administering the active compound in combination with CAGE. In some embodiments of any of the aspects, the administration comprises delivery to a tumor. In one aspect of any of the embodiments, described herein is a method of treating a disease in a subject in need thereof by administering to the subject an active compound in combination with CAGE by into the affected tissue by injection. In some embodiments of any of the aspects, the disease is cancer, excess fat, fat, wart, hyperplasia or any other disease arising from undesired tissue growth.

In one aspect of any of the embodiments, described herein is a composition comprising an active compound in combination with CAGE. In some embodiments of any of the aspects, the composition further comprises a further pharmaceutically acceptable carrier.

In some embodiments of any of the aspects, the composition is formulated as an oral, subcutaneous, or parenteral formulation. In some embodiments of any of the aspects, the oral formulation is a degradable capsule comprising the combination of the active compound and CAGE.

In some embodiments of any of the aspects, the CAGE is at a concentration of at least 0.1% w/v. In some embodiments of any of the aspects, the CAGE comprises a ratio of choline:geranic acid or geranate of from about 2:1 to about 1:10. In some embodiments of any of the aspects, the CAGE comprises a ratio of choline:geranic acid or geranate of from about 1:1 to about 1:4. In some embodiments of any of the aspects, the CAGE comprises a ratio of choline:geranic acid or geranate of from about 1:2 to about 1:4. In some embodiments of any of the aspects, the ionic liquid's anion comprises geranate and/or geranic acid.

In some embodiments of any of the aspects, the active compound in combination with CAGE is administered once. In some embodiments of any of the aspects, the active compound in combination with CAGE is administered in multiple doses.

In some embodiments of any of the aspects, the active compound comprises a nucleic acid molecule. In some embodiments of any of the aspects, the active compound comprises a small molecule. In some embodiments of any of the aspects, the active compound comprises a polypeptide. In some embodiments of any of the aspects, the active compound comprises a chemotherapeutic compound. In some embodiments of any of the aspects, the active compound comprises insulin. In some embodiments of any of the aspects, the active compound comprises an antibody or antibody reagent.

In some embodiments of any of the aspects, the biological activity of the active compound is improved or stabilized as compared to the activity in the absence of CAGE.

In some embodiments of any of the aspects, the combination of the active compound and CAGE is an admixture. In some embodiments of any of the aspects, the combination of the active compound and CAGE comprises nanoparticles comprising the active compound, the nanoparticles in solution or suspension in a composition comprising CAGE.

As demonstrated herein, the inventors have found that a particular ionic liquid, CAGE, reduces the uptake of lipophilic molecules in the intestine. Accordingly, CAGE can reduce fat absorption in a subject, providing a treatment for obesity or reducing weight/weight gain.

In one aspect of any of the embodiments, provided herein is a method of treating obesity, preventing weight gain, or reducing a subject's weight, the method comprising orally administering to the subject a composition comprising an ionic liquid of Choline And GEranate (CAGE).

In some embodiments of any of the aspects, the CAGE is at a concentration of at least 0.1% w/v. In some embodiments of any of the aspects, the CAGE comprises a ratio of choline:geranic acid or geranate of from about 2:1 to about 1:10. In some embodiments of any of the aspects, the CAGE comprises a ratio of choline:geranic acid or geranate of from about 1:1 to about 1:4. In some embodiments of any of the aspects, the ionic liquid's anion comprises geranate and/or geranic acid.

In some embodiments of any of the aspects, the composition further comprises an active compound. In some embodiments of any of the aspects, the active compound is therapeutically effective in treating obesity or a disease associated with obesity. In some embodiments of any of the aspects, a small molecule, a polypeptide, or an antibody or antibody reagent.

As shown herein, salts (e.g., ionic liquids or CAGE) show a surprising increase in drug delivery efficacy (e.g., ability to cross cells and/or cell membranes) at concentrations of 0.05M or greater. Accordingly, described herein is a method of delivery of at least one active compound, the method administering the active compound in combination with a composition comprising a salt, wherein the salt is present at a concentration of at least 0.05M. Further described herein is a method of delivery of CAGE, the method administering the CAGE at a concentration of at least 0.05M. In one aspect of any of the embodiments, described herein is a composition comprising a salt, wherein the salt is present at a concentration of at least 0.05M; and an active compound.

In some embodiments of any of the aspects, the salt is an ionic liquid. In some embodiments of any of the aspects, the ionic liquid is Choline And GEranate (CAGE). In some embodiments of any of the aspects, the cation is choline. In some embodiments of any of the aspects, the anion is geranate or geranic acid.

In some embodiments of any of the aspects, the delivery is oral, subcutaneous, intradermal, intravenous, parenteral, or to a mucus membrane. In some embodiments of any of the aspects, the delivery is oral.

In some embodiments of any of the aspects, the salt is present at a concentration of at least 0.05M, 0.1M, 0.5M, 1M, 1.5 M, 2 M, 2.5 M, 3 M, 3.5 M, 4M, or greater. In some embodiments of any of the aspects, the salt is present at a concentration of from about 0.05 M to about 4 M.

In some embodiments of any of the aspects, the salt dissolves after administration. In some embodiments of any of the aspects, the salt is a pure or anhydrous liquid. In some embodiments of any of the aspects, the salt is an aqueous solution.

In some embodiments of any of the aspects, the administration is administration to a subject. In some embodiments of any of the aspects, the administration is contacting a cell and/or tissue.

In some embodiments of any of the aspects, the active compound comprises a nucleic acid molecule, a chemotherapeutic compound, a small molecule, a peptide, and/or an antibody or antibody reagent. In some embodiments of any of the aspects, the active compound is a component of the salt. In some embodiments of any of the aspects, the active compound comprises insulin.

In some embodiments of any of the aspects, the biological activity of the active compound is improved or stabilized as compared to the activity in the absence of the salt. In some embodiments of any of the aspects, the combination of the active compound and the salt is an admixture. In some embodiments of any of the aspects, the combination of the active compound and the salt comprises nanoparticles comprising the active compound, the nanoparticles in solution or suspension in a composition comprising the salt.

As demonstrated herein, the ionic liquid Choline And GEranate (CAGE) is demonstrated to have enzyme inhibitor activity, including inhibiting the degradation of insulin. Accordingly, provided herein are methods and compositions relating to the use of an ionic liquid, e.g., CAGE, to treat certain diseases. In one aspect of any of the embodiments, described herein is a method of administering an enzyme inhibition therapy to a subject in need thereof, the method comprising administering to the subject a composition comprising the ionic liquid Choline And GEranate (CAGE). In one aspect of any of the embodiments, described herein is a method of treating diabetes, ulcers, cancer, or fibrosis in a subject in need thereof, the method comprising administering to the subject a composition comprising the ionic liquid Choline And GEranate (CAGE).

In some embodiments of any of the aspects, the composition comprising CAGE does not comprise a further therapeutically active agent. In some embodiments of any of the aspects, the subject is not administered a further therapeutically active agent for the condition (e.g., diabetes, ulcers, cancer, or fibrosis) during the period of time during which the subject is administered the composition comprising CAGE and/or during the period of time during which the subject is administered a treatment regimen which comprises a composition comprising CAGE.

In some embodiments of any of the aspects, the administration is via injection or is oral.

In some embodiments of any of the aspects, the CAGE is at a concentration of at least 0.1% w/v. In some embodiments of any of the aspects, the CAGE comprises a ratio of choline:geranic acid or geranate of from about 2:1 to about 1:10. In some embodiments of any of the aspects, the CAGE comprises a ratio of choline:geranic acid or geranate of from about 1:1 to about 1:4. In some embodiments of any of the aspects, the CAGE comprises a ratio of choline:geranic acid or geranate of from about 1:2 to about 1:4. In some embodiments of any of the aspects, the ionic liquid's anion comprises geranate and/or geranic acid.

BRIEF DESCRIPTION OF THE DRAWINGS

(FIG. 8A) intrajejunal administration of neat CAGE; (FIG. 8B) intrajejunal administration of saline; (FIG. 8C) oral administration of neat CAGE; (FIG. 8D) oral administration of insulin-saline; (FIG. 8E) oral administration of insulin-CAGE. Scale bar: 200 µm. Inserts are mucosal surface with scale bar of 50 µm.

FIG. 16A depicts the efficacy of various formulations after normalizing for fasting effect related blood glucose changes. Animals injected with saline alone were considered as the fasting group and data plotted after subtracting the blood glucose obtained from the saline group. FIG. 16B depicts blood glucose changes compared to initial levels without normalizing saline blood glucose levels. All data are represented as mean±standard error (S.E.) (n=6). A significantly higher (p<0.05) efficacy was noted in the efficacy of 5 U/kg insulin-CAGE treated rats at various time points of the study compared to subcutaneously administered 2 U/kg insulin (represented by *).

FIG. 18A depicts the efficacy of various formulations after normalizing for fasting effect related blood glucose changes. Animals administered with empty capsules were considered as the fasting group and data plotted after subtracting blood glucose changes obtained from the empty capsule group. FIG. 18B depicts blood glucose changes compared to initial levels without normalizing for empty capsule blood glucose levels. All data are represented as mean±S.E. (n=6). A significantly higher (p<0.05) efficacy of CAGE-insulin was observed at various time points (represented as *) compared to subcutaneously administered insulin.

(FIG. 31B) 5%, w/w, CAGE-1:3; (FIG. 31C) 5%, w/w, CAGE-1:4; (FIG. 31D) micelles of 20%, w/w, CAGE-1:2; (FIG. 31E) vesicles of 20% CAGE-1:3; and (FIG. 31F) vesicles of CAGE1:4.

DETAILED DESCRIPTION

Figure 1:
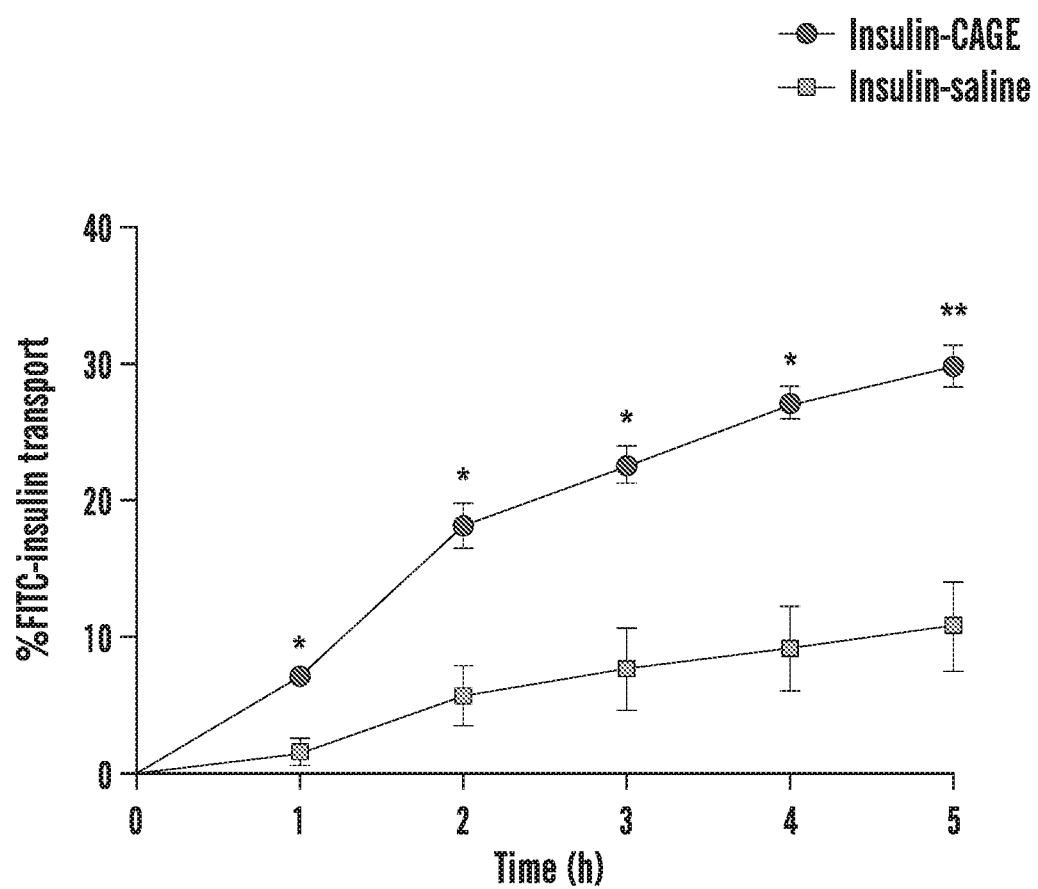
FIG. 1 demonstrates enhancement in FITC-insulin transport across Caco-2 monolayers in presence of CAGE. Data represented as mean±S.E. (n=6) (* p<0.01, ** p<0.001)

As described herein, the inventors have demonstrated that the ionic liquid CAGE (choline and geranate or gernanic acid) is not only safe for use orally and/or parenterally, but significantly improves delivery of active compounds comprised in a solution of CAGE, without the negative side effects typically observed for most solvents. Indeed, solvents as a class present a general problem of toxicity, thus "solvent exposure" being a commonly used medical term meant to encompass the hazards of contact with one or more solvents. Solvent exposure generally, as well as exposure to select individual solvents, has been demonstrated to contribute to the etiology of a number of conditions. In light of this, the safety profile of CAGE demonstrated herein is particularly surprising and unexpected, particularly via the oral and parenteral administration routes, which bypass many of the body's natural defenses.

Accordingly, in one aspect of any of the embodiments, described herein is a method of oral delivery of at least one active compound, the method comprising orally administering a composition comprising the active compound in combination with the ionic liquid Choline And GEranate (CAGE).

Oral administration can comprise providing tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Oral formulations can comprise discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of CAGE and the at least one active compound, and may be prepared by methods of pharmacy well known to those skilled in the art. See generally, Remington: The Science and Practice of Pharmacy, 21st Ed., Lippincott, Williams, and Wilkins, Philadelphia Pa. (2005).

In one aspect of any of the embodiments, described herein is a method of treatment of diabetes comprising orally administering an oral formulation of insulin in combination with CAGE. In one aspect of any of the embodiments, described herein is a method of treatment of diabetes comprising orally administering an oral formulation of a GLP-1 polypeptide or mimetic/analog thereof in combination with CAGE.

It is noted herein that oral and topical administration differ widely, e.g., in the character of the cell layers that must be crossed in order for administration to permit the active compound to penetrate to the interior of the organism. In the skin, the first layer to be traversed by an administered composition is the epidermis, which is comprised of stratified squamous epithelium and then a basal lamina. The epidermis has a least 5 strata and the most common cell types are Merkel cells, keratinocytes, malanocytes, and Langerhans cells. Notably, the most exterior surface of the skin comprises a 25-30 cell deep layer of dead cells. Beneath the epidermis is the dermis, which comprises connective tissue, vessels, and various glands. In contrast, for oral administration, the composition immediately contacts the intestinal epithelium, which is a single layer of simple columnar epithelial cells with two thin underlying laminae. In addition, the intestinal epithelium forms tight junctions in order to provide impermeability, while the skin comprises keratin in order to form an external barrier for the organism. Thus, the questions of transiting each of these tissues, without causing undue damage, are significantly divergent, and the tissues encountered during oral administration are clearly much more readily susceptible to irritation and toxicity.

As described elsewhere herein, CAGE is able to safely carry active compounds across the sensitive membranes encountered during oral administration. Similarly, CAGE can safely deliver active compounds across other sensitive interior tissues.

As described in the examples herein, CAGE provides both protease inhibitors and mucolytic activity. Accordingly, it is particularly suitable as delivery vehicle to/across mucus membranes. In one aspect of any of the embodiments, described herein is a method of delivery of at least one active compound, the method comprising administering the active compound in combination with CAGE to a mucus membrane, e.g., a nasal, oral, or vaginal membrane.

CAGE also serves to solubilize the drug, thus enabling injections of high concentrations. CAGE also diffuses in tissue at a greater rate than traditional solubilizing carriers, e.g., EtOH. In some embodiments, without wishing to be bound by theory, CAGE can also diffuse into the tissue, thus allowing local precipitation of the drug. The precipitated drug can form a depot and exhibit sustained release.

In another embodiment, the drug may continue to remain soluble in CAGE even after local diffusion of CAGE and lead to quick and enhanced delivery into circulation. Subcutaneous delivery often necessitates multiple doses or controlled release formulations. Such approaches are not necessarily performed due to any concern about timing per se, but rather done to ensure that the entire dose is received prior to degradation of the active compound. Bolus administration is often ineffective because the active compound degrades or is metabolized before the full dose can exert an effect. Due the ability of CAGE to stabilize active compounds, such approaches are unnecessary, i.e., the total desired dose can be delivered as a single administration without the need for controlled release mechanisms.

Accordingly, in one aspect of any of the embodiments, described herein is a method of delivery of at least one active compound by subcutaneous, intradermal or intravenous administration, the method comprising administering the active compound in combination with CAGE. In some embodiments of any of the aspects, subcutaneous, intradermal or intravenous administration comprises administration via injection, catheter, port, or the like.

The inventors have further demonstrated that at higher concentrations, CAGE provides a cytotoxic effect, wherein more than 50% of cells exposed to CAGE are killed This is particularly useful for applications where the active compound itself is designed to be cytotoxic or cytostatic or the disease can be treated by inhibiting the growth of one or more cell types (e.g., cancer). The concentration of CAGE which is appropriate for cytotoxicity can vary depending upon, e.g., the target tissue type, the stoichiometric ratio of CAGE being used, the volume of composition being administered, and/or the extent of effects desired.

Accordingly, in one aspect of any of the embodiments, described herein is a method of parenteral delivery of at least one active compound, the method comprising parenterally administering the active compound in combination with CAGE. In some embodiments, the parenteral administration comprises delivery to a tumor, e.g., a cancer tumor.

In some embodiments, the composition comprising CAGE in combination with at least one active compound as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition comprising CAGE in combination with at least one active compound as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of an ingredient in a composition as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. While as noted above herein, the compositions comprising CAGE in combination with at least one active compound can obviate certain reasons for using a controlled-release formulation, it is contemplated herein that the methods and compositions can be utilized in controlled-release formulations in some embodiments. For example, controlled-release formulations can be used to control a drug's onset of action, duration of action, plasma levels within the therapeutic window, and peak blood levels.

In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition comprising CAGE in combination with at least one active compound can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In one aspect of any of the embodiments, described herein is a method of treating a disease in a subject in need thereof by administering to the subject an active compound in combination with CAGE by into the affected tissue by injection. In some embodiments, the affected tissue is tissue comprising diseased cells. In some embodiments, the affected tissue is tissue displaying symptoms of the disease. Non-limiting examples of suitable affected tissues include tumor tissue, fat tissue, a wart, undesired adipose tissue, or the like.

In some embodiments of any of the aspects the disease is a disease arising from tissue growth, e.g., unwanted, aberrant, or pathological tissue growth. A disease arising from tissue growth can be any disease caused by or characterized by, a rate of tissue growth, location of tissue growth, or pattern/structure of tissue growth which differs from what is normal for that tissue type in a healthy subject. Non-limiting examples of such diseases are tumors, cancer, fat/obesity, warts, and/or hyperplasia.

The term "ionic liquids (ILs)" as used herein refers to organic salts or mixtures of organic salts which are in liquid state at room temperature. This class of solvents has been shown to be useful in a variety of fields, including in industrial processing, catalysis, pharmaceuticals, and electrochemistry. The ionic liquids contain at least one anionic and at least one cationic component. Ionic liquids can comprise an additional hydrogen bond donor (i.e. any molecule that can provide an —OH or an —NH group), examples include but are not limited to alcohols, fatty acids, and amines. The at least one anionic and at least one cationic component may be present in any molar ratio. Exemplary molar ratios (cation:anion) include but are not limited to 1:1, 1:2, 2:1, 1:3, 3:1, 2:3, 3:2, and ranges between these ratios. For further discussion of ionic liquids, see, e.g., Hough, et ah, "The third evolution of ionic liquids: active pharmaceutical ingredients", New Journal of Chemistry, 31: 1429 (2007) and Xu, et al., "Ionic Liquids: Ion Mobilities, Glass Temperatures, and Fragilities", Journal of Physical Chemistry B, 107(25): 6170-6178 (2003); each of which is incorporated by reference herein in its entirety. In some embodiments of any of the aspects, the ionic liquid or solvent exists as a liquid below 100° C. In some embodiments of any of the aspects, the ionic liquid or solvent exists as a liquid at room temperature.

In some embodiments of any of the aspects, the ionic liquid described herein is CAGE (Choline And GEranate). CAGE is an ionic liquid comprising the cation choline (see, e.g., Structure I) and the anion geranate or geranic acid (see, e.g., Structures II and III). Preparation of CAGE can be, e.g., as described in U.S. Patent Publication US2016/0263225; which is incorporated by reference herein in its entirety, or as described in the examples herein.

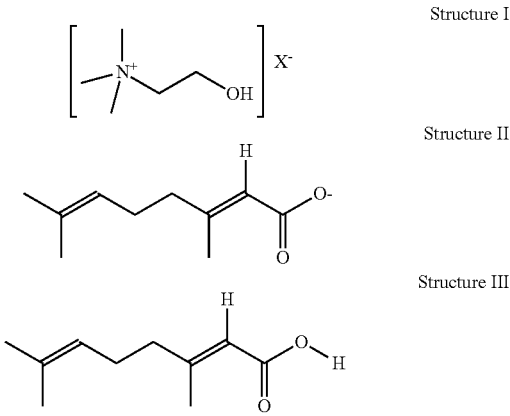

Structure I

Structure II

Structure III

In some embodiments of any of the aspects, the ionic liquid's anion comprises geranate and/or geranic acid. In some embodiments of any of the aspects, the ionic liquid's anion comprises geranate. In some embodiments of any of the aspects, the ionic liquid's anion comprises geranic acid.

In some embodiments of any of the aspects, the CAGE is at a concentration of at least 0.01% w/v. In some embodiments of any of the aspects, the CAGE is at a concentration of at least 0.05% w/v. In some embodiments of any of the aspects, the CAGE is at a concentration of at least 0.1% w/v. In some embodiments of any of the aspects, the CAGE is at a concentration of at least 0.2% w/v, at least 0.3% w/v, at least 0.4% w/v, at least 0.5% w/v, at least 1% w/v or greater.

In some embodiments of any of the aspects, the CAGE is at a concentration of from about 0.01% w/v to about 1% w/v. In some embodiments of any of the aspects, the CAGE is at a concentration of from 0.01% w/v to 1% w/v. In some embodiments of any of the aspects, the CAGE is at a concentration of from about 0.05% w/v to about 0.5% w/v. In some embodiments of any of the aspects, the CAGE is at a concentration of from 0.05% w/v to 0.5% w/v.

In some embodiments of any of the aspects, the CAGE is at a concentration of at least 25% w/w. In some embodiments of any of the aspects, the CAGE is at a concentration of at least 25% w/w in water. In some embodiments of any of the aspects, the CAGE is at a concentration of at least 25% w/w in saline or a physiologically compatible buffer.

In some embodiments of any of the aspects, the CAGE is at a concentration of from about 5% w/w to about 75% w/w. In some embodiments of any of the aspects, the CAGE is at a concentration of from 5% w/w to 75% w/w. In some embodiments of any of the aspects, the CAGE is at a concentration of from about 5% w/w to about 75% w/w in water, saline or a physiologically compatible buffer. In some embodiments of any of the aspects, the CAGE is at a concentration of from 5% w/w to 75% w/w in water, saline or a physiologically compatible buffer.

As described herein, different structures can be achieved by varying the concentration and ratios of the CAGE. Increasing degree of hydration disrupted the native molecular and ionic clusters, leading to a nanoscale reorganization that affected the polar and non-polar domains, the adjacency of atoms, as well as intra and intermolecular interactions. With a high degree of hydration, >75% $H_2O$, the nanostructures of DES self-assembled into vesicles, spheroidal micelles and o/w microemulsion depending on the molar ratio of the precursors.

In some embodiments of any of the aspects, the CAGE has a ratio of choline:geranic acid (or geranate) of about 1:4 and is at a concentration of about 5% w/w, providing a microemulsion. In some embodiments of any of the aspects, the CAGE has a ratio of choline:geranic acid (or geranate) of about 1:3 to about 1:4 and is at a concentration of about 20% w/w, providing vesicles. In some embodiments of any of the aspects, the CAGE has a ratio of choline:geranic acid (or geranate) of about 1:2 and is at a concentration of about 20% w/w, providing micelles. In some embodiments of any of the aspects, the CAGE has a ratio of choline:geranic acid (or geranate) of about 1:4 and is at a concentration of about 50% w/w, providing a sol-gel.

In some embodiments of any of the aspects, the CAGE is a gel, or a shear-thinning Newtonian gel.

In some embodiments of any of the aspects, the CAGE is at a concentration of at least 25% w/w and has a ratio of choline:geranic acid (or geranate) of at least 1:3. In some embodiments of any of the aspects, the CAGE is at a concentration of at least 25% w/w in water and has a ratio of choline:geranic acid (or geranate) of at least 1:3. In some embodiments of any of the aspects, the CAGE is at a concentration of at least 25% w/w and has a ratio of choline:geranic acid (or geranate) of 1:3 or 1:4. In some embodiments of any of the aspects, the CAGE is at a concentration of at least 25% w/w in water and has a ratio of choline:geranic acid (or geranate) of 1:3 or 1:4. In some embodiments of any of the aspects, the CAGE is a gel, or a shear-thinning Newtonian gel.

In some embodiments of any of the aspects, the CAGE is 100% by w/w or w/v.

Figure 11:
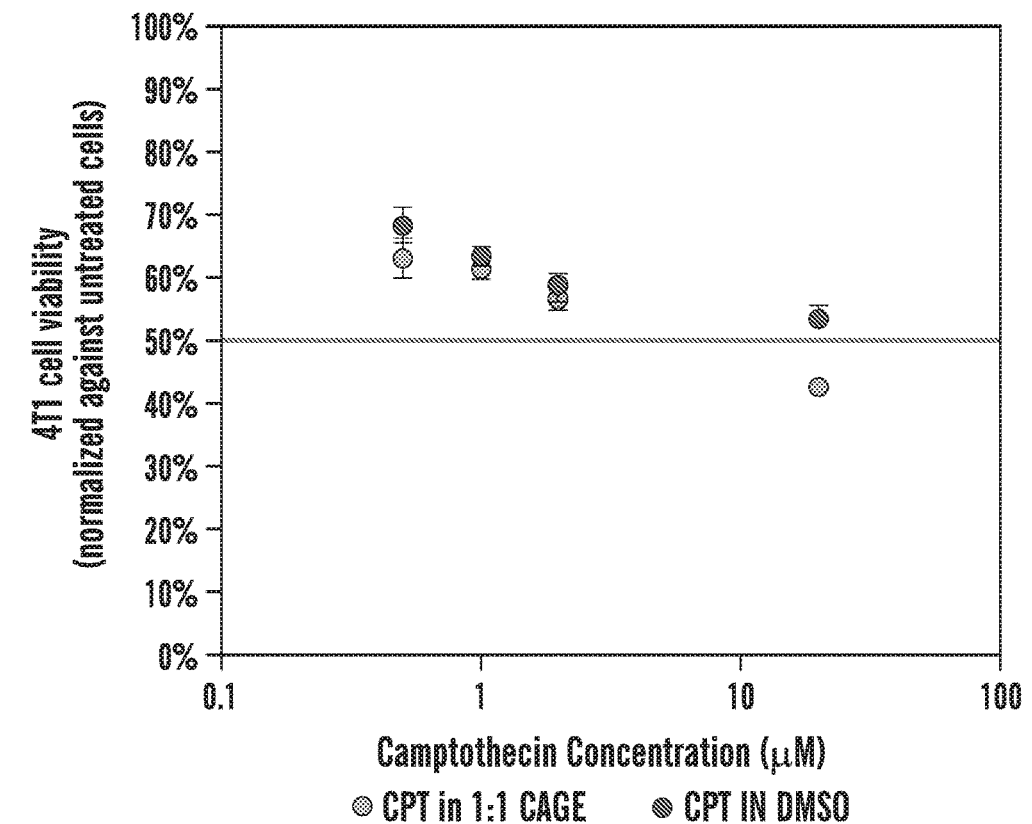
FIG. 11 demonstrates, left—effect of camptothecin (CPT) solubilized in CAGE on 4T1 cells; right—effect of Paclitaxel solubilized in CAGE on 4T1 cells. Both graphs demonstrate that drugs solubilized in CAGE are just as effective as those solubilized in DMSO.
Figure 11:
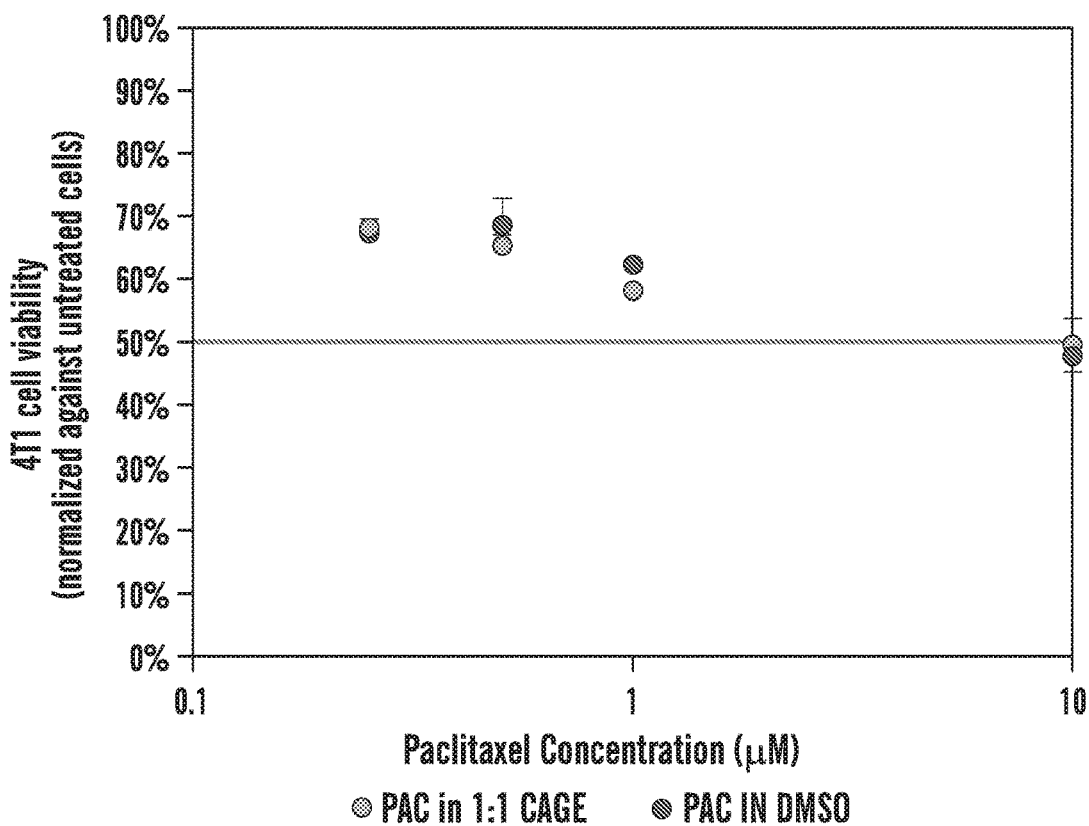

In some embodiments of any of the aspects, the CAGE has a ratio of choline:geranic acid (or geranate) of from about 10:1 to about 1:10. In some embodiments of any of the aspects, the CAGE has a ratio of choline:geranic acid (or geranate) of from 10:1 to 1:10. In some embodiments of any of the aspects, the CAGE has a ratio of choline:geranic acid (or geranate) of from about 5:1 to about 1:5. In some embodiments of any of the aspects, the CAGE has a ratio of choline:geranic acid (or geranate) of from 5:1 to 1:5. In some embodiments of any of the aspects, the CAGE has a ratio of choline:geranic acid (or geranate) of from about 2:1 to about 1:4. In some embodiments of any of the aspects, the CAGE has a ratio of choline:geranic acid (or geranate) of from 2:1 to 1:4. In some embodiments of any of the aspects, the CAGE has a ratio of choline:geranic acid (or geranate) of from about 1:1 to about 1:4. In some embodiments of any of the aspects, the CAGE has a ratio of choline:geranic acid (or geranate) of from 1:1 to 1:4. In some embodiments of any of the aspects, the CAGE has a ratio of choline:geranic acid (or geranate) of about 1:1, 1:2, 1:3, or 1:4. In some embodiments of any of the aspects, the CAGE has a ratio of choline:geranic acid (or geranate) of 1:1, 1:2, 1:3, or 1:4. The Figures depict data collected with CAGE of a ratio of 1:2, except for FIG. 11, which utilized CAGE of a ratio of 1:1. Without wishing to be constrained by theory, compositions with higher ratios of geranic acid and/or geranate display greater hydrophobicity and toxicity while compositions with higher ratios of choline display greater hydrophilicity and are more inert. In some embodiments of any of the aspects, compositions with higher ratios of geranic acid and/or geranate display greater hydrophobicity while compositions with higher ratios of choline display greater hydrophilicity.

In some embodiments of any of the aspects, e.g., when one or more nucleic acid molecules are provided in combination with the CAGE, the ratio of choline:geranic acid (or geranate) is greater than 1:1, e.g., greater than 1:2, from about 1:2 to about 1:4, or from 1:2 to 1:4.

In some embodiments of any of the aspects, the ionic liquid (e.g., CAGE) concentration in the composition or formulation is about 0.1 mM to 20 mM. In some embodiments of any of the aspects, the ionic liquid (e.g., CAGE) concentration in the composition or formulation is about 0.5 mM to 20 mM, 0.5 mM to 18 mM, 0.5 mM to 16 mM, 0.5 mM to 14 mM, 0.5 mM to 12 mM, 0.5 mM to 10 mM, 0.5 mM to 8 mM, 1 mM to 20 mM, 1 mM to 18 mM, 1 mM to 16 mM, 1 mM to 14 mM, 1 mM to 12 mM, 1 mM to 10 mM, 1 mM to 8 mM, 2 mM to 20 mM, 2 mM to 18 mM, 2 mM to 16 mM, 2 mM to 14 mM, 2 mM to 12 mM, 2 mM to 10 mM, 2 mM to 8 mM, 4 mM to 20 mM, 4 mM to 18 mM, 4 mM to 16 mM, 4 mM to 14 mM, 4 mM to 12 mM, 4 mM to 10 mM, 4 mM to 8 mM, 6 mM to 20 mM, 6 mM to 18 mM, 6 mM to 14 mM, 6 mM to 12 mM, 6 mM to 10 mM, 6 mM to 8 mM, 8 mM to 20 mM, 8 mM to 18 mM, 8 mM to 16 mM, 8 mM to 14 mM, 8 mM to 12 mM, 8 mM to 10 mM, 10 mM to 20 mM, 10 mM to 18 mM, 10 mM to 16 mM, 10 mM to 14 mM, 10 mM to 12 mM, 12 mM to 20 mM, 12 mM to 18 mM, 12 mM to 16 mM, 12 mM to 14 mM, 14 mM to 20 mM, 14 mM to 18 mM, 14 mM to 16 mM, 16 mM to 20 mM, 16 mM to 18 mM, or 18 mM to 20 mM. In some embodiments of any of the aspects, the ionic liquid (e.g., CAGE) concentration in the composition or formulation is about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

As used herein, "in combination with" refers to two or more substances being present in the same formulation in any molecular or physical arrangement, e.g, in an admixture, in a solution, in a mixture, in a suspension, in a colloid, in an emulsion. The formulation can be a homogeneous or heterogenous mixture. In some embodiments of any of the aspects, the active compound(s) can be comprised by a superstructure, e.g., nanoparticles, liposomes, vectors, cells, scaffolds, or the like, said superstructure is which in solution, mixture, admixture, suspension, etc., with CAGE.

As used herein, an "active compound" or "active agent" is any agent which will exert an effect on a target cell or organism. The terms "compound" and "agent" refer to any entity which is normally not present or not present at the levels being administered and/or provided to a cell, tissue or subject. An agent can be selected from a group comprising: chemicals; small organic or inorganic molecules; signaling molecules; nucleic acid sequences; nucleic acid analogues; proteins; peptides; enzymes; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the agent is any chemical, entity or moiety, including without limitation synthetic and naturally-occurring non-proteinaceous entities. Agents can be known to have a desired activity and/or property, or can be selected from a library of diverse compounds. Non-limiting examples of active compounds contemplated for use in the methods described herein include small molecules, polypeptides, nucleic acids, chemotherapies/chemotherapeutic compounds, antibodies, antibody reagents, vaccines, a GLP-1 polypeptide or mimetic/analog thereof, and insulin.

A nucleic acid molecule, as described herein, can be a vector, an expression vector, an inhibitory nucleic acid, an aptamer, a template molecule or cassette (e.g., for gene editing), or a targeting molecule (e.g., for CRISPR-Cas technologies), or any other nucleic acid molecule that one wishes to deliver to a cell. The nucleic acid molecule can be RNA, DNA, or synthetic or modified versions thereof.

In one aspect of any of the embodiments, described herein is a method of delivering a nucleic acid molecule to a cell, the method comprising contacting the cell with the nucleic acid molecule in combination with a composition comprising an ionic liquid of Choline And GEranate (CAGE). In some embodiments of any of the aspects, the cell is a cell in a subject and the contacting step comprises administering the nucleic acid molecule in combination with a composition comprising an ionic liquid of Choline And GEranate (CAGE) to the subject. In some embodiments of any of the aspects, the cell is in vitro, in vivo, or ex vivo. In some embodiments of any of the aspects, the cell is eukaryotic. In some embodiments of any of the aspects, the cell is mammalian. In some embodiments of any of the aspects, the cell is an epithelial cell, e.g, an intestinal epithelial cell.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In some embodiments of any of the aspects, the active compound can be a therapeutic compound or drug, e.g., an agent or compound which is therapeutically effective for the treatment of at least one condition in a subject. Therapeutic compounds are known in the art for a variety of conditions, see, e.g., the database available on the world wide web at drugs.com or the catalog of FDA-approved compounds available on the world wide web at catalog.data.gov/dataset/drugsfda-database; each of which is incorporated by reference herein in its entirety.

As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule.

In some embodiments of any of the aspects, the active compound is a hydrophobic molecule, e.g., estradiol, testosterone, imiquimod, corticosterone, paclitaxel, doxorubicin, cisplatin, and/or camptothecin. In some embodiments of any of the aspects, the active compound is a hydrophobic molecule, e.g., estradiol, testosterone, paclitaxel, doxorubicin, cisplatin, and/or camptothecin.

In one aspect of any of the embodiments, described herein is a composition comprising at least one active compound in combination with CAGE. In some embodiments, the pharmaceutical composition comprises CAGE and the one or more active compounds as described herein. In some embodiments, the pharmaceutical composition consists essentially of CAGE and the one or more active compounds as described herein. In some embodiments, the pharmaceutical composition consists of CAGE and the one or more active compounds as described herein. In some embodiments, the pharmaceutical composition consists essentially of an aqueous solution of CAGE and the one or more active compounds as described herein. In some embodiments, the pharmaceutical composition consists of an aqueous solution of CAGE and the one or more active compounds as described herein.

In some embodiments of any of the aspects, a composition as described herein, e.g., a composition comprising CAGE and an active compound, can further comprise a pharmaceutically acceptable carrier. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present disclosure can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

The term "carrier" in the context of a pharmaceutical carrier refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active compound. The term "pharmaceutically acceptable carrier" excludes tissue culture medium.

In some embodiments of any of the aspects, a composition as described herein, e.g, a composition comprising CAGE and an active compound, can be formulated as an oral, subcutaneous, intravenous, intradermal, or parenteral formulation. In some embodiments of any of the aspects, an oral formulation can be a degradable capsule comprising the composition described herein, e.g., a composition comprising CAGE and an active compound.

In some embodiments of any of the aspects described herein, the biological activity of the active compound is improved or stabilized as compared to the activity in the absence of CAGE. In some embodiments of any of the aspects described herein, the ionic liquid (e.g., CAGE) or solvent greatly enhances permeation of insulin across the skin compared to a control insulin where the ionic liquid or solvent is absent.

In one aspect of any of the embodiments, described herein is a method of administering at least active compound to a subject using a catheter wherein the catheter is coated with CAGE. In one aspect of any of the embodiments, described herein is a method of collecting a body fluid by placing the catheter into the body wherein the catheter is coated with CAGE.

In some embodiments, the methods described herein relate to treating a subject having or diagnosed as having a condition with a composition as described herein, e.g., a comprising CAGE and an active compound. Subjects having a condition, e.g., diabetes, can be identified by a physician using current methods of diagnosing diabetes. Symptoms and/or complications of diabetes which characterize these conditions and aid in diagnosis are well known in the art and include but are not limited to, weight loss, slow healing, polyuria, polydipsia, polyphagiam headaches, itchy skin, and fatigue. Tests that may aid in a diagnosis of, e.g. diabetes include, but are not limited to, blood tests (e.g., for fasting glucose levels). A family history of diabetes, or exposure to risk factors for diabetes (e.g. overweight) can also aid in determining if a subject is likely to have diabetes or in making a diagnosis of diabetes.

The compositions and methods described herein can be administered to a subject having or diagnosed as having a condition described herein. In some embodiments, the methods described herein comprise administering an effective amount of compositions described herein, e.g. a composition comprising CAGE and an active compound, to a subject in order to alleviate a symptom of a condition described herein. As used herein, "alleviating a symptom" is ameliorating any marker or symptom associated with a condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active compound, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for blood glucose, among others. The dosage can be determined by a physician and adjusted, as necessary, to suit observed effects of the treatment.

As used herein, "diabetes" refers to diabetes mellitus, a metabolic disease characterized by a deficiency or absence of insulin secretion by the pancreas. As used throughout, "diabetes" includes Type 1, Type 2, Type 3, and Type 4 diabetes mellitus unless otherwise specified herein. The onset of diabetes is typically due to a combination of hereditary and environmental causes, resulting in abnormally high blood sugar levels (hyperglycemia). The two most common forms of diabetes are due to either a diminished production of insulin (in type 1), or diminished response by the body to insulin (in type 2 and gestational). Both lead to hyperglycemia, which largely causes the acute signs of diabetes: excessive urine production, resulting compensatory thirst and increased fluid intake, blurred vision, unexplained weight loss, lethargy, and changes in energy metabolism. Diabetes can cause many complications. Acute complications (hypoglycemia, ketoacidosis, or nonketotic hyperosmolar coma) may occur if the disease is not adequately controlled. Serious long-term complications (i.e. chronic side effects) include cardiovascular disease (doubled risk), chronic renal failure, retinal damage (which can lead to blindness), nerve damage (of several kinds), and microvascular damage, which may cause impotence and poor wound healing. Poor healing of wounds, particularly of the feet, can lead to gangrene, and possibly to amputation. In some embodiments, the diabetes can be Type 2 diabetes. Type 2 diabetes (non-insulin-dependent diabetes mellitus (NIDDM), or adult-onset diabetes) is a metabolic disorder that is primarily characterized by insulin resistance (diminished response by the body to insulin), relative insulin deficiency, and hyperglycemia. In some embodiments, a subject can be pre-diabetic, which can be characterized, for example, as having elevated fasting blood sugar or elevated post-prandial blood sugar.

Glucagon-Like Peptide-1 (GLP-1), is known to reduce food intake and hunger feelings in humans and is an incretin derived from the transcription product of the proglucagon gene that contributes to glucose homeostasis. GLP-1 mimetics are currently being used in the treatment of Type 2 diabetes. Recent clinical trials have shown that these treatments not only improve glucose homeostasis but also succeed in inducing weight loss. As used herein. "GLP-1 polypeptide" refers to the various pre- and pro-peptides and cleavage products of GLP-1, e.g., for human: GLP-1 (1-37) (SEQ ID NO: 2), GLP-1 (7-36) (SEQ ID NO: 3), and GLP-1 (7-37) (SEQ ID NO: 4). In some embodiments, a GLP-1 polypeptide can be GLP-1 (7-36) and/or GLP-1 (7-37) or the correlating polypeptides from a species other than human. Sequences for GLP-1 polypeptides are known in the art for a number of species, e.g. human GLP-1 (NCBI Gene ID: 2641) polypeptides (e.g., NCBI Ref Seq: NP 002045.1; SEQ ID NO: 1) and SEQ ID NOs: 2-4. In some embodiments, a pre or pro-peptide of GLP-1 can be used in the methods or compositions described herein, e.g., a glucagon preproprotein (e.g., SEQ ID NO: 1). Naturally-occurring alleles or variants of any of the polypeptides described herein are also specifically contemplated for use in the methods and compositions described herein.

```
                                                          SEQ ID NO: 1
  1    mksiyfvagl  fvmlvqgswq  rslqdteeks  rsfsasqadp  lsdpdqmned  krhsqgtfts 61    dyskyldsrr  aqdfvqwlmn  tkrnrnniak  rhdeferhae  gtftsdvssy  legqaakefi 121    awlvkgrgrr  dfpeevaive  elgrrhadgs  fsdemntild  nlaardfinw  liqtkitdrk SEQ ID NO: 2
hdeferhae gtftsdvssy legqaakefi awlvkgrg SEQ ID NO: 3
hae gtftsdvssy legqaakefi awlvkgr SEQ ID NO: 4
hae gtftsdvssy legqaakefi awlvkgrg
```

Various GLP-1 mimetics are known in the art and used in the treatment of diabetes. GLP-1 mimetics (or analogues) can include exendin-4 (a Heloderma lizard polypeptide with homology to human GLP-1) and derivatives thereof, GLP-1 analogs modified to be DPP-IV resistant, or human GLP-1 polypeptides conjugated to various further agents, e.g., to extend the half-life. GLP-1 mimetics/analogues can include, e.g., exenatide, lixisenatide, dulaglutide, semaglutide, albiglutide, LY2189265, liraglutide, and taspoglutide. Examples of such molecules and further discussion of their manufacture and activity can be found in the art, e.g., Gupta. Indian J. Endocrinol Metab 17:413-421 (2013); Garber. Diabetes Treatments 41:S279-S284 (2018); US Patent Publication US2009/0181912; and International Patent Publication WO2011/080103, each of which is incorporated by reference herein in its entirety.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL;

high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

In some embodiments of any of the aspects, the composition as described herein, e.g., a composition comprising CAGE in combination with at least one active compound, is administered as a monotherapy, e.g., another treatment for the condition is not administered to the subject.

In some embodiments of any of the aspects, the methods described herein can further comprise administering a second agent and/or treatment to the subject, e.g. as part of a combinatorial therapy, either in the composition described herein, e.g., a composition comprising CAGE in combination with at least one active compound, or as a separate formulation. For example, non-limiting examples of a second agent and/or treatment for treatment of cancer can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation or radiation therapy. Further, the methods of treatment can further include the use of surgical treatments.

In certain embodiments, an effective dose of a composition described herein, e.g, a composition comprising CAGE in combination with at least one active compound, can be administered to a patient once. In certain embodiments, an effective dose a composition described herein, e.g, a composition comprising CAGE in combination with at least one active compound, can be administered to a patient repeatedly. For systemic administration, subjects can be administered a therapeutic amount of a composition described herein, e.g, a composition comprising CAGE in combination with at least one active compound, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, the active compound is insulin and the concentration or dosage of insulin can be from about 1 U/kg to about 20 U/kg. In some embodiments, the active compound is insulin and the concentration or dosage of insulin can be from 1 U/kg to 20 U/kg. In some embodiments, the active compound is insulin and the concentration or dosage of insulin can be less than 20 U/kg. In some embodiments, the active compound is insulin and the concentration or dosage of insulin can be from about 2 U/kg to about 10 U/kg. In some embodiments, the active compound is insulin and the concentration or dosage of insulin can be from 2 U/kg to 10 U/kg. In some embodiments, the active compound is insulin and the concentration or dosage of insulin can be from about 2 U/kg to about 5 U/kg. In some embodiments, the active compound is insulin and the concentration or dosage of insulin can be from 2 U/kg to 5 U/kg. In some embodiments, the active compound is insulin and the concentration or dosage of insulin can be from about 5 U/kg to about 10 U/kg. In some embodiments, the active compound is insulin and the concentration or dosage of insulin can be from 5 U/kg to 10 U/kg. In some embodiments, the active compound is insulin and the concentration or dosage of insulin can be 2 U/kg, 5 U/kg, or 10 U/kg.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active compound. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition described herein, e.g, a composition comprising CAGE in combination with at least one active compound, can be administered over a period of time, such as over a 5 minute, 10 minute, 15 minute, 20 minute, or 25 minute period.

The dosage ranges for the administration of the compositions described herein, according to the methods described herein depend upon, for example, the form of the active compound, its potency, and the extent to which symptoms, markers, or indicators of a condition described herein are desired to be reduced, for example the percentage reduction desired for symptoms or markers. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition described in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of diabetes or cancer. When using an experimental animal model, efficacy of treatment is evidenced when a statistically significant change in a marker is observed.

In vitro and animal model assays are provided herein which allow the assessment of a given dose of a composition described herein, e.g, a composition comprising CAGE in combination with at least one active compound. By way of non-limiting example, the effects of a dose of a composition comprising CAGE in combination with insulin can be assessed by using the mouse models described in the Examples herein.

The incidence of obesity is on the rise and existing treatments, such as diets, have notoriously low long-term success rates. Additional treatments and strategies for reducing obesity or reducing weight gain rates are of critical importance both for addressing obesity itself as well the number of conditions that are caused by or exacerbated by excess weight. As described herein, the inventors have demonstrated that the ionic liquid CAGE (choline and geranate or gernanic acid) reduces the uptake of hydrophobic/lipophilic molecules in the intestine. Accordingly, provided herein are methods of treating obesity and/or reducing weight/weight gain by administering CAGE to a subject in need of such.

Additionally, CAGE is able to safely carry active compounds across the sensitive membranes encountered during oral administration. Accordingly, in some embodiments of any of the aspects, the composition comprising CAGE further comprises an active compound/agent. Accordingly, in some embodiments of any of the aspects, the subject is administered a composition comprising CAGE in combination with an active compound/agent.

In some embodiments of any of the aspects, the active compound is therapeutically effective in treating obesity. In some embodiments of any of the aspects, the active compound is therapeutically effective in treating a disease associated with obesity. In some embodiments of any of the aspects, the active compound is therapeutically effective in treating a disease caused by obesity. In some embodiments of any of the aspects, the active compound is therapeutically effective in treating a disease which causes obesity. In some embodiments of any of the aspects, the active compound is therapeutically effective in treating metabolic syndrome.

In some embodiments of any of the aspects, the active compound is a hydrophobic molecule, e.g., estradiol, testosterone, imiquimod, corticosterone, paclitaxel, doxorubicin, cisplatin, and/or camptothecin. In some embodiments of any of the aspects, the active compound is a hydrophobic molecule, e.g., estradiol, testosterone, corticosterone, paclitaxel, doxorubicin, cisplatin, and/or camptothecin.

In some embodiments of any of the aspects, the composition comprises CAGE. In some embodiments of any of the aspects, the composition consists essentially of CAGE. In some embodiments of any of the aspects, the composition consists of CAGE. In some embodiments of any of the aspects, the composition comprising CAGE is administered as a monotherapy, e.g., another treatment for the condition is not administered to the subject.

In some embodiments of any of the aspects, the composition comprises CAGE and at least one active compound. In some embodiments of any of the aspects, the composition consists essentially of CAGE and at least one active compound. In some embodiments of any of the aspects, the composition consists of CAGE and at least one active compound. In some embodiments of any of the aspects, the composition comprising CAGE and at least one active compound is administered as a monotherapy, e.g., another treatment for the condition is not administered to the subject.

In some embodiments of any of the aspects, a composition comprising CAGE and optionally an active compound can be formulated as an oral, subcutaneous, intravenous, intradermal, or parenteral formulation. In some embodiments of any of the aspects, an oral formulation can be a degradable capsule comprising the composition comprising CAGE and optionally, an active compound.

In some embodiments of any of the aspects, the subject administered a composition comprising CAGE is a subject having, diagnosed as having, or in need of treatment for obesity, excess weight, or prevention of weight gain. In some embodiments, the subject is overweight. The methods described herein comprises methods of treating obesity, reducing weight gain, preventing weight gain, promoting weight loss, and the like. Such methods can, e.g., promote metabolic health, be pursued for aesthetic reasons, and/or prepare patients for surgical interventions which are counterindicated for those with high BMIs or weights. In some embodiments, weight loss can be medically necessary and/or medically indicated, e.g. when the subject is overweight and/or obese. In some embodiments, weight loss can be for cosmetic purposes, e.g. when the subject desires to lose weight whether or not weight loss is medically necessary and/or medically indicated.

The term "obesity" refers to excess fat in the body. Obesity can be determined by any measure accepted and utilized by those of skill in the art. Currently, an accepted measure of obesity is body mass index (BMI), which is a measure of body weight in kilograms relative to the square of height in meters. Generally, for an adult over age 20, a BMI between about 18.5 and 24.9 is considered normal, a BMI between about 25.0 and 29.9 is considered overweight, a BMI at or above about 30.0 is considered obese, and a BMI at or above about 40 is considered morbidly obese. (See, e.g., Gallagher et al. (2000) Am J Clin Nutr 72:694-701.) These BMI ranges are based on the effect of body weight on increased risk for disease. Some common conditions related to high BMI and obesity include cardiovascular disease, high blood pressure (i.e., hypertension), osteoarthritis, cancer, and diabetes. Although BMI correlates with body fat, the relation between BMI and actual body fat differs with age and gender. For example, women are more likely to have a higher percent of body fat than men for the same BMI. Furthermore, the BMI threshold that separates normal, overweight, and obese can vary, e.g. with age, gender, ethnicity, fitness, and body type, amongst other factors. In some embodiments, a subject with obesity can be a subject with a body mass index of at least about 25 kg/m$^2$ prior to administration of a treatment as described herein. In some embodiments, a subject with obesity can be a subject with a body mass index of at least about 30 kg/m$^2$ prior to administration of a treatment as described herein.

In some embodiments of any of the aspects, the subject administered a composition comprising CAGE is a subject having, diagnosed as having, or in need of treatment for a metabolic disorder or metabolic syndrome. The term "metabolic disorder" refers to any disorder associated with or aggravated by impaired or altered glucose regulation or glycemic control, such as, for example, insulin resistance. Such disorders include, but are not limited to obesity; excess adipose tissue; diabetes; fatty liver disease; non-alcoholic fatty liver disease; metabolic syndrome; dyslipidemia; hypertension; hyperglycemia; and cardiovascular disease. "Metabolic syndrome", which is distinct from metabolic disorder, refers to a combination of medical disorders that, when occurring together, increase the risk of developing cardiovascular disease and diabetes. A number of definitions of metabolic syndrome have been established, e.g by the American Heart Association and the International Diabetes Foundation. As but one example, the WHO defines metabolic syndrome as the presence of any one of diabetes mellitus, impaired glucose tolerance, impaired fasting glucose or insulin resistance and two of the following: blood pressure equal to or greater than 140/90 mmHg, dyslipidemia, central obesity, and microalbuminuria. In some embodiments, the metabolic disorder can be selected from the group consisting of: obesity; excess adipose tissue; diabetes; and cardiovascular disease.

In some embodiments, the methods described herein relate to treating a subject having or diagnosed as having a condition with a composition comprising CAGE and an active compound. Subjects having a condition, e.g., diabetes, can be identified by a physician using current methods of diagnosing diabetes. Symptoms and/or complications of diabetes which characterize these conditions and aid in diagnosis are well known in the art and include but are not limited to, weight loss, slow healing, polyuria, polydipsia, polyphagiam headaches, itchy skin, and fatigue. Tests that may aid in a diagnosis of, e.g. diabetes include, but are not limited to, blood tests (e.g., for fasting glucose levels). A family history of diabetes, or exposure to risk factors for diabetes (e.g. overweight) can also aid in determining if a subject is likely to have diabetes or in making a diagnosis of diabetes.

In some embodiments of any of the aspects, a subject treated in accordance with the present methods is a subject not having or not diagnosed as having diabetes. In some embodiments of any of the aspects, a subject treated in accordance with the present methods is a subject not administered insulin. In some embodiments of any of the aspects, the composition comprising CAGE does not comprise insulin. In some embodiments of any of the aspects, the composition comprising CAGE does not comprise another pharmaceutically active ingredient and/or another agent which is therapeutically effective in treating diabetes.

The uptake of many active compounds, e.g., pharmaceutically active compounds, can be improved by delivering the compounds in solvents. However, such approaches are often unsuitable for in vivo use because most such solvents demonstrate toxic side effects and/or act as irritants to the point of delivery. Described herein are methods and compositions which can provide low toxicity with improved delivery kinetics.

As described herein, the inventors have discovered that at 50 mM or greater, salts displaying a surprising and significant increase in their ability to cross cells/cell membranes, and to increase the ability of any associated molecules to do the same. Accordingly, described herein are methods of drug delivery which relate to the use of high molarity salts, e.g., salts at greater than 0.05 M.

As used herein, "salt" refers to an ionic compound comprising at least one cation and at least one anion, such that compound is electrically neutral. The salt can comprise inorganic or organic, polyatomic or monatomic ions. The salt can be an alkali salt. In some embodiments of any of the aspects, the salt is an ionic liquid.

In some embodiments of any of the aspects, the salt is at a concentration of at least 0.01% w/v. In some embodiments of any of the aspects, the salt is at a concentration of at least 0.05% w/v. In some embodiments of any of the aspects, the salt is at a concentration of at least 0.1% w/v. In some embodiments of any of the aspects, the salt is at a concentration of at least 0.2% w/v, at least 0.3% w/v, at least 0.4% w/v, at least 0.5% w/v, at least 1% w/v or greater.

In some embodiments of any of the aspects, the salt is at a concentration of at least 20 mM. In some embodiments of any of the aspects, the salt is at a concentration of at least about 20 mM. In some embodiments of any of the aspects, the salt is at a concentration of at least 25 mM. In some embodiments of any of the aspects, the salt is at a concentration of at least about 25 mM. In some embodiments of any of the aspects, the salt is at a concentration of at least 50 mM. In some embodiments of any of the aspects, the salt is at a concentration of at least about 50 mM. In some embodiments of any of the aspects, the salt is at a concentration of at least 100 mM, 500 mM, 1 M, 2 M, 3 M or greater. In some embodiments of any of the aspects, the salt is at a concentration of at least about 100 mM, 500 mM, 1 M, 2 M, 3 M or greater.

In some embodiments of any of the aspects, the salt is at a concentration of from about 50 mM to about 4 M. In some embodiments of any of the aspects, the salt is at a concentration of from 50 mM to 4 M. In some embodiments of any of the aspects, the salt is at a concentration of from about 500 mM to about 4 M. In some embodiments of any of the aspects, the salt is at a concentration of from 500 mM to 4 M. In some embodiments of any of the aspects, the salt is at a concentration of from about 1 M to about 4 M. In some embodiments of any of the aspects, the salt is at a concentration of from 1 M to 4 M. In some embodiments of any of the aspects, the salt is at a concentration of from about 2 M to about 4 M. In some embodiments of any of the aspects, the salt is at a concentration of from 2 M to 4 M.

In some embodiments of any of the aspects, e.g., when one or more nucleic acid molecules are provided in combination with the CAGE, the ratio of choline:geranic acid (or geranate) is greater than 1:1, e.g., greater than 1:2, from about 1:2 to about 1:4, or from 1:2 to 1:4.

In one aspect of any of the embodiments, described herein is a composition comprising at least one active compound in combination with the salt (e.g., at a concentration of 0.05M or higher). In some embodiments, the pharmaceutical composition comprises the salt and the one or more active compounds as described herein. In some embodiments, the pharmaceutical composition consists essentially of the salt and the one or more active compounds as described herein. In some embodiments, the pharmaceutical composition consists of the salt and the one or more active compounds as described herein. In some embodiments, the pharmaceutical composition consists essentially of an aqueous solution of the salt and the one or more active compounds as described herein. In some embodiments, the pharmaceutical composition consists of an aqueous solution of the salt and the one or more active compounds as described herein.

In some embodiments, the salt is an anhydrous salt, e.g., an ionic liquid not diluted or dissolved in water. In some embodiments, the salt is provided as an aqueous solution.

In some embodiments of any of the aspects, a composition comprising the salt (e.g., at a concentration of 0.05 M or higher) and an active compound can further comprise a pharmaceutically acceptable carrier.

In some embodiments of any of the aspects, a composition comprising the salt (e.g. a concentration of 0.05 M or higher) and an active compound can be formulated as an oral, subcutaneous, intravenous, intradermal, or parenteral formulation. In some embodiments of any of the aspects, an oral formulation can be a degradable capsule comprising the composition comprising the salt and an active compound.

In another embodiment, the drug may continue to remain soluble in the salt, e.g., CAGE, even after local diffusion of CAGE and lead to quick and enhanced delivery into circulation. Subcutaneous delivery often necessitates multiple doses or controlled release formulations. Such approaches are not necessarily performed due to any concern about timing per se, but rather done to ensure that the entire dose is received prior to degradation of the active compound. Bolus administration is often ineffective because the active compound degrades or is metabolized before the full dose can extert an effect. Due the ability of CAGE to stabilize active compounds, such approaches are unnecessary, i.e., the total desired dose can be delivered as a single administration without the need for controlled release mechanisms.

In one aspect of any of the embodiments, described herein is a method of treating a disease in a subject in need thereof by administering to the subject an active compound in combination with the salt by into the affected tissue by injection. In some embodiments, the affected tissue is tissue comprising diseased cells. In some embodiments, the affected tissue is tissue displaying symptoms of the disease. Non-limiting examples of suitable affected tissues include tumor tissue, fat tissue, adipose tissue, a wart, or the like. In some embodiments of any of the aspects, suitable affected tissues include tumor tissue, fat tissue, adipose tissue, or the like.

In some embodiments of any of the aspects the disease is a disease arising from tissue growth, e.g., unwanted, aberrant, or pathological tissue growth. A disease arising from tissue growth can be any disease caused by or characterized by, a rate of tissue growth, location of tissue growth, or pattern/structure of tissue growth which differs from what is normal for that tissue type in a healthy subject. Non-limiting examples of such diseases are tumors, cancer, fat/obesity, warts, and/or hyperplasia. In some embodiments of any of the aspects, such diseases are tumors, cancer, fat/obesity, and/or hyperplasia.

In some embodiments of any of the aspects described herein, the biological activity of the active compound is improved or stabilized as compared to the activity in the absence of the salt at a concentration of greater than 0.05M. In some embodiments of any of the aspects described herein, the salt (e.g., CAGE) or solvent greatly enhances permeation of insulin across the skin compared to a control insulin where the ionic liquid or solvent is absent.

In one aspect of any of the embodiments, described herein is a method of administering at least active compound to a subject using a catheter wherein the catheter is coated with the salt at a concentration of greater than 0.05M. In one aspect of any of the embodiments, described herein is a method of collecting a body fluid by placing the catheter into the body wherein the catheter is coated with the salt at a concentration of greater than 0.05M.

In some embodiments, the methods described herein relate to treating a subject having or diagnosed as having a condition with a composition comprising the salt at a concentration of greater than 0.05M and an active compound. Subjects having a condition, e.g., diabetes, can be identified by a physician using current methods of diagnosing diabetes. Symptoms and/or complications of diabetes which characterize these conditions and aid in diagnosis are well known in the art and include but are not limited to, weight loss, slow healing, polyuria, polydipsia, polyphagiam headaches, itchy skin, and fatigue. Tests that may aid in a diagnosis of, e.g. diabetes include, but are not limited to, blood tests (e.g., for fasting glucose levels). A family history of diabetes, or exposure to risk factors for diabetes (e.g. overweight) can also aid in determining if a subject is likely to have diabetes or in making a diagnosis of diabetes.

In some embodiments of any of the aspects, the composition comprising the salt at a concentration of greater than 0.05M is administered as a monotherapy, e.g., another treatment for the condition is not administered to the subject. In such embodiments, the salt or a component thereof can have therapeutic efficacy for the disease being treated.

In some embodiments of any of the aspects, the composition comprising the salt at a concentration of greater than 0.05M in combination with at least one active compound described herein is administered as a monotherapy, e.g., another treatment for the condition is not administered to the subject.

In some embodiments of any of the aspects, the methods described herein can further comprise administering a second agent and/or treatment to the subject, e.g. as part of a combinatorial therapy, either in the composition comprising the salt at a concentration of greater than 0.05M in combination with at least one active compound or as a separate formulation.

In certain embodiments, an effective dose of a composition comprising the salt at a concentration of 0.05M or greater in combination with at least one active compound as described herein can be administered to a patient once. In certain embodiments, an effective dose of a composition comprising the salt at a concentration of 0.05M or greater in combination with at least one active compound can be administered to a patient repeatedly. For systemic administration, subjects can be administered a therapeutic amount of a composition comprising the salt at a concentration of 0.05M or greater in combination with at least one active compound such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, the active compound is insulin and the concentration or dosage of insulin can be from about 1 U/kg to about 20 U/kg. In some embodiments, the active compound is insulin and the concentration or dosage of insulin can be from 1 U/kg to 20 U/kg. In some embodiments, the active compound is insulin and the concentration or dosage of insulin can be less than 20 U/kg. In some embodiments, the active compound is insulin and the concentration or dosage of insulin can be from about 2 U/kg to about 10 U/kg. In some embodiments, the active compound is insulin and the concentration or dosage of insulin can be from 2 U/kg to 10 U/kg. In some embodiments, the active compound is insulin and the concentration or dosage of insulin can be from about 2 U/kg to about 5 U/kg. In some embodiments, the active compound is insulin and the concentration or dosage of insulin can be from 2 U/kg to 5 U/kg. In some embodiments, the active compound is insulin and the concentration or dosage of insulin can be from about 5 U/kg to about 10 U/kg. In some embodiments, the active compound is insulin and the concentration or dosage of insulin can be from 5 U/kg to 10 U/kg. In some embodiments, the active compound is insulin and the concentration or dosage of insulin can be 2 U/kg, 5 U/kg, or 10 U/kg.

Enzyme inhibitors are a treatment option for a number of conditions, including diabetes, where, for example, insulin-degrading enzyme inhibitors, ACE inhibitors, and alpha-glucosidase inhibitors have all been explored as therapeutic approaches. Safe, effective enzyme inhibitors are therefore of interest in the treatment of a number of conditions. In one aspect of any of the embodiments, described herein is a method of treating diabetes, ulcers, cancer, or fibrosis in a subject in need thereof, the method comprising administering to the subject a composition comprising the ionic liquid Choline And GEranate (CAGE). In some embodiments, the composition comprising CAGE does not comprise a further therapeutically active agent.

The ionic liquid CAGE (choline and geranate or gernanic acid) is safe for use orally and/or parenterally but without the negative side effects typically observed for most solvents. Indeed, solvents as a class present a general problem of toxicity, thus "solvent exposure" being a commonly used medical term meant to encompass the hazards of contact with one or more solvents. Solvent exposure generally, as well as exposure to select individual solvents, has been demonstrated to contribute to the etiology of a number of conditions. In light of this, the safety profile of CAGE is particularly surprising and unexpected, particularly via the oral and parenteral administration routes, which bypass many of the body's natural defenses.

In one aspect of any of the embodiments, described herein is a composition comprising CAGE. In some embodiments, the composition is a pharmaceutical composition comprising CAGE. In some embodiments, the pharmaceutical composition consists essentially of CAGE. In some embodiments, the pharmaceutical composition consists of CAGE. In some embodiments, the pharmaceutical composition consists essentially of an aqueous solution of CAGE. In some embodiments, the pharmaceutical composition consists of an aqueous solution of CAGE.

In some embodiments of any of the aspects, a composition comprising CAGE can be formulated as an oral, subcutaneous, intravenous, intradermal, or parenteral formulation. In some embodiments of any of the aspects, an oral formulation can be a degradable capsule comprising the composition comprising CAGE. In certain embodiments, an effective dose of a composition comprising CAGE can be administered to a patient once. In certain embodiments, an effective dose of a composition comprising CAGE can be administered to a patient repeatedly.

In one aspect of any of the embodiments, described herein is a method of treating a disease in a subject in need thereof by administering to the subject CAGE into the affected tissue by injection. In some embodiments, the affected tissue is tissue comprising diseased cells. In some embodiments, the affected tissue is tissue displaying symptoms of the disease. Non-limiting examples of suitable affected tissues include tumor tissue, fat tissue, adipose tissue, a wart, or the like. In some embodiments of any of the aspects, affected tissues include tumor tissue, fat tissue, adipose tissue or the like. The disease can be, e.g., cancer, fibrosis, or ulcers.

Fibrotic conditions benefit from the production and/or maintenance of the extracellular matrix by reducing the accumulation of scar tissue in favor of extracellular matrix. As used herein, "fibrosis" refers to the formation of fibrous tissue as a reparative or reactive process, rather than as a normal constituent of an organ or tissue. Fibrosis is characterized by fibroblast accumulation and collagen deposition in excess of normal deposition in any particular tissue. Fibrosis can occur as the result of inflammation, irritation, or healing. A subject in need of treatment for a fibrotic condition is any subject having, or diagnosed as having, or at risk of having a fibrotic condition. Non-limiting examples of fibrotic conditions include, but are not limited to pulmonary fibrosis; scarring; scarring of the skin; trauma; a wound; chronic wounds (e.g. as in diabetes patients), corneal defects; corneal ulceration; corneal wounds; diabetic ulcer; ulcer; sepsis; arthritis; idiopathic pulmonary fibrosis; cystic fibrosis; cirrhosis; endomyocardial fibrosis; mediastinal fibrosis; myelofibrosis; retroperitoneal fibrosis; progressive massive fibrosis; nephrogenic systemic fibrosis; Crohn's disease; keloid; scleroderma; systemic sclerosis; arthrofibrosis; adhesive capsulitis; lung fibrosis; liver fibrosis; kidney fibrosis; heart fibrosis; vascular fibrosis; skin fibrosis; eye fibrosis; bone marrow fibrosis; asthma; sarcoidosis; COPD; emphysema; nschistomasomiasis; cholangitis; diabetic nephropathy; lupus nephritis; postangioplasty aterial restenosis; atherosclerosis; burn scarring; hypertrophic scarring; nephrogenic fibrosing dermatopathy; postcataract surgery; proliferative vitreoretinopathy; Peyronie's disease; Duputren's contracture; dermatomyositis; and graft versus host disease.

As used herein, "ulcer" refers to a break or disruption of a bodily membrane. In some embodiments, the ulcer can be caused by inflammation and/or necrosis of the affected tissue. Ulcers can be skin ulcers (e.g., pressure ulcers, diabetic ulcers, ulcerative dermatitis, and the like), a corneal ulcer, an oral ulcer, a peptic ulcer, a venousucler, a stress ulcer, or ulcerative colitis.

In some embodiments of any of the aspects, the composition comprising CAGE is administered as a monotherapy, e.g., another treatment for the condition is not administered to the subject.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of conditions described herein. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. the activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

In some embodiments of any of the aspects, a variant can be a polypeptide having at least 90%, at least 95%, at least 98% or greater sequence homology to one of the reference sequences provided herein and retaining the wild-type activity of that reference sequence, e.g., incretin activity. In some embodiments of any of the aspects, a variant can be a polypeptide having at least 90%, at least 95%, at least 98% or greater sequence homology to one of the naturally-occurring reference sequences provided herein and retaining the wild-type activity of that reference sequence, e.g., incretin activity. In some embodiments of any of the aspects, a variant can be a naturally-occurring polypeptide having at least 90%, at least 95%, at least 98% or greater sequence homology to one of the reference sequences provided herein and retaining the wild-type activity of that reference sequence, e.g., incretin activity.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., cDNA. Suitable RNA can include, e.g., mRNA.

As used herein, "inhibitory nucleic acid" refers to a nucleic acid molecule which can inhibit the expression of a target, e.g., double-stranded RNAs (dsRNAs), inhibitory RNAs (iRNAs), and the like.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or activity of a target. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art.

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO] mCH3, O(CH2).nOCH3, O(CH2)nNH2, O(CH2) nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a recombinant vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. a condition or disease described herein. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "effective amount" means an amount of a composition sufficient to provide at least some amelioration of the symptoms associated with the condition. In one embodiment, the "effective amount" means an amount of a composition would decrease the markers or symptoms of the condition in a subject having the condition.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" or "comprises" is used in reference to methods and compositions, and respective component(s) thereof, that are essential to the invention, yet open to the inclusion of unspecified elements, whether essential or not. As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An ionic liquid or solvent comprising a group of salts with organic cation and organic/inorganic anion.
2. The ionic liquid or solvent of paragraph 1, wherein the organic cation and organic/inorganic anion are choline and geranate or geranic acid respectively.
3. The ionic liquid or solvent of paragraph 1 or 2, wherein the ionic liquid or solvent exists as a liquid below 100° C.
4. The ionic liquid or solvent of paragraph 1, 2, or 3, wherein the ionic liquid or solvent exists as a liquid at room temperature.
5. The ionic liquid or solvent of any one of paragraphs 1-4, wherein the ionic liquid or solvent greatly enhanced permeation of insulin across the skin compared to a control insulin where the ionic liquid or solvent is absent.
6. A composition comprising an ionic liquid of any one of paragraphs 1-5, and an insulin.
7. The composition of paragraph 6 further comprising a pharmaceutically acceptable carrier.
8. The composition of paragraph 6 or 7, wherein the composition is formulated as an oral formulation.
9. A composition comprising an ionic liquid comprising choline and geranate, and insulin.
10. The composition of paragraph 9 further comprising a pharmaceutically acceptable carrier.
11. An oral formulation comprising an ionic liquid comprising choline and geranate, insulin and pharmaceutically acceptable carrier.

12. An insulin formulation for oral delivery comprising an ionic liquid of any one of paragraphs 1-5.
13. The insulin formulation for oral delivery of paragraph 12 further comprising a pharmaceutically acceptable carrier.
14. A method for oral delivery of a therapeutic drug comprising admixing an ionic liquid of any one of paragraphs 1-5 with a therapeutic drug and orally administering the admixture to a subject.
15. The method of paragraph 14, wherein the admixture is an oral formulation.
16. A method of treatment of diabetes comprising orally administering an oral formulation of insulin comprising choline and geranate, and insulin, wherein the choline and geranate forms an ionic liquid solvent.
17. The composition of any one of paragraphs 6-10, or the formulation of any one of paragraphs 11-13, or the method of any one of paragraphs 14-16, wherein the ionic liquid concentration in the composition or formulation is about 0.1 mM to 20 mM.
18. The composition of any one of paragraphs 6-10, or the formulation of any one of paragraphs 11-13, or the method of any one of paragraphs 14-16, wherein the ionic liquid concentration in the composition or formulation is about 0.5 mM to 20 mM, 0.5 mM to 18 mM, 0.5 mM to 16 mM, 0.5 mM to 14 mM, 0.5 mM to 12 mM, 0.5 mM to 10 mM, 0.5 mM to 8 mM, 1 mM to 20 mM, 1 mM to 18 mM, 1 mM to 16 mM, 1 mM to 14 mM, 1 mM to 12 mM, 1 mM to 10 mM, 1 mM to 8 mM, 2 mM to 20 mM, 2 mM to 18 mM, 2 mM to 16 mM, 2 mM to 14 mM, 2 mM to 12 mM, 2 mM to 10 mM, 2 mM to 8 mM, 4 mM to 20 mM, 4 mM to 18 mM, 4 mM to 16 mM, 4 mM to 14 mM, 4 mM to 12 mM, 4 mM to 10 mM, 4 mM to 8 mM, 6 mM to 20 mM, 6 mM to 18 mM, 6 mM to 14 mM, 6 mM to 12 mM, 6 mM to 10 mM, 6 mM to 8 mM, 8 mM to 20 mM, 8 mM to 18 mM, 8 mM to 16 mM, 8 mM to 14 mM, 8 mM to 12 mM, 8 mM to 10 mM, 10 mM to 20 mM, 10 mM to 18 mM, 10 mM to 16 mM, 10 mM to 14 mM, 10 mM to 12 mM, 12 mM to 20 mM, 12 mM to 18 mM, 12 mM to 16 mM, 12 mM to 14 mM, 14 mM to 20 mM, 14 mM to 18 mM, 14 mM to 16 mM, 16 mM to 20 mM, 16 mM to 18 mM, or 18 mM to 20 mM.
19. The composition of paragraph 17, wherein the ionic liquid concentration in the composition is about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM or about 20 mM.

Some embodiments of the technology described herein can be defined according to any of the following numbered paragraphs:

1. A method of oral delivery of at least one active compound, the method comprising orally administering the active compound in combination with a composition comprising an ionic liquid of Choline And GEranate (CAGE).
2. A method of delivery of at least one active compound, the method comprising subcutaneously, intradermally or intravenously administering the active compound in combination with CAGE.
3. A method of delivery of at least one active compound, the method comprising administering the active compound in combination with CAGE to a mucus membrane.
4. The method of paragraph 3, wherein the mucus membrane is nasal, oral, or vaginal.
5. A method of parenteral delivery of at least one active compound, the method comprising parenterally administering the active compound in combination with CAGE.
6. The method of paragraph 5, wherein the administration comprises delivery to a tumor.
7. A method of treating a disease in a subject in need thereof by administering to the subject an active compound in combination with CAGE by into the affected tissue by injection.
8. The method of paragraph 7, wherein the disease is cancer, fat, wart, hyperplasia or any other disease arising from tissue growth.
9. The method of any of paragraphs 1-8, wherein CAGE is at a concentration of at least 0.1% w/v.
10. The method of any of paragraphs 1-9, wherein the CAGE comprises a ratio of choline:geranic acid or geranate of from about 2:1 to about 1:10.
11. The method of any of paragraphs 1-9, wherein the CAGE comprises a ratio of choline:geranic acid or geranate of from about 1:1 to about 1:4.
12. The method of any of paragraphs 1-9, wherein the CAGE comprises a ratio of choline:geranic acid or geranate of from about 1:2 to about 1:4.
13. The method of any of paragraphs 1-12, wherein the ionic liquid's anion comprises geranate and/or geranic acid.
14. The method of any of paragraphs 1-13, wherein the active compound in combination with CAGE is administered once.
15. The method of any of paragraphs 1-14, wherein the active compound in combination with CAGE is administered in multiple doses.
16. The method of any of paragraphs 1-15, wherein the active compound comprises a nucleic acid molecule.
17. The method of any of paragraphs 1-15, wherein the active compound comprises a small molecule.
18. The method of any of paragraphs 1-15, wherein the active compound comprises a polypeptide.
19. The method of any of paragraphs 1-15, wherein the active compound comprises an antibody or antibody reagent.
20. The method of any of paragraphs 1-19, wherein the active compound comprises a chemotherapeutic compound.
21. The method of any of paragraphs 1-20, wherein the active compound comprises insulin.
22. The method of paragraph 21, wherein the insulin is provided at a dosage of 1-20 mg/kg.
23. A composition comprising an active compound in combination with CAGE.
24. The composition of paragraph 23, wherein CAGE is at a concentration of at least 0.1% w/v.
25. The composition of any of paragraphs 23-24, wherein the CAGE comprises a ratio of choline:geranic acid or geranate of from about 2:1 to about 1:10.
26. The composition of any of paragraphs 23-24, wherein the CAGE comprises a ratio of choline:geranic acid or geranate of from about 1:1 to about 1:4.
27. The composition of any of paragraphs 23-24, wherein the CAGE comprises a ratio of choline:geranic acid or geranate of from about 1:2 to about 1:4.
28. The composition of any of paragraphs 23-27, wherein the active compound comprises a nucleic acid molecule.

29. The composition of any of paragraphs 23-27, wherein the active compound comprises a small molecule.
30. The composition of any of paragraphs 23-27, wherein the active compound comprises a polypeptide.
31. The composition of any of paragraphs 23-27, wherein the active compound comprises an antibody or antibody reagent.
32. The composition of any of paragraphs 23-31, wherein the active compound comprises a chemotherapeutic compound.
33. The composition of any of paragraphs 23-32, wherein the active compound comprises insulin.
34. The composition of paragraph 233, wherein the insulin is provided at a dosage of 1-20 mg/kg.
35. The composition of any of paragraphs 23-34, further comprising a further pharmaceutically acceptable carrier.
36. The composition of any of paragraphs 23-35, formulated as an oral, subcutaneous, or parenteral formulation.
37. The composition of any of paragraphs 23-36, formulated for administration to a mucus membrane.
38. The composition of paragraph 37, wherein the mucus membrane is nasal, oral, or vaginal.
39. The composition of paragraph 36, wherein the oral formulation is a degradable capsule comprising the combination of the active compound and CAGE.
40. The composition of any of paragraphs 23-39, wherein the biological activity of the active compound is improved or stabilized as compared to the activity in the absence of CAGE.
41. The method or composition of any of paragraphs 1-40, wherein the combination of the active compound and CAGE is an admixture.
42. The method or composition of any of paragraphs 1-40, wherein the combination of the active compound and CAGE comprises nanoparticles comprising the active compound, the nanoparticles in solution or suspension in a composition comprising CAGE.
43. A method of delivering a nucleic acid molecule to a cell, the method comprising contacting the cell with the nucleic acid molecule in combination with a composition comprising an ionic liquid of Choline And GEranate (CAGE).
44. The method of paragraph 43, wherein the cell is a cell in a subject and the contacting step comprises administering the nucleic acid molecule in combination with a composition comprising an ionic liquid of Choline And GEranate (CAGE) to the subject.
45. The method of any of paragraphs 43-44, wherein the nucleic acid molecule comprises a vector, an expression vector, or an inhibitory nucleic acid molecule.
46. The method of any of paragraphs 43-45, wherein CAGE is at a concentration of at least 0.1% w/v.
47. The method of any of paragraphs 43-46 wherein the CAGE comprises a ratio of choline:geranic acid or geranate of from about 2:1 to about 1:10.
48. The method of any of paragraphs 43-46, wherein the CAGE comprises a ratio of choline:geranic acid or geranate of from about 1:1 to about 1:4.
49. The method of any of paragraphs 43-46, wherein the CAGE comprises a ratio of choline:geranic acid or geranate of from about 1:2 to about 1:4.
50. The method of any of paragraphs 43-49, wherein the ionic liquid's anion comprises geranate and/or geranic acid.
51. The method of any of paragraphs 43-50, wherein the combination of the nucleic acid molecule and CAGE is an admixture.
52. The method of any of paragraphs 43-50, wherein the combination of the nucleic acid molecule and CAGE comprises nanoparticles comprising the nucleic acid molecule, the nanoparticles in solution or suspension in a composition comprising CAGE.
53. At least one active compound in combination with a composition comprising an ionic liquid of Choline And GEranate (CAGE) for use in oral delivery, delivery to a mucus membrane, parenteral delivery, or the treatment of a disease.
54. The combination of paragraph 53, wherein the mucus membrane is nasal, oral, or vaginal.
55. The combination of paragraph 53, wherein the parenteral administration comprises delivery to a tumor.
56. The combination of paragraph 53, wherein the treatment comprises injection of the composition to the affected tissue.
57. The combination of paragraph 56, wherein the disease is cancer, fat, wart, hyperplasia or any other disease arising from tissue growth.
58. The combination of any of paragraphs 53-57, wherein CAGE is at a concentration of at least 0.1% w/v.
59. The combination of any of paragraphs 53-58, wherein the CAGE comprises a ratio of choline:geranic acid or geranate of from about 2:1 to about 1:10.
60. The combination of any of paragraphs 53-59, wherein the CAGE comprises a ratio of choline:geranic acid or geranate of from about 1:1 to about 1:4.
61. The combination of any of paragraphs 53-59, wherein the CAGE comprises a ratio of choline:geranic acid or geranate of from about 1:2 to about 1:4.
62. The combination of any of paragraphs 53-61, wherein the ionic liquid's anion comprises geranate and/or geranic acid.
63. The combination of any of paragraphs 53-62, wherein the active compound in combination with CAGE is administered once.
64. The combination of any of paragraphs 53-62, wherein the active compound in combination with CAGE is administered in multiple doses.
65. The combination of any of paragraphs 53-64, wherein the active compound comprises a nucleic acid molecule.
66. The combination of any of paragraphs 53-65, wherein the active compound comprises a small molecule.
67. The combination of any of paragraphs 53-65, wherein the active compound comprises a polypeptide.
68. The combination of any of paragraphs 53-65, wherein the active compound comprises an antibody or antibody reagent.
69. The combination of any of paragraphs 53-65, wherein the active compound comprises a chemotherapeutic compound.
70. The combination of any of paragraphs 53-65, wherein the active compound comprises insulin.
71. The combination of paragraph 70, wherein the insulin is provided at a dosage of 1-20 mg/kg.

EXAMPLES

Example 1: Choline-Geranate as a Highly Effective Solvent for Oral Delivery of Insulin Abbreviations AUC Area under the curve
BSM Basal seeding medium CAGE Choline and geranate
CD Circular dichroism
CLSM Confocal laser scanning microscopy
DAPI 4',6-Diamidino-2-Phenylindole, Dihydrochloride
DMEM Dulbecco modified eagle medium
DMSO Dimethyl sulfoxide
F Bioavailability
FBS Fetal bovine serum
FITC Fluorescein isothiocyanate
GIT Gastrointestinal tract
IC50 Half maximal inhibitory concentration
IJ Intrajejunal
$K_{el}$ Elimination rate constant
MTT 3-(4,5-dimethylthiazol-2-yl)-2-diphenyltetrazolium bromide
PBS Phosphate buffered saline
P/S Penicillin and streptomycin
RT Room temperature
SQ Subcutaneous
$t^{1/2}$ Half-life
TEER Trans epithelial electrical resistance With the rise in diabetes mellitus cases worldwide and lack of patient adherence to glycemia management using injectable insulin, there is an urgent need for the development of efficient oral insulin formulations. However, the gastrointestinal tract presents a formidable barrier to oral delivery of biologics. Here we report the development of a highly effective oral insulin formulation using Choline and Geranate (CAGE) ionic liquid. In vivo, insulin-CAGE demonstrated exceptional pharmacokinetic bioavailability of 51% and pharmacodynamic bioavailability of 66% after jejunal administration in rats. Low insulin doses (3-10 U/kg) brought about a significant decrease in blood glucose levels, which were sustained for longer periods (up to 12 h), unlike subcutaneously injected insulin. When 10 U/kg insulin-CAGE was orally delivered in enterically coated capsules using an oral gavage, a sustained decrease in blood glucose of up to 45% was observed. The formulation exhibited high biocompatibility and was stable for 2 months at room temperature and for at least 4 months under refrigeration. Taken together, the results indicate that CAGE is a promising oral delivery excipient and should be further explored for oral delivery of insulin and other biologics that are currently marketed as injectables.

The oral route of drug administration is preferred over injections due to its ease of administration, high patient compliance and low manufacturing costs. However, due to various gastrointestinal barriers to drug absorption, it is unsuitable for the delivery of biologics. For example, insulin, is an indispensable medication for Type 1 diabetes management. It is currently administered as a subcutaneous injection, but is associated with lack of patient adherence due to its invasiveness. Orally delivered insulin could significantly enhance patient compliance and it closely mimics the physiological path of pancreatic insulin. Oral/pancreatic insulin is transported to the liver via the portal vein where 80% is retained and the rest reaches systemic circulation, creating up to 3-fold higher insulin concentration in the portal vein compared to systemic circulation. This portal-peripheral insulin gradient is disrupted when insulin is injected subcutaneously due to a higher systemic insulin concentration compared to that in the portal vein (only ~20%) which disrupts the liver's fine balance between glycogen storage and glucose output, often resulting in hyperglycemia, which when treated with higher insulin dose, can lead to hypoglycemia.

The pursuit for an oral insulin product began many decades ago. Several strategies have been developed to overcome the gastrointestinal barriers to oral absorption of biologics, however, no formulation has successfully cleared all clinical hurdles and therefore no oral insulin products are currently commercially available. Products that have completed or are currently in phase II clinical trials include enterically coated capsules with additives to improve oral insulin uptake (Capsulin™ by Diabetology Ltd and ORMD-0801 by Oramed Ltd), hepatic directed liposomal insulin (HDV-Insulin by Diasome Pharmaceuticals Inc.), polyethylene glycol (PEG) conjugated insulin (IN-105 by Biocon Ltd.), insulin-proinsulin-c-peptide in Oshadi carrier (Oshadli Icp by Oshadi drug administration Ltd) and long-acting insulin analog tablets using gastrointestinal permeation enhancer technology (GIPET 1 by Novo Nordisk).

In addition, many products require multi-step formulation procedures, various additives or chemical modification of the protein, which have their own shortcomings. With the emerging global diabetes epidemic, there is a sense of urgency to develop safe, effective and easily scalable oral insulin products.

We have developed an ionic liquid (IL)-based oral formulation of insulin and determined its safety, efficacy and long-term stability. Ionic liquids consist of organic/inorganic salts with melting points below 100° C. and have been widely used in various novel chemical and pharmaceutical technologies. For the present work, we utilized a room temperature stable choline and geranate (CAGE) deep eutectic solvent that had earlier demonstrated remarkable efficacy in transdermal delivery of antibiotics and insulin. Insulin was dispersed in CAGE in a single step process and its safety and efficacy was evaluated both in vitro and in vivo as well as its storage stability. The study demonstrates an unprecedented improvement in oral bioavailability of insulin with excellent oral efficacy, biocompatibility and long-term stability.

Determination of FITC-Insulin Transport Across Intestinal Monolayers.

We designed a 5 h long transport experiment of FITC-insulin across Caco-2 monolayers using 10 mM CAGE or saline. In the study insulin-CAGE treated cells demonstrated significantly higher transport from the onset in comparison to insulin-saline treated group (FIG. 1). FITC-insulin transport steadily increased with time for both groups, and throughout the study, an at least 3 times higher transport of insulin was observed across all time points in monolayers treated with CAGE compared to insulin-saline treated cells. At the end of study at 5 h, FITC-insulin transport amounted to 30% in insulin-CAGE treated cells while it was 10% for insulin-saline treated cells.

Figure 2A:
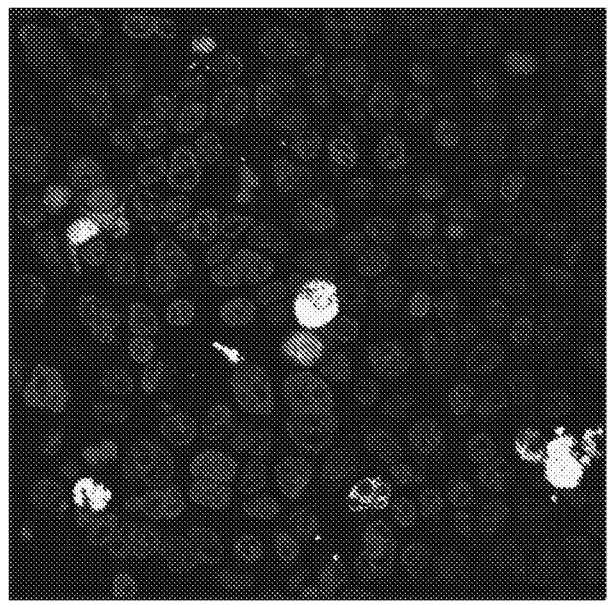
FIGS. 2A-2B depict representative confocal micrograph images of transwell membranes covered with a monolayer of Caco-2 cells and incubated for 5 h with FITC-insulin dispersed in (FIG. 2A) saline and (FIG. 2B) 10 mM CAGE. Images were taken at 60× magnification. The images show overlap of DAPI labeled nucleus (blue color) and FITC-insulin (green color).
Figure 2B:
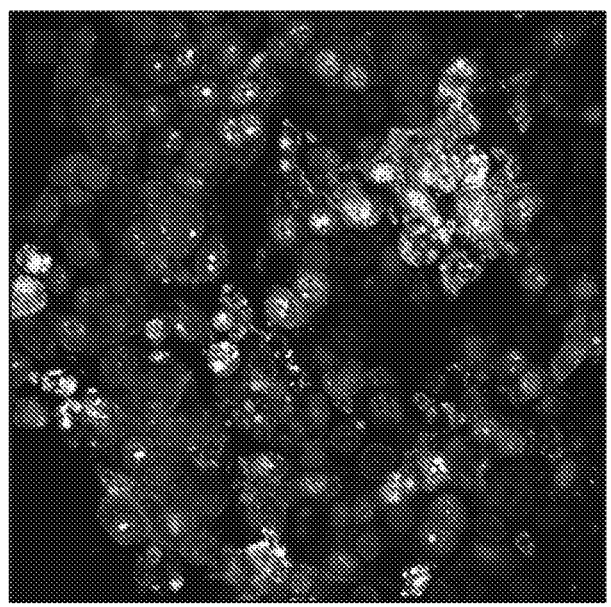

These results were corroborated through confocal imaging of transwell membranes at the end of the study. The images clearly showed higher uptake of FITC-insulin by cells that were incubated with insulin-CAGE when compared to insulin-saline (FIGS. 2A-2B).

Figure 3:
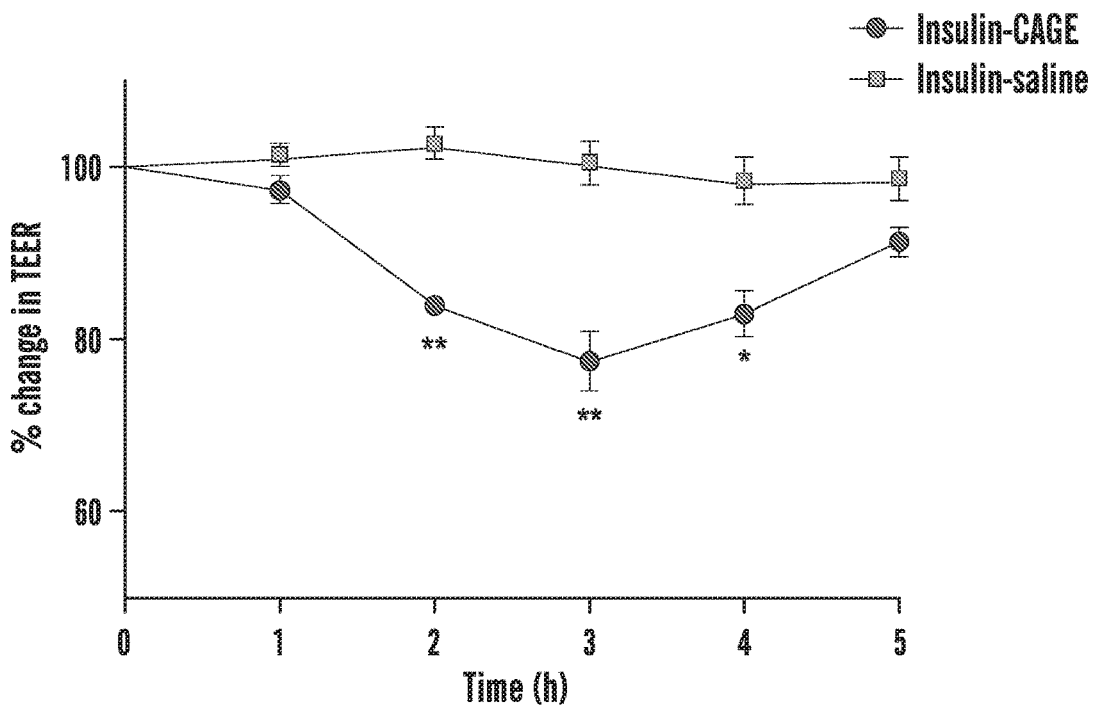
FIG. 3 depicts the effect on tight junction integrity in Caco-2 cells upon treatment with CAGE. Data represented as mean±S.E. (n=6); (* p<0.01; **p<0.001)

TEER was measured to determine the tight junction integrity in Caco-2 cells upon treatment with CAGE. In insulin-saline treated cells, TEER remained close to 100% of original value for the first 3 h and decreased only by 2.5% to 98.5±2.64% by the end of study at 5 h (FIG. 3). However, in insulin-CAGE treated cells, TEER decreased significantly at 2 and 3 h to 88.35±0.86 and 77.43±3.48%, respectively. Beyond 3 h, TEER began to rise and reached 82.94±2.64% of the initial value at 4 h and finally to 91.3±1.73% at 5 h which was not significantly different from insulin-saline treated cells. These changes in TEER brought about by CAGE suggests that CAGE temporarily opens up the intestinal tight junctions and aids insulin transport across the cells. However, besides transient opening of tight junctions, there may be multiple mechanisms that come into play to assist the transport of insulin across these cells by CAGE, which remains to be elucidated.

In Vivo Efficacy of Insulin-CAGE Upon Intrajejunal Administration.

Figure 4:
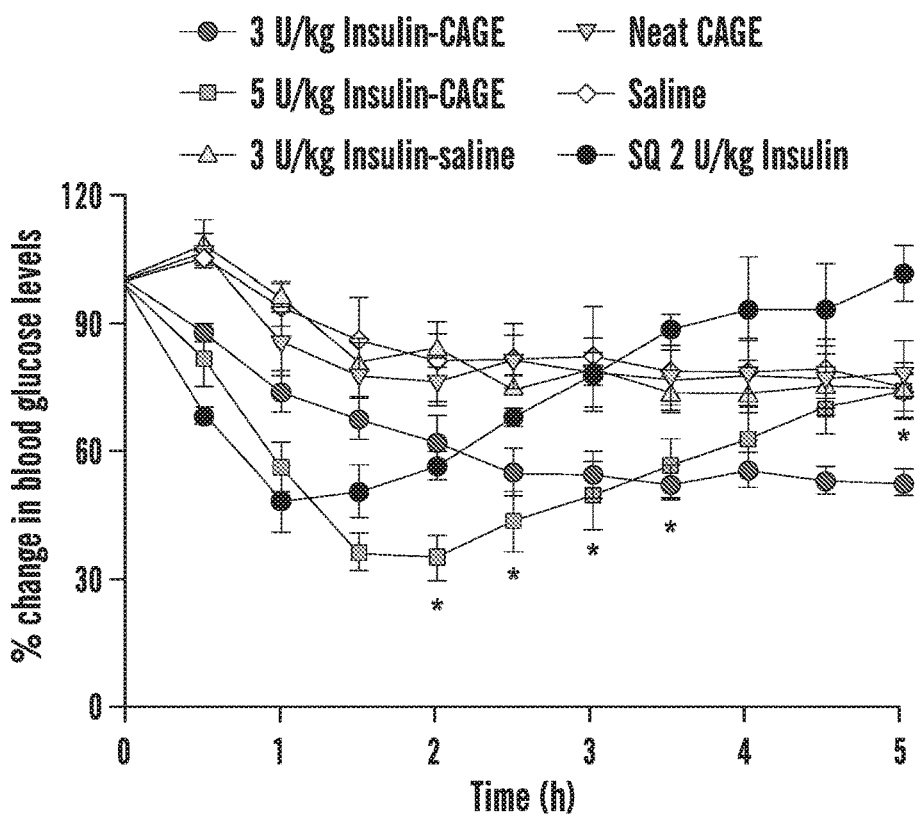
FIG. 4 depicts the efficacy of Insulin-CAGE in lowering blood glucose levels upon intrajejunal administration in non-diabetic rats. Data represented as mean±S.E. (n=6). A significantly higher (p<0.05) efficacy was noted in the efficacy of 5 U/kg insulin-CAGE treated rats from 2-3.5 h and at 5 h compared to subcutaneously administered 2 U/kg insulin (represented by *).

To gauge the efficacy of insulin-CAGE in lowering blood glucose levels, 3-5 U/kg insulin was dispersed in CAGE along with its controls and administered to anesthetized rats intrajejunally, followed by blood glucose monitoring every 0.5 h for a total of 5 h (FIG. 4). In rats administered with 3 U/kg insulin-CAGE, the blood started dropping steadily from 0.5 till it reached 55% of its initial value (55.37±5.64%) in 2.5 h. Beyond this point, blood glucose drop plateaued and reached 53% of initial value by the end of the study at 5 h (53.12±3.16%). The group treated with 5 U/kg insulin-CAGE showed a sharp decrease in blood glucose levels that culminated in ~65% drop within 1.5 and 2 h (36.73±4.46 and 35.37±5.25% respectively). The blood glucose levels increased thereafter as typically observed in non-diabetic rats subjected to rapid drop in blood glucose levels due to the body's glucose homeostasis mechanisms kicking in. At the end of 5 h the blood glucose level was about 74% of initial level (73.93±5.72%). The rats that were injected with 2 U/kg insulin subcutaneously also showed a similar pattern of blood glucose drop as 5 U/kg insulin-CAGE intrajejunal administration. However, the extent of blood glucose drop was lower than intrajejunally administered 5 U/kg insulin-CAGE. A maximum drop of 51% was observed in 1 h (48.76±7.55% of initial level) which rapidly recovered to 100% at the end of the study at 5 h (101.61±6.69%). No significant difference in the efficacy between the subcutaneously administered insulin and 5 U/kg insulin-CAGE was noted in the earlier time points. However, as clearly seen in the FIG. 6, CAGE significantly sustained the action of insulin till the end of study. Similar sustained bioactivity of insulin was also noted for 3 U/kg insulin-CAGE intrajejunal administration. Other formulation controls such as neat CAGE, saline or 3 U/kg insulin-saline intrajejunal administration did not bring about a rapid drop in blood glucose levels as observed in the aforementioned groups. In all these control groups, blood glucose lowered slowly (most likely due to continued fasting) to about 25% of initial levels in 5 h.

Figure 5:
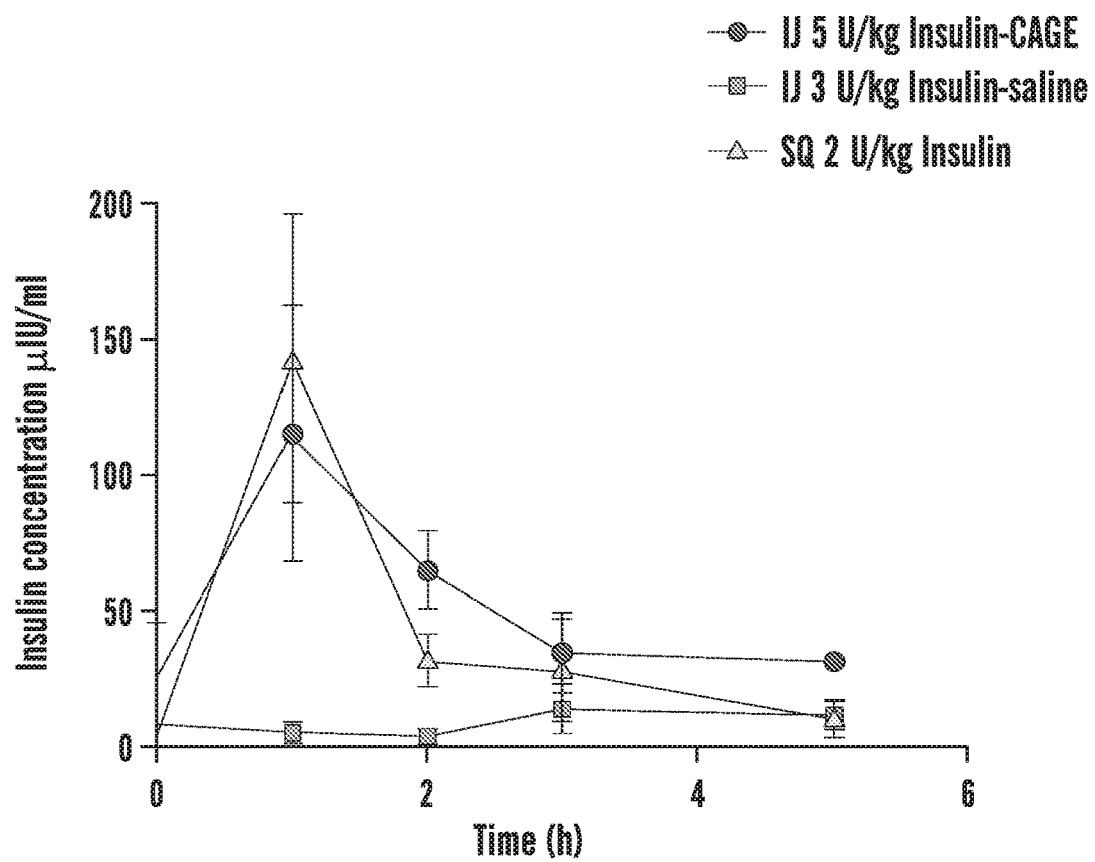
FIG. 5 depicts the efficacy of CAGE in enhancing the oral bioavailability of insulin. Data represented as mean±S.E. (n=4).

The pharmacokinetics of insulin absorption and elimination was determined by measuring serum insulin levels at different time points (FIG. 5). Insulin concentration rapidly increased within an hour after subcutaneous injection of 2 U/kg insulin and intrajejunal administration of 5 U/kg insulin-CAGE, and subsequently dropped and followed a similar pattern in elimination. On the other hand, serum insulin concentration hardly increased for intrajejunally administered 3 U/kg insulin-saline. The pharmacokinetic parameters calculated using serum insulin concentrations showed that the elimination half-life of intrajejunally administered insulin-CAGE was about two times higher than SQ insulin (Table 1). The oral bioavailability of 5 U/kg IJ Insulin-CAGE thus calculated was found to be 50.6%.

TABLE 1

Pharmacokinetic parameters of insulin-CAGE given intrajejunally and insulin solution subcutaneously administered

| Formulation | $K_{el}$ (h$^{-1}$) | $t^{1/2}$ (h) | $AUC_{total}$ (μIU · h/ml) | % F |
|---|---|---|---|---|
| Insulin SQ | 0.58 | 1.2 | 237.6 | |
| Insulin-CAGE | 0.32 | 2.2 | 300.6 | 50.6 |

In our study, a jejunal bioavailability of 51% was obtained, which is also the one of the highest that has been seen amongst other oral insulin formulations. It is also to be noted that elimination half-life of the insulin-CAGE was almost two-fold higher than subcutaneously injected insulin, indicating a more sustained efficacy.

In Vivo Efficacy of Insulin-CAGE Delivered Orally in Capsules.

Figure 6:
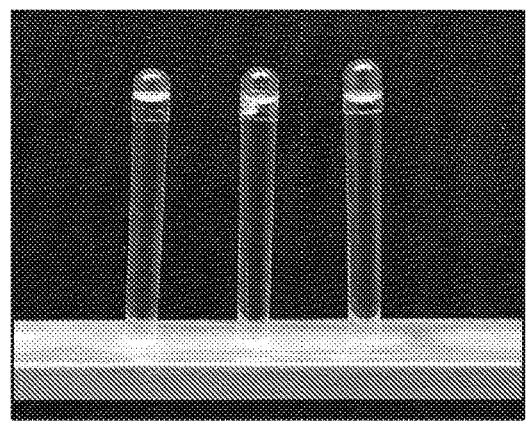
FIG. 6 depicts a picture of CAGE placed inside elongated size 9 capsules for oral administration

The considerable efficacy of CAGE in enhancing oral bioavailability of insulin upon intrajejunal administration, prompted us to investigate whether similar efficacy could be achieved using insulin-CAGE orally delivered in capsules. To this end, we placed 10 U/kg insulin-CAGE and its controls in elongated size 9 capsules as illustrated in FIG. 6 and administered them to rats fasted overnight using an oral gavage.

Figure 7:
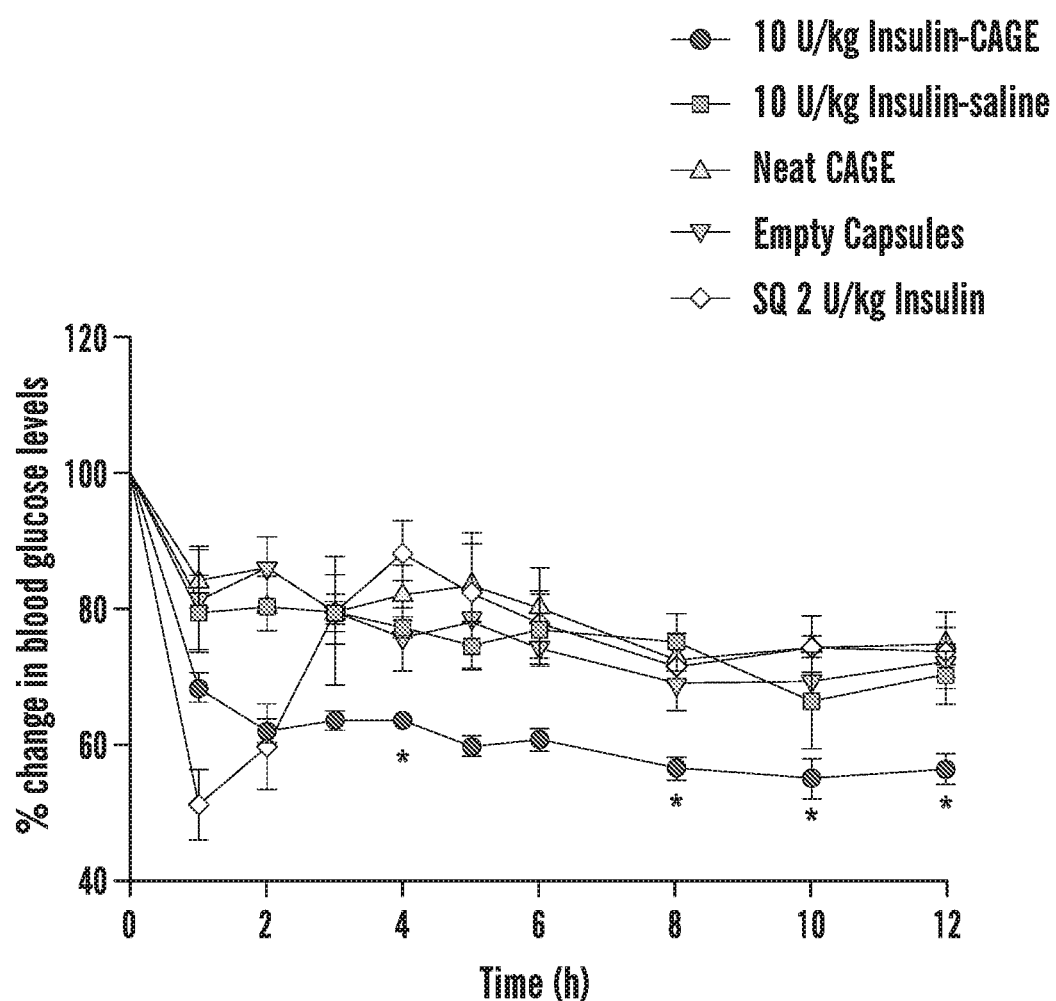
FIG. 7 depicts the in vivo efficacy of insulin-CAGE orally administered in capsules. Data represented as mean±S.E. (n=6). A significantly higher (p<0.05) efficacy of CAGE-insulin was observed at various time points (represented as *) compared to subcutaneously administered insulin.
Figure 8A:
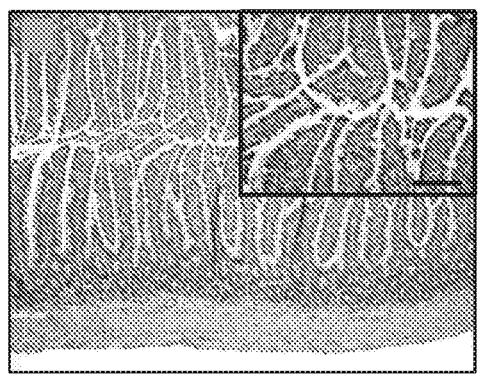
FIGS. 8A-8E depict photomicrographs of hematoxylin and eosin staining of small intestine tissue sections.
Figure 8B:
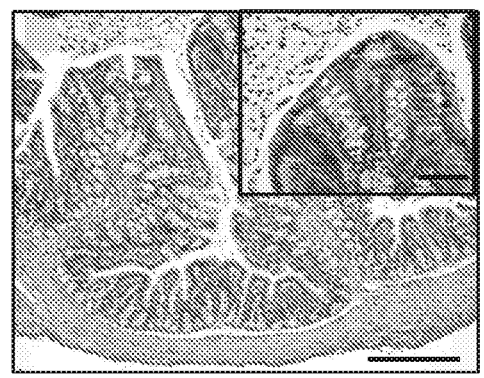
Figure 8C:
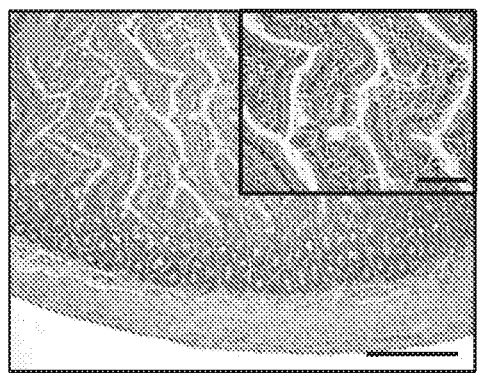
Figure 8D:
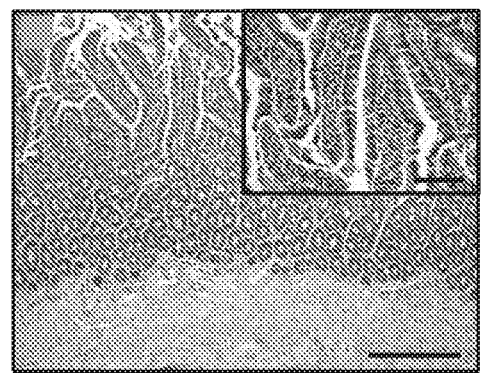
Figure 8E:
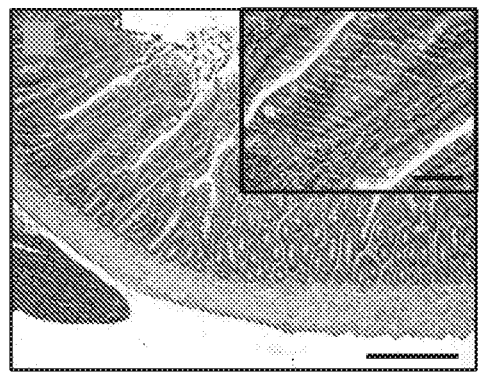

The group treated with 10 U/kg insulin-CAGE demonstrated a rapid drop in blood glucose levels at 1 and 2 h after onset of study (68.58±2.12 and 62.32±1.58% of initial level respectively) (FIG. 7). Beyond this point, blood glucose dropped slowly but steadily to up to around 56% of initial level at 12 h (56.66±2.31%). In comparison, subcutaneous administration of 2 U/kg insulin led to a sharp 50% drop in blood glucose levels (51.43±5.25%) in 1 h, after which it rose steadily to about 88% in 4 h. Thereafter, blood glucose levels dropped in a pattern similar to formulation controls of neat CAGE, empty capsules and insulin-saline. When these controls were orally administered, a slow and steady decrease in blood glucose levels were observed (most likely due to continuous fasting) with time, ending in about 25% decrease at 12 h. It is to be noted that unlike subcutaneously administered insulin and in line with intrajejunal administration, CAGE led to significantly sustained action of insulin starting from 4 h till the end of study at 12 h.

Histological Analysis of Intestine after Intrajejunal and Oral Administration of CAGE.

Histological examination showed no remarkable difference in morphology of small intestinal tissue amongst rats treated with CAGE or saline (FIGS. 8A-8E). The intestinal tissues were collected either 5 h after intrajejunal administration or 12 h after oral administration and showed no significant structural damage to the small intestine tissues. Particularly, fingerlike villi are presents in all the tissue. The results clearly indicated the excellent biocompatibility of CAGE with intestine, thereby validating its suitability for oral administration.

Secondary Structure of Insulin in CAGE.

Figure 9:
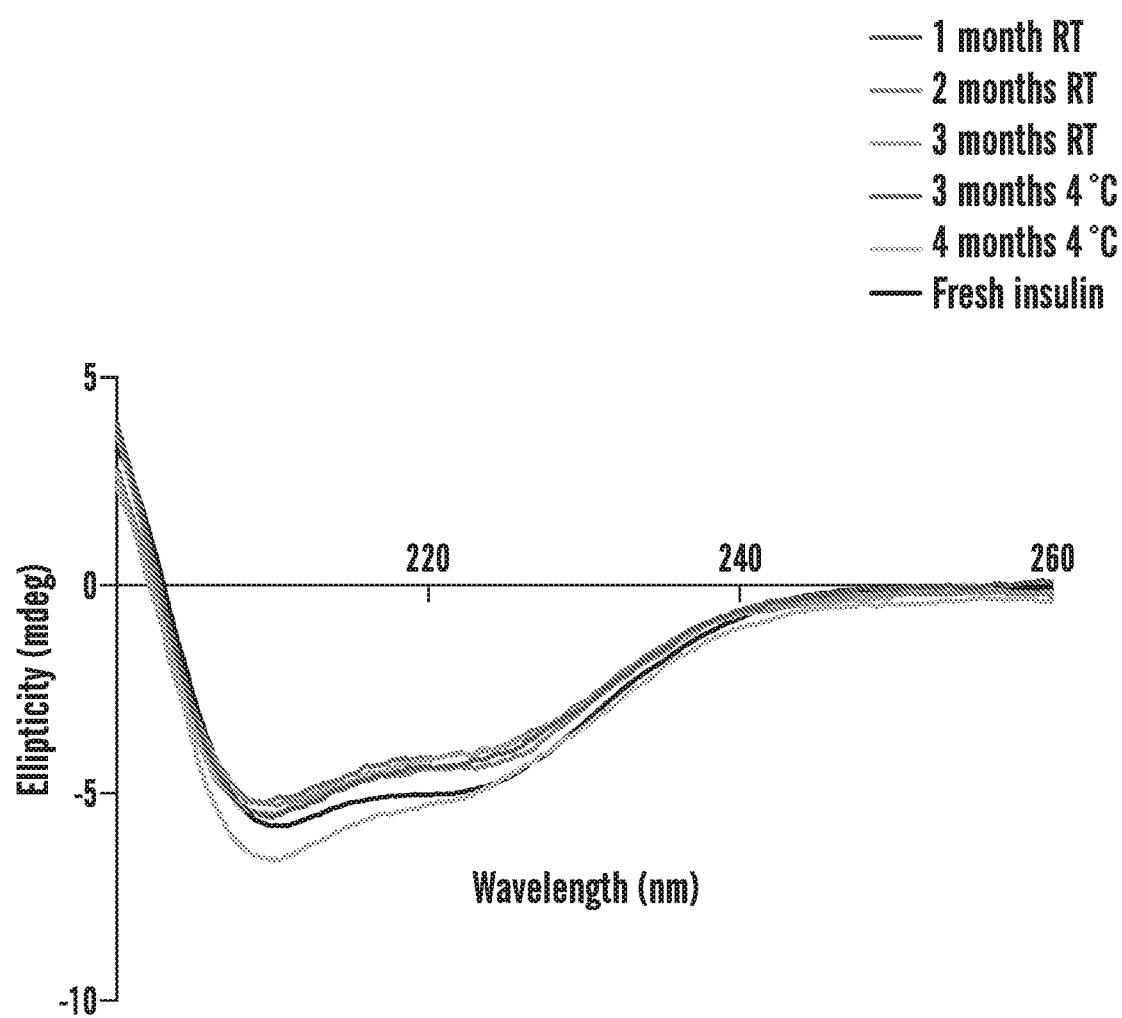
FIG. 9 depicts circular dichroism spectra of insulin isolated from CAGE at different months. Insulin was dispersed in CAGE and stored at RT (25° C.) or under refrigeration at 4° C. for up to 4 months.

Insulin has an inherent alpha-helical conformation which is essential for its receptor binding, hence bioactivity. Previous studies have demonstrated that insulin retains its alpha-helical conformation in CAGE after being stored at room temperature (RT, 25° C.) for 17 h [Banerjee et al, AHM, 2017]. However, it is not known whether the conformation is preserved when insulin is dispersed in CAGE for longer periods of time. To this end, we stored Insulin-CAGE at RT (away from direct sunlight) or under refrigeration at 4° C. and evaluated the secondary structure every month for a period of 4 months using CD. Results showed the presence of double negative troughs at around 207 and 222 nm, which is a typical representation of an alpha-helix in a CD graph (FIG. 9). No difference in the shape or degree of ellipticity was noticed between fresh insulin and that stored for up to 3 months at RT or up to 4 months under refrigeration. The result suggested that CAGE helps retain the stability of insulin for extended periods of time which was subsequently confirmed through bioactivity assessment in vivo. It is to be noted that in general, lyophilized regular insulin is stable at room temperature for up to 3-4 weeks while insulin solution stored at 4° C. is stable for only 2-7 days (see, e.g., the documentation available on the world wide web at prospecbio.com/Insulin Human).

Confirmation of Stability of Insulin in CAGE Through In Vivo Bioactivity Assessment.

Figure 10:
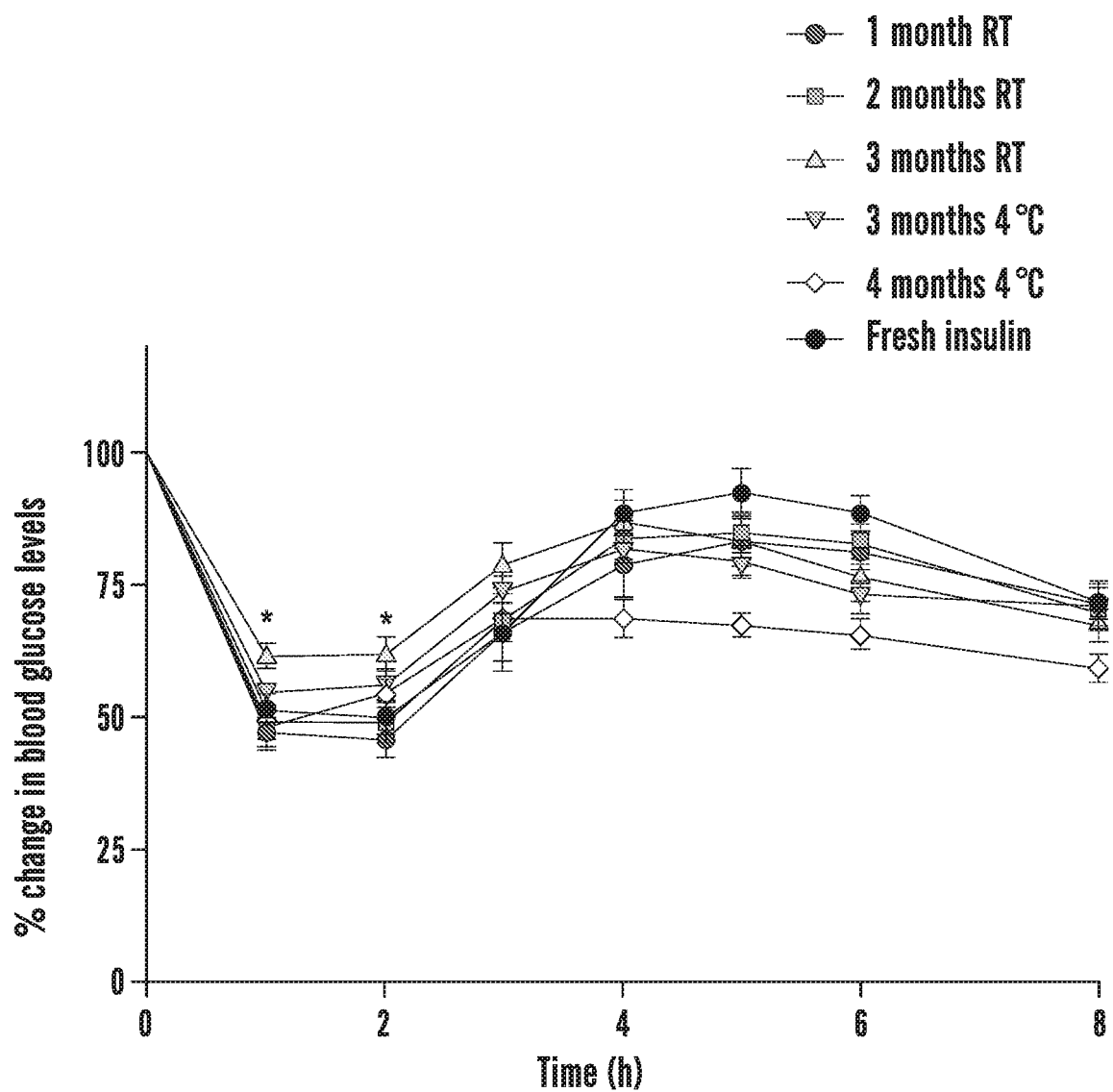
FIG. 10 depicts the efficacy of insulin isolated from CAGE at different time points in reducing blood glucose levels in non-diabetic rats. A statistically significant difference (p<0.05) in bioactivity between freshly prepared insulin and insulin-CAGE stored at RT (25° C.) for 3 months was noted at 1 and 2 h after administration (represented as *). All data represented as mean±S.E. (n=6).

The encouraging results obtained in CD stability studies, prompted us to evaluate the biological activity of insulin in non-diabetic rats, to confirm the stability results. For this purpose, rats that were fasted overnight were subcutaneously injected with 1 U/kg insulin (isolated from CAGE and re-suspended in sterile saline) and blood glucose was monitored for a period of 8 h (FIG. 10). Freshly prepared insulin solution (insulin in saline) brought about a 50% drop in blood glucose levels (50.73±2.47%) in 1 h that was retained in the next hour (49.59±4.4%). Blood glucose levels thereafter rose to about 92% of original level (92.05±4.8%) in 5 h that slowly declined again to about 30% of initial value as a result of continuous fasting. In comparison, insulin isolated from CAGE stored at various temperatures and at different time points followed a similar pattern and showed similar drop in blood glucose levels at 1 and 2 h after injection with no significant difference in percent drop compared to fresh insulin. However, a significantly attenuated efficacy was observed for insulin stored at RT for 3 months. In 1 and 2 h after insulin injection an only 38% drop in blood glucose level was noted (61.57±2.38% and 61.98±3.19% respectively) in this group, indicating that insulin loses some of its bioactivity after 2 months of storage at RT. However, insulin stored at 4° C. with CAGE, did not show any loss in bioactivity even after 4 months of storage. This clearly illustrates that CAGE is an excellent solvent for long-term storage of insulin. Further studies will be required to determine the maximum time length of stability of insulin in CAGE at 4° C.

Discussion

Over the past few decades, the prevalence of diabetes mellitus has grown steadily so much so that it is now being referred to as the 'epidemic of the century' (1). A rise in diabetes mellitus cases has been reported in every country with the most rapid growth in low and middle-income countries and largest prevalence in Middle East and North African region (1-3). According to a recent World Health Organization report, diabetes was responsible for 1.5 million deaths globally in 2012 with an additional 3.2 million deaths due to hyperglycemia-associated co-morbidities (3). In the United States, 30.3 million people (about 9.4% of population) were reported suffering from the disease in 2015 and 1.5 million new cases are diagnosed each year (4). Current recommendations for management of the disease include insulin therapy alone or in combination with oral hypoglycemics such as metformin (5). Individuals on insulin therapy alone often require either administration of intermediate-acting insulin two times a day or long-acting insulin once a day (5). Insulin is not available in the clinics as an oral pill and is exclusively administered as a subcutaneous injection. However, despite its effectiveness in the management of hyperglycemia and mitigating risks of neuropathy, nephropathy and retinopathy, injectable insulin has lower patient compliance due to pain, interference with daily activities and embarrassment, resulting in intentional omission and poor long-term glycemic control in as much as 60% of patients (6, 7). This leads to higher hemoglobin A1C levels and increased hospitalization due to diabetes associated complications (6). To circumvent this issue, MannKind Corporation developed an inhalable rapid-acting insulin formulation Afrezza® for post-prandial glycemia management, however associated pulmonary risks such as higher incidences of lung cancer and diabetic ketoacidosis, decreased lung functions and higher risk of development of acute bronchospasm in patients with chronic lung disease may deter patients from switching to inhalation insulin therapy (8). Given the exponential growth and magnitude of diabetes, it is imperative to develop an insulin therapy that would appeal to patients and avoid formulation based adverse effects.

Oral delivery enjoys a high patient compliance but is not suitable for delivery of macromolecules such as protein or peptide drugs. This is due to the fact that orally delivered drugs need to traverse through the acidic environment of stomach that can degrade protein/peptide drugs. This can be avoided by encapsulating them in enteric or other protective coated systems. However, upon release in the intestine from their protective casings, peptide/protein drugs are pitched into the proteolytic milieu of the intestine where they are easily cleaved into smaller amino acids units by resident enzymes. If a proportion of the drug escapes proteolysis, its absorption through the intestinal mucus layer and enterocytes into the blood circulation as an intact molecule is nearly impossible. Oral insulin absorption is further impeded due to erratic GI transit time and lack of specific insulin uptake mechanisms in the intestine (9). Any perturbation in insulin structure during GI transit may lead to significant denaturation and loss in biological activity. Therefore, not surprisingly, protein and peptide drugs have negligible oral bioavailability of less than 1%, a stark divergence from injectable formulations where 100% of the dose is available for pharmacological activity (10). Several researchers have attempted to resolve the perennial problem of low oral bioavailability of insulin by modifying insulin molecules, encapsulating it in novel carriers, using enteric coatings, absorption enhancers or proteolytic inhibitors. Some examples include using PLGA (poly[lactic-co-glycolic acid]) based nanoparticles for oral insulin delivery. Pan et al. obtained a pharmacological bioavailability of 10.3% using 10 U/kg insulin loaded in PLGA nanoparticles while Cui and co-workers obtained an oral bioavailability of 3.68 and 6.27% using 20 U/kg insulin placed in PLGA and PLGA-55 nanoparticles respectively (11, 12). Sarmento et al used chitosan-dextran nanoparticles to encapsulate insulin and observed a pharmacological bioavailability of 5.6 and 3.4% after placing 50 and 100 U/kg insulin respectively in the particles (13). Alginate-chitosan nanoparticles improved oral bioavailability of insulin to 6.8 and 3.4% for 50 and 100 U/kg insulin doses respectively (14). Zhang and co-workers encapsulated 50 U/kg insulin in solid lipid nanoparticles (SLN) and wheat germ agglutinin modified SLN and obtained pharmacological bioavailabilities of 4.46 and 6.08% respectively (15). In the same vein, Ansari et al. reported a five-fold enhancement in oral bioavailability of insulin using SLN compared to orally administered insulin solution (8.26% vs 1.7%) (16). A high oral bioavailability (37.6%) of insulin was achieved by orally delivering 75 U/kg insulin in biodegradable polyisobutylcyanoacrylate nanospheres (17). Other strategies of improving oral delivery of proteins involve using proteolytic enzyme inhibitors such as sodium glycocholate, aprotinin, soybean trypsin inhibitor, bacitracin and camostat mesilitate that have shown promise in improving efficacy of orally delivered insulin (18). Chemical modifications in insulin such as attaching a targeting ligand like transferrin or cell penetrating peptides like TAT peptide have shown to assist in the transcytosis of insulin across the enterocytes (19, 20). IN-105, an insulin analog obtained through conjugation of short chain of polyethylene glycol (PEG) to insulin has demonstrated an oral dose dependent reduction in blood glucose post prandially in patients with T2DM, through improvement in solubility, stability against proteolytic degradation and intestinal absorption (21, 22). Absorption enhancers include bile salts, surfactants, fatty acids, calcium ion chelating agents, certain polymers such as chitosan/thiolated chitosan and zona occluden toxins that operate by either modulation of cell membrane structure of intestinal epithelium for transcellular uptake or tight junction permeability for paracellular transport (18).

ILs constitute a group of salts with organic cation and organic/inorganic anion that are typically liquid below 100° C. while some exist as liquid at room temperature (23). By pairing different ions, ILs can be tailored to have different physicochemical properties such as viscosity, hydrophobicity, solubility and biodegradability for a wide range of pharmaceutical applications in the fields of biocatalysis, enzymatic processes, protein stability, permeation enhancers and solubilizers amongst others (23-29). We have recently designed a choline-geranate (CAGE) based IL that greatly enhanced permeation of insulin across the skin (27).

The biocompatibility of orally-delivered CAGE was first tested in vitro using human intestinal Caco-2 cell line that has been extensively used as a model for intestinal absorption and barrier (30, 31). The $IC_{50}$ values for 12-48 h period of incubation was 10 mM suggesting that high concentrations of CAGE would not be cytotoxic to intestinal cells, thus demonstrating the utility potential of CAGE as a safe oral drug delivery agent.

To determine the efficacy of CAGE in the transport of insulin across intestinal cells, we dispersed insulin in 10 mM CAGE and incubated the formulation with Caco-2 cells for 5 h. CAGE significantly enhanced the transport of insulin by 3-4 fold throughout the period of study compared to insulin in saline. A temporary but significant drop in tight junction integrity in the cells was also noted and is postulated to have contributed toward enhanced transport of insulin across the cells. However, interplay of multiple other mechanisms may have also factored in toward augmenting transcytosis of insulin and remains to be investigated. It is important to note that CAGE caused only a transient decrease in tight junction integrity and the cells recovered their junction integrity to almost basal levels within 5 h, clearly suggesting that unlike many other permeation enhancers CAGE will not compromise the intestinal epithelial structure either permanently or for a prolonged period of time, thus mitigating any toxicity arising thereof.

Materials and Methods
Preparation of CAGE.

CAGE solvent was synthesized as per our previous study [Zakrewsky PNAS 2014]. Briefly, two equivalents of neat geranic acid (20 g, 0.119 mol, Sigma-Aldrich, St. Louis, Mo.) that had been recrystallized at least 5 times in acetone at <−70° C. to remove impurities, were added to one equivalent of choline bicarbonate (80 wt % solution, 12.275 g, 0.059 mol, Sigma-Aldrich, St. Louis, Mo.) in a 500-mL round-bottom flask. The mixture was stirred at 40° C. until $CO_2$ evolution ceased, and the water was removed by rotary evaporation at 60° C. for 2 h followed by drying in a vacuum oven for 48 h at 60° C. Physical characterization at 25° C. showed good agreement with previous values. The NMR spectra (collected using a 500-MHz Varian instrument, Palo Alto, Calif.) was also in good agreement with previous preparations: $^1$H NMR (DMSO-$d_6$), δ5.60 (s, 2H), 5.07 (t, J=6.1, 2H), 3.86 (t, J=6.6, 2H), 3.42 (t, J=6.6, 2H), 3.12 (s, 9H), 2.57 (m, 4H), 2.01 (m, 4H), 1.97 (s, 6H), 1.73 (s, 2H), 1.64 (s, 6H), and 1.57 (s, 6H); $^{13}$C NMR (DMSO-$d_6$), δ170.1, 150-1, 131.5, 124.1, 122, 67.6, 55.5, 53.6, 53.5, 32.8, 25.9, and 17.9.

Caco-2 Monolayer Culture in 96-Well Plate and Transwells.

Human epithelial colorectal adenocarcinoma cells (Caco-2, ATCC, Manassas, Va.) were seeded in 96-well plates at density of 1,000 cells/well and grown for 21 days to allow full differentiation and formation of a confluent monolayer in Dulbecco's Modified Eagle Medium (DMEM) supplemented with 10% Fetal Bovine Serum (FBS) and 1% penicillin-streptomycin (P/S) (ThermoFisher Scientific, Waltham, Mass.) at 37° C., 5% $CO_2$. During this period, cell media was changed every 2 days in the first week and every alternate day in the second and third weeks.

For transport experiments in transwells, a 3-day rapid Caco-2 growth system was used. Cells were placed in Corning® basal seeding media (BSM) supplemented with MITO serum+ extender and seeded at density of 400,000 cells/ml on Millicell® PCF inserts placed inside 24-well plates. 500 μl of cells containing medium was placed in apical side while 1000 μl of cell free BSM was put in the basolateral side as per manufacturer recommendation. After 24 h of incubation at 37° C., 5% $CO_2$, the medium was replaced with same volume of enterocyte differentiation medium supplemented with MITO serum+ extender for another 2-4 days. TEER was measured on a regular basis and when it reached above 200 ohms·$cm^2$, indicating sufficient tight junction integrity between cells, transport study was performed.

In Vitro Oral Biocompatibility Assessment of CAGE.

For this study Caco-2 cells grown in 96-well plates were utilized. CAGE was diluted with DMEM to concentrations ranging from 25 to 3.125 mM. Three different sets of CAGE dilutions were made (3 dilution replicates). The media was aspirated from each well and each dilution was dispensed (100 uL per well) into 6 wells (6 cell replicates). Control wells were filled with media only. The cells were incubated at 37° C., 5% $CO_2$ for 12, 24 or 48 h. At each time point, the CAGE-media mixture was aspirated from the wells, and cell viability was assessed using an MTT (3-(4,5-dimethylthiazol-2-yl)-1,5-diphenyltetrazolium bromide) assay. MTT powder (ThermoFisher Scientific, Waltham, Mass.) was mixed with media to a concentration of 0.5 mg/mL, added to each well (100 uL), and incubated at 37° C., 5% $CO_2$ for 4 h. The MTT solution was removed and 100 uL of dimethyl sulfoxide (DMSO, Sigma-Aldrich, St. Louis, Mo.) was added to each well. The plates were wrapped in foil and shaken for 20 min, then absorbance was read at 570 nm using a microplate reader (M220 Infinite Pro, Tecan Group Ltd, Morrisville, N.Y.). Absorbance readings were normalized using the non-treated cell viability values.

FITC-Insulin Transport Assay.

Before the start of the experiment, the existing medium in the transwell was replaced with DMEM devoid of phenol red, FBS and P/S in both the apical (200 μl) and basolateral side (600 μl) and the cells were incubated for 30 minutes. Thereafter, the medium in the apical side was replaced with 200 µl of 500 µg/ml FITC-insulin prepared with or without 10 mM CAGE and solubilized in phenol red, FBS and P/S free DMEM. Immediately after addition of FITC-insulin at the apical side, a 100 µl aliquot was withdrawn from the basolateral side and replaced with equal volume fresh DMEM. This was repeated at 1, 2, 3, 4 and 5 h. During the study, the transwell plates were placed inside an incubator at 37° C., 5% $CO_2$ on a shaker rotating at 100 rpm and only taken out to remove aliquots at the aforementioned time periods. After the end of study at 5 h, the FITC-insulin concentration in the aliquots were measured using a plate reader (Tecan, Infinite M1000, Mannedorf, Switzerland) at 495/520 nm excitation/emission wavelengths and plotted as % FITC-insulin transport vs time. Furthermore, TEER was measured at every time point when aliquots were withdrawn from the transwells and plotted as % change from initial value vs time.

For qualitative analysis of FITC-insulin uptake by Caco-2 cells, the transwells from FITC-insulin transport study were washed two times with PBS at the end of study, followed by addition of 100 µl of 4% paraformaldehyde and kept at 4° C. overnight. On the next day, paraformaldehyde was aspirated from the wells, membranes washed with PBS two times and the transwell membrane were cut out. These membranes were then gently placed on glass slides and mounting media (Vectashield™ Hardset, Vector Laboratories, Burlingame, Calif.) containing 4',6-Diamidino-2-Phenylindole, Dihydrochloride (DAPI) was added to it and the membranes were then covered with glass slides. Confocal imaging of the membranes was taken using Olympus Fluoview 1000™ Spectral Confocal instrument at 60× magnification.

Efficacy of Insulin-CAGE Upon Intrajejunal Administration and Evaluation of Pharmacokinetic Parameters.

The efficacy of intrajejunal administration of insulin-CAGE was determined in adult non-diabetic male Wistar rats fasted overnight but given free access to water. Before the start of the study, the rats were anesthetized, abdominal hair clipped and the area prepped for surgery using 70% ethanol and betadine. An incision was made in the abdomen to expose the intestine. The jejunum was located and injected with 100 µl of either 3 or 5 U/kg insulin dispersed in CAGE or 100 µl of controls (3 U/kg insulin in saline, neat CAGE and saline). Each formulation was tested in 6 rats with the exception of saline which was tested in only 3 rats. Thereafter, intestinal section was placed back into the abdomen and the muscle and skin sutured. Blood glucose was determined using a commercial glucose meter in the beginning and at every 0.5 h till the end of study at 5 h. The animals remained anesthetized throughout the study, at the end of which they were euthanized and the intestinal section around the injection site was removed for further histological examination to determine toxicity, if any. A separate group of 3 rats were subcutaneously injected with 2 U/kg insulin in saline for comparison of efficacy. The results were plotted as % change in blood glucose levels with respect to initial reading at t=0 vs time.

Pharmacokinetics of insulin delivered through CAGE was evaluated by collecting around 250 µL blood in BD Vacutainer® red top tubes at 0, 1, 2, 3 and 5 h from rats injected with 5 U/kg insulin-CAGE intrajejunally, 3 U/kg insulin-saline intrajejunally and 2 U/kg insulin-saline subcutaneously. Standard protocol was followed for separation of serum from whole blood. Briefly, the blood samples were left undisturbed at RT for 15-30 minutes to allow clot formation, followed by centrifugation at 2,000 g for 10 minutes. The clear supernatant (serum) was then collected into clean tubes, stored in ice during the procedure and subsequently at −20° C. till further analysis of insulin content. For evaluation of insulin concentration in the serum samples, human insulin ELISA kit (Thermo Fisher Scientific, Waltham, Mass.) was used and manufacturer protocol followed to determine insulin concentration at each time point. Pharmacokinetic parameters such as elimination rate constant ($K_{el}$), elimination half life ($t^{1/2}$), area under the curve (AUC) and % oral bioavailability (F) was calculated from serum insulin concentrations vs time plot.

In Vivo Oral Efficacy.

To determine the efficacy of insulin-CAGE administered through the oral route, elongated size 9 capsules (Torpac, Fairfield, N.J.) that were capable of housing 80 µl of CAGE was used. These capsules were filled with 80 µl of either 10 U/kg insulin-CAGE, neat CAGE or left empty. Following this, the capsules were enterically coated three times with 12.5% w/v Eudragit® L-100 dissolved in isopropanol to prevent capsule degradation in the stomach's acidic environment and provide intestinal site specific delivery of encapsulated CAGE. For the oral efficacy study, adult non-diabetic male Wistar rats were fasted overnight but given free access to water. On the next day, the capsules were administered to the rats using an oral gavage followed by subcutaneous administration of 5 mg/kg metoclopramide HCl to promote gastric emptying. Blood glucose was thereafter measured using a commercial glucose meter and subsequently every hour till 12 h. Rats were fasted throughout the period of study. A control of 10 U/kg insulin in saline was also tested by orally administrating the formulation as a solution (not in a capsule). In addition, the efficacy of subcutaneously injected 2 U/kg insulin-saline was also evaluated. For 10 U/kg insulin-CAGE and neat CAGE, a group of 6 rats per formulation was used while 3 rats per group was utilized for studying the efficacy of empty capsules, 10 U/kg insulin solution and 2 U/kg insulin-saline administered subcutaneously. The results were plotted as percent change in blood glucose level vs time.

Tissue Histology,

Tissue was fixed in 10% buffered formalin, dehydrated in ethanol, and embedded in paraffin. Five-micron cross-sections of intestine tissue was deparaffinized, rehydrated, and stained with Hematoxylin and Eosin. Histological morphology was examined using a light microscope at 10× and 40× magnification (Olympus BX60™ Upright Compound Microscope).

Assessment of Insulin Stability in CAGE.

Samples containing human insulin (100 U, 3.5 mg, Sigma-Aldrich, St. Louis, Mo.) were suspended in either 1 mL CAGE or PBS in 2 mL micro centrifuge tubes and incubated at room temperature (25° C.) or under refrigeration (4° C.). After 1 month, and approximately each month thereafter for 4 months total, samples were centrifuged for 10 min at 10 000×g, the CAGE was removed via pipette, and the soft insulin pellet was washed with 1 mL phosphate buffered saline (PBS) and centrifuged again. PBS-CAGE was removed, and the washing/centrifugation steps repeated until the insulin did not form a pellet during centrifugation.

Circular Dichroism (CD) Study:

To collect spectra in the far-UV region (190-250 nm) indicting protein secondary structures, circular dichroism spectrophotometry (Jasco J-1500, Easton, Md.) was performed with rectangular quartz cells (1 mm path length, Starna Cells, 1-Q-q, Atascadero, Calif.) loaded with 400 uL of sample.

Biological Efficacy Assessment In Vivo:

The biological activity of insulin isolated from CAGE was evaluated by subcutaneously injecting the insulin thus obtained at a dose of 1 U/kg into adult non-diabetic male Wistar rats. Blood glucose levels were monitored using a commercial glucose meter for 8 h and compared to freshly prepared insulin solution. All animal experiments were performed in accordance with the University of California Santa Barbara animal care committee guidelines and to the Guide for the Care and Use of Animals of the Institute of Laboratory Animal Resources, National Research Council. Prior to insulin injections, rats were fasted overnight but given free access to water and fasting continued throughout the study to eliminate variability in blood glucose due to food consumption. The results were plotted as % change in blood glucose compared to initial level vs time.

Data Analysis.

All data are presented as mean±standard error (S.E.). For statistical analysis, student's T-test was utilized. Significant difference was considered at $p<0.05$. All experiments were conducted in at least triplicates.

REFERENCES

1. Kharroubi A T & Darwish H M (2015) Diabetes mellitus: The epidemic of the century. *World J Diabetes* 6(6): 850-867.
2. Olokoba A B, Obateru O A & Olokoba L B (2012) Type 2 diabetes mellitus: A review of current trends. *Oman Med J* 27(4): 269-273.
3. World Health Organization (2016) Global report on diabetes
4. Centers for Disease Control (2017) National diabetes statistics report, 2017. estimates of diabetes and its burden in the united states. *National Center for Chronic Disease Prevention and Health Promotion:* 1-20.
5. McCulloch D K (2017) Patient education: Diabetes mellitus type 2: Insulin treatment (beyond the basics) 2017 (Nov. 8)
6. Peyrot M, Rubin R R, Kruger D F & Travis L B (2010) Correlates of insulin injection omission. *Diabetes Care* 33(2): 240-245.
7. Fonte P, Araujo F, Reis S & Sarmento B (2013) Oral insulin delivery: How far are we?. *J Diabetes Sci Technol* 7(2): 520-531.
8. Oleck J, Kassam S & Goldman J D (2016) Commentary: Why was inhaled insulin a failure in the market?. *Diabetes Spectr* 29(3): 180-184.
9. Soares S, Costa A, Fonte P & Sarmento B (2017) in *Drug Delivery: An Integrated Clinical and Engineering Approach*, eds Rosen Y, Gurman P & Elman N (Taylor and Francis,
10. Shaji J & Patole V (2008) Protein and peptide drug delivery: Oral approaches. *Indian J Pharm Sci* 70(3): 269-277.
11. Cui F D, Tao A J, Cun D M, Zhang L Q & Shi K (2007) Preparation of insulin loaded PLGA-Hp55 nanoparticles for oral delivery. *J Pharm Sci* 96(2): 421-427.
12. Pan Y, Xu H, Zhao H Y, Wei G & Zheng J M (2002) Study on preparation and oral efficacy of insulin-loaded poly(lactic-co-glycolic acid) nanoparticles. *Yao Xue Xue Bao* 37(5): 374-377.
13. Sarmento B, Ribeiro A, Veiga F, Ferreira D & Neufeld R (2007) Oral bioavailability of insulin contained in polysaccharide nanoparticles. *Biomacromolecules* 8(10): 3054-3060.
14. Sarmento B, et al (2007) Alginate/chitosan nanoparticles are effective for oral insulin delivery. *Pharm Res* 24(12): 2198-2206.
15. Zhang N, et al (2006) Lectin-modified solid lipid nanoparticles as carriers for oral administration of insulin. *Int J Pharm* 327(1-2): 153-159.
16. Ansari M J, et al (2016) Enhanced oral bioavailability of insulin-loaded solid lipid nanoparticles: Pharmacokinetic bioavailability of insulin-loaded solid lipid nanoparticles in diabetic rats. *Drug Deliv* 23(6): 1972-1979.
17. Radwan M A (2001) Enhancement of absorption of insulin-loaded polyisobutylcyanoacrylate nanospheres by sodium cholate after oral and subcutaneous administration in diabetic rats. *Drug Dev Ind Pharm* 27(9): 981-989.
18. Wong C Y, Martinez J & Dass C R (2016) Oral delivery of insulin for treatment of diabetes: Status quo, challenges and opportunities. *J Pharm Pharmacol* 68(9): 1093-1108.
19. Shah D & Shen W C (1996) Transcellular delivery of an insulin-transferrin conjugate in enterocyte-like caco-2 cells. *J Pharm Sci* 85(12): 1306-1311.
20. Liang J F & Yang V C (2005) Insulin-cell penetrating peptide hybrids with improved intestinal absorption efficiency. *Biochem Biophys Res Commun* 335(3): 734-738.
21. Khedkar A, et al (2010) A dose range finding study of novel oral insulin (IN-105) under fed conditions in type 2 diabetes mellitus subjects. *Diabetes Obes Metab* 12(8): 659-664.
22. Buckley S T, Hubalek F & Rahbek U L (2016) Chemically modified peptides and proteins—critical considerations for oral delivery. *Tissue Barriers* 4(2): e1156805.
23. Adawiyah N, Moniruzzaman M, Hawatulaila S & Goto M (2016) Ionic liquids as a potential tool for drug delivery systems. *Medicinal Chemistry Communications* 7: 1881-1897.
24. Yang M, et al (2014) Using ionic liquids in whole-cell biocatalysis for the nucleoside acylation. *Microb Cell Fact* 13: 143-014-0143-y.
25. Zakrewsky M, et al (2016) Choline and geranate deep eutectic solvent as a broad-spectrum antiseptic agent for preventive and therapeutic applications. *Adv Healthc Mater* 5(11): 1282-1289.
26. Zakrewsky M, et al (2014) Ionic liquids as a class of materials for transdermal delivery and pathogen neutralization. *Proc Natl Acad Sci USA* 111(37): 13313-13318.
27. Banerjee A, Ibsen K, Iwao Y, Zakrewsky M & Mitragotri S (2017) Transdermal protein delivery using choline and geranate (CAGE) deep eutectic solvent *Adv Healthc Mater* 6(15): 10.1002/adhm.201601411. Epub 2017 Mar. 24.
28. Sivapragasam M, Moniruzzaman M & Goto M (2016) Recent advances in exploiting ionic liquids for biomolecules: Solubility, stability and applications. *Biotechnol J* 11(8): 1000-1013.
29. Patel R, Kumari M & Khan A B (2014) Recent advances in the applications of ionic liquids in protein stability and activity: A review. *Appl Biochem Biotechnol* 172(8): 3701-3720.
30. Angelis I D & Turco L (2011) Caco-2 cells as a model for intestinal absorption. *Curr Protoc Toxicol* Chapter 20: Unit20.6.
31. Sambuy Y, et al (2005) The caco-2 cell line as a model of the intestinal barrier: Influence of cell and culture-related factors on caco-2 cell functional characteristics. *Cell Biol Toxicol* 21(1): 1-26.

Example 2: Ionic Liquids for Delivery into Tissues

Solubilization of hydrophobic drugs has long been a major hurdle in drug delivery. Many small molecules, chemotherapy drugs included, are highly hydrophobic in nature and require complex strategies for solubilization. The present invention describes the use of ionic liquids for this purpose. Another purpose of this disclosure is to demonstrate the use of ionic liquids for enhanced dispersion of drugs into tissues from the site of injections. Another purpose of this disclosure is to demonstrate the use of ionic liquids to enhance bioavailability of drugs after delivery into the subcutaneous or intradermal space.

Deep eutectic solvents (DESs) and ionic liquids (ILs) can enhance delivery of drugs as well as serve to disrupt/neutralize biofilm-forming bacteria. Furthermore, compared to conventional chemical penetration enhancers such as ethanol, the compositions described herein demonstrated lesser toxicity to cells thereby mitigating the issue of tissue irritation that is characteristic of many chemical enhancers. DES's are a mixture of compounds that collectively have a lower freezing temperature than individual components while IL's are salts consisting of an organic cation and organic/inorganic anion that are stable and in a liquid form at room temperature. Prior to the demonstration provided herein, the ability of ionic liquids, including CAGE, to solubilize hydrophobic drugs as well as biologics for parenteral administration, and its use to enhance drug dispersion and absorption has not been determined.

Methods

Preparation of CAGE.

Choline geranate deep eutectic was synthesized. Briefly, two equivalents of neat geranic acid (50.0 g, 0.297 moles, Sigma Aldrich, St. Louis, Mo.), were recrystallized 5× at −70° C. in acetone, in a 500-mL round bottom flask and added to one equivalent of choline bicarbonate (80% wt solution, 30.7 g, 0.297 moles, Sigma Aldrich, St. Louis, Mo.). The mixture was stirred at room temperature until $CO_2$ evolution ceased. Residual $H_2O$ was removed by rotary evaporation at 60° C. for 2 hr and drying in a vacuum oven for 96 hr at 60° C. Physical characterization at 25° C. is in good agreement with published values and is as follows: density, 0.989±0.001 g/mL; and conductivity, 0.0427±0.0005 mS/cm. NMR spectra are provided. NMR assignments are also in good agreement with published assignments and are included as follows: 1H NMR (DMSO-d6), δ 5.57 (s, 2H), 5.07 (t, J=6.1, 2H), 3.85 (t, J=6.6, 2H), 3.42 (t, J=6.6, 2H), 3.17 (s, 9H), 2.60 (m, 4H), 2.00 (m, 4H), 1.93 (s, 6H), 1.70 (s, 2H), 1.64 (s, 6H), and 1.57 (s, 6H); 13C NMR (DMSO-d6), δ 170.3, 150.4, 131.5, 124.0, 121.7, 67.6, 55.6, 53.5, 40.4, 32.8, 25.8, and 17.8.

Physical Characterization.

NMR spectroscopy was performed to verify the identity of the final product. 1H and 13C NMR spectra were collected on a 600-MHz Varian instrument using sample concentrations of ~50 mM in DMSO-d6. 1H spectra were averaged over 128 scans with a 2 sec relaxation delay between pulses. 13C spectra were averaged over 512 scans with a 2 sec relaxation delay between pulses. Density was measured three times using a 1 mL volumetric flask and an analytical balance. Conductivity was measured with a DS-71 conductivity meter (Horiba, Kyoto, Japan) with a flow type conductivity electrode (Horiba, Kyoto, Japan) calibrated with KCl standard solutions. Conductivity was measured three times per sample using 0.25 mL samples at 25° C.

In Vivo Experiments.

Efficacy of insulin delivery from CAGE was assessed in normal rats. Prior to the day of experiment, the animals were fasted overnight and but given free access to water. Insulin was suspended in CAGE prior to administration. Animals were anesthetized and insulin-CAGE was subcutaneously injected. For control experiments, CAGE alone or insulin-saline was injected. Blood glucose levels from the tail vein were measured at different time intervals using a commercial blood glucose meter.

In Vitro Cell Culture Experiments.

In vitro anticancer efficacy of drug-loaded liposomes was determined using calcein-AM cell viability assay (Life Technologies). 4T1 cells were seeded in a 96-well cell culture plate at a density of 11,000 cells per well or 1,000 cells per well in a total volume of 100 µL media and allowed to adhere overnight. Media was then replaced with fresh media containing liposomes and incubated for 48 hours with 4T1 cells, respectively. After incubation with drug, media was aspirated and replaced with 1 µM calcein-AM in PBS for 30 minutes at room temperature. Fluorescence intensity of intracellularly hydrolyzed calcein-AM was measured using excitation and emission wavelengths of 490 nm and 520 nm. Fractional cell inhibition was calculated by subtracting fluorescence of live cells in experimental wells from those of untreated cells and normalizing against untreated cells.

Effect of CAGE on Spreading of Molecules in the Tissue.

Experiments were performed to determine if CAGE can be used to enhance distribution of molecules within the tissue from the point of injection. These experiments were done using skin as a model tissue. For this purpose, 1 mg/ml labeled (FITC or AntoniaRed) 150 kDa dextran was suspended in either: Neat 1:1 CAGE, 50% CAGE (diluted with saline), 10% CAGE (diluted with saline) or Saline. 50 ul of each sample was injected intradermally into one side of a 5 cm×5 cm square of porcine skin. 2 differently labeled samples of the same CAGE concentration were injected into the same square. The samples were incubated at RT for 2 h (while we were getting trained) and then imaged. The samples were incubated for an additional 2 h at 37° C. and imaged again. 2 h samples had different exposures (we were still learning the system). The 4 h samples were all taken at the same exposure. The size of the fluorescing area for each sample and time point was estimated by drawing a shape around the area manually using ImageJ™

Results

Solubility: Solubility of two hydrophobic drugs in CAGE was determined, paclitaxel and camptothecin. Both drugs are practically insoluble in water and require solubilization strategies or alterations to drug chemistry. For example, lack of solubility of paclitaxel in water led to the use of a solvent, cremophor, which is now used in the clinic. Cremophor, however, suffers from toxicity issues. Camptothecin, on the other hand, is not clinically used due to lack of solvent and an alternate chemical form, irrinotecan, is clinically used. The ability of CAGE to solubilize both drugs provides a clear advantage over the alternatives.

Paclitaxel: 200+/−48 mg/ml

Camptothecin: 54 mg/ml

This ability of CAGE to solubilize hydrophobic drugs can be used for various drugs, for example, estradiol, testosterone, imiquimod, corticosterone, paclitaxel, doxorubicin, cisplatin, camptothecin. These hydrophobic drugs currently require complex strategies including solvents such as ethanol or DMSO, which cannot be used for many applications especially for injection-based delivery systems. Alternatively, strategies have been developed to solubilize drugs in micelles. Use of micelles, though useful for solubilization, substantially changes the drug properties form a 'small molecule' to a colloid. This transformation significantly changes the therapeutic outcome. Solubilization of drugs in CAGE can directly address this limitation. CAGE can be used in several possible ways. In one way, the solubilized drug can be formulated for topical applications such as an oral or a transdermal application. The primary contribution of CAGE in this application is to hold the solubilized drug within the formulation so as to provide a high concentration gradient for drug diffusion across the barrier. In another application, the drug solution in CAGE can be injected intradermally, subcutaneously or intravenously. In such formulation, CAGE serves to solubilize the drug, thus enabling injections of high concentrations. In one embodiment, upon injection, CAGE can diffuse into the tissue, thus allowing local precipitation of the drug. The precipitated drug can form a depot and exhibit sustained release. In another embodiment, the drug may continue to remain soluble in CAGE even after local diffusion of CAGE and lead to quick and enhanced delivery into circulation.

In vitro efficacy of chemotherapy drugs dissolved in CAGE: Effect of camptothecin and paclitaxel solubilized in CAGE on 4T1 cancer cells was tested. A positive control of the same drugs dissolved in DMSO was used. Note that while DMSO is a solvent used in the in vitro studies, it is not a clinically acceptable alternative.

The embodiments described here can be used in multiple ways. In one form, the chemotherapeutic drug is solubilized in CAGE and delivered directly into the tumor. Solubilized chemotherapeutic drug may diffuse into the tumor, thus enabling a therapeutic effect. Note that CAGE by itself also has cytotoxic effect at high concentration. In one embodiment, CAGE can be injected directly into the tumor to achieve local cytotoxic effect. Such treatment can be used for the treatment of solid tumors such as those in the liver, pancreas or breast. In one embodiment, CAGE can be injected directly into adipose tissue to promote lysis. CAGE can either directly lyse the adipose cells by dissolution or induce sufficient disruption to promote macrophage/immune cell-mediated clearance.

In vivo efficacy of insulin delivery from CAGE: Insulin delivered from CAGE was highly bioactive. A simple suspension of insulin in CAGE was subcutaneously injected. This formulation yielded substantial hypoglycemia (FIG. 12), which was superior to insulin solution in saline.

Figure 12:
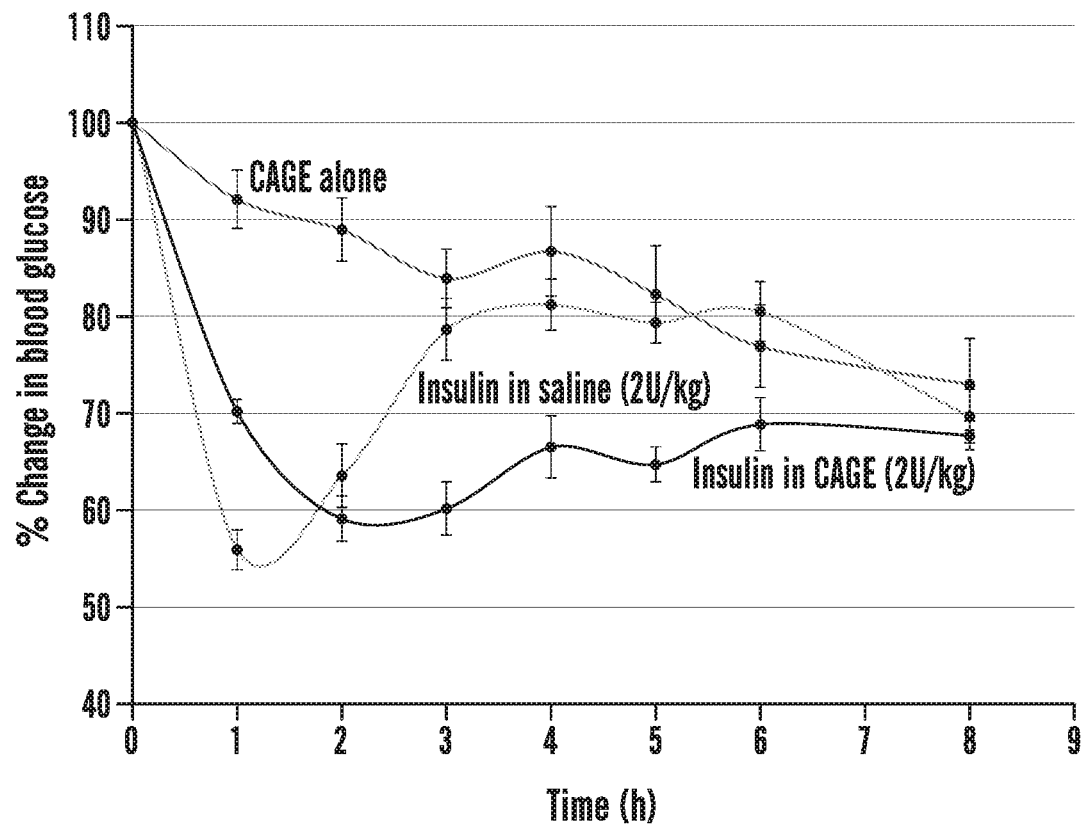
FIG. 12 depicts the biological activity of subcutaneously delivered insulin (2 U/kg) from CAGE (blue) and controls (2 U/kg in saline, orange) and CAGE alone (green). Compared to standard insulin-saline injections, insulin in CAGE yielded substantially longer duration of hypoglycemia.

The embodiment described in FIG. 12 can be used in multiple ways. In one form, CAGE can be used to enhance absorption of biologics into circulation. Large biologics such as antibodies have limited absorption into systemic circulation after injection into subcutaneous space. Addition of CAGE can enhance that bioavailability. In another embodiment, CAGE can be used to change pharmacokinetics of injected drug. For example, insulin, which is rapidly absorbed from the subcutaneous injection site, can be made to exhibit sustained absorption by addition of CAGE (FIG. 12).

Figure 13:
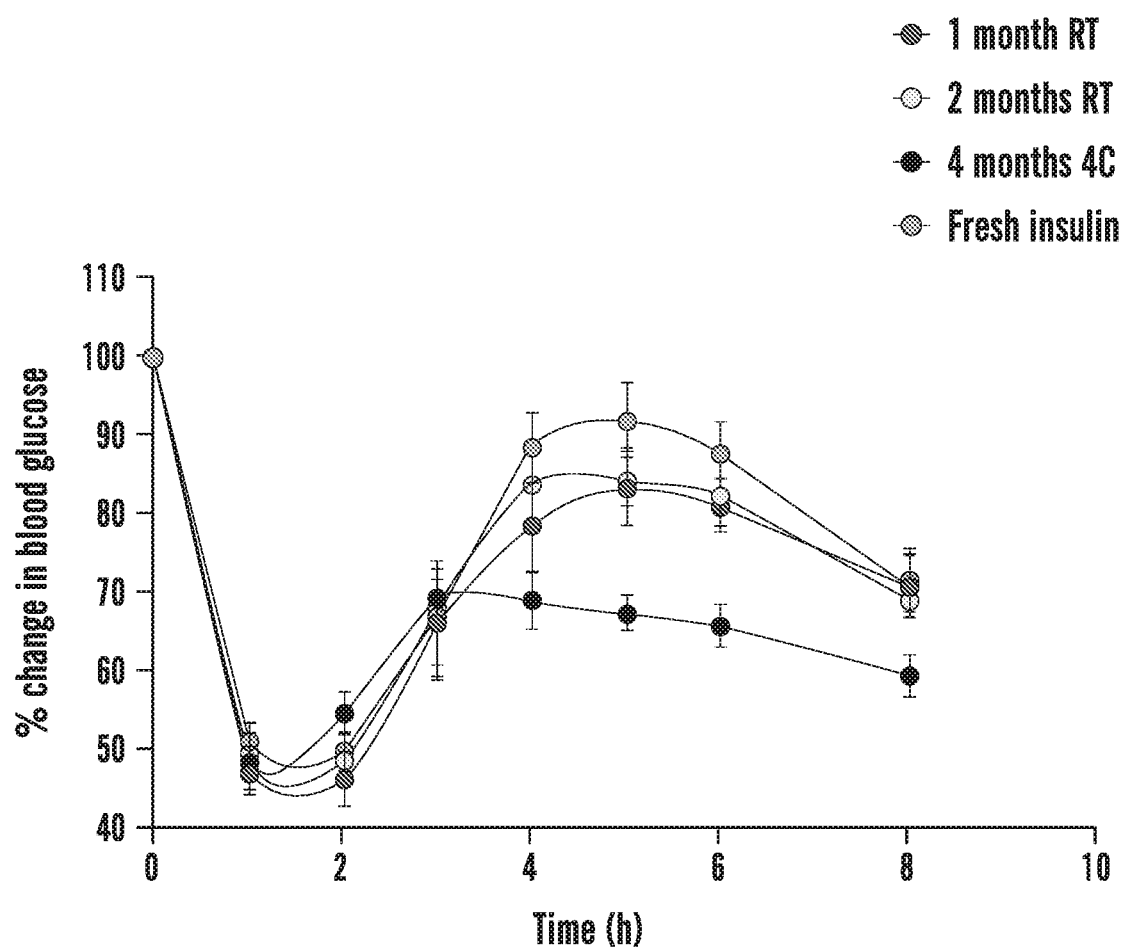
FIG. 13 depicts the biological activity of insulin stored in CAGE at room temperature (RT) and 4° C. Biological activity was maintained even after 2 months of storage at room temperature.

Stabilization of Biomolecules: Stability of insulin in CAGE was assessed. Insulin was suspended in CAGE and left at room temperature or 4° C. After one or two months, insulin was injected subcutaneously and its biological activity was assessed based on blood glucose response (FIG. 13). Biological activity of insulin-CAGE stored at room temperature was comparable to native insulin after 2 months, thus demonstrating the effect of CAGE on stabilization of biomolecules.

Stabilization of biomolecules by CAGE can be used for preservation of degradation of vaccines. Vaccines are typically formulated in an aqueous formulation and it needs refrigeration to maintain activity. This cold-chain requirement makes if difficult to deliver vaccines to the remote parts of the world. CAGE can be used to preserve the vaccine activity at room temperature.

Figure 14:
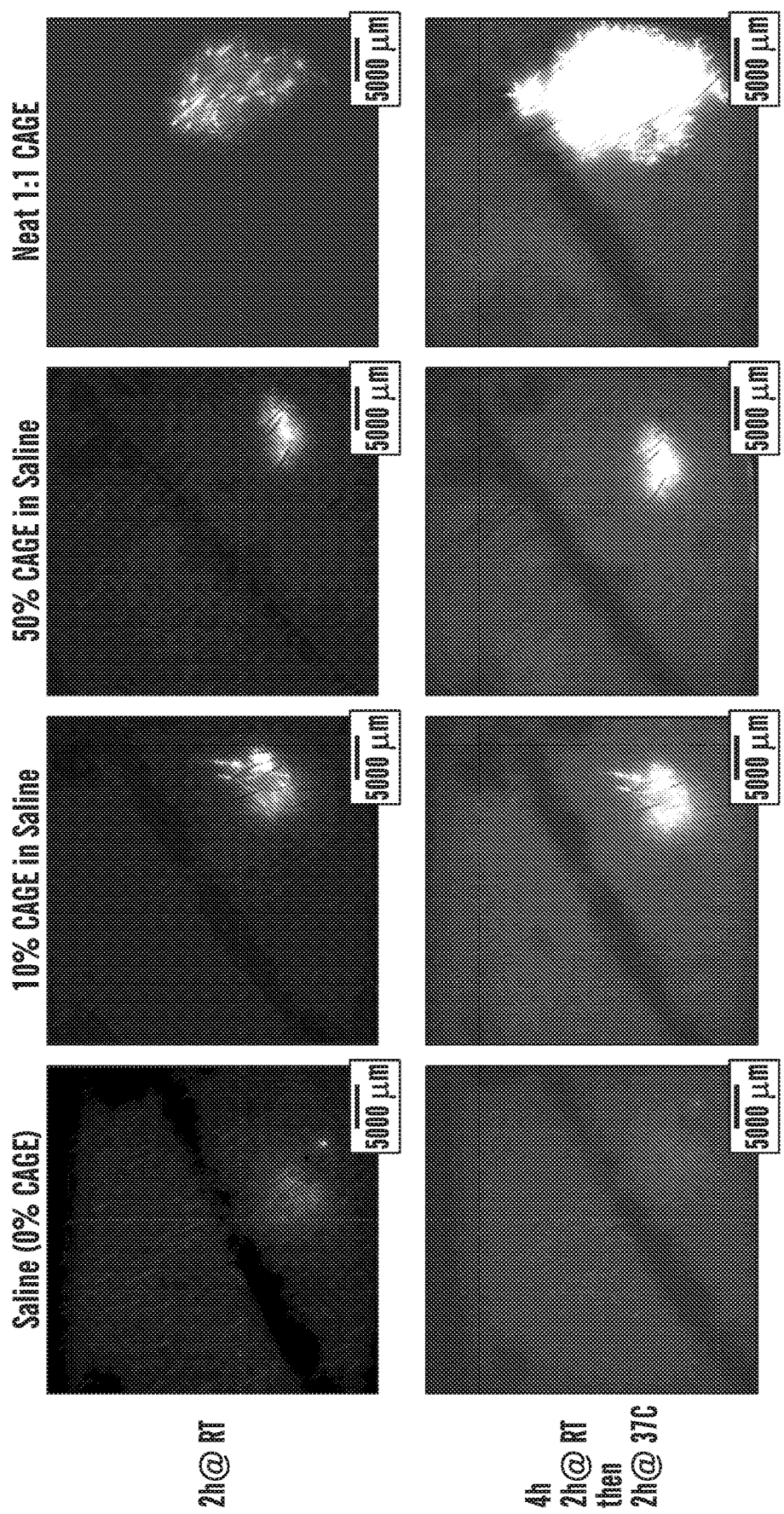
FIG. 14 depicts the effect of CAGE on dispersion of dextran in the tissue. Compared to saline (left-most panel), the addition of CAGE to the formulation enhances dispersion of dextran in the skin. The magnitude of enhancement is quantified in the table in Example 2. Neat CAGE enhanced the spread of dextran between 2.6 to 5.5-fold.

Enhanced dispersion within the tissue: All the AntoniaRed labeled dextran samples appeared to spread moderately between the 2 h and 4 h timepoints. The FTIC labeled dextran samples did not appear to spread between 2 and 4 h, with the exception of the neat CAGE sample, with an area increase of about 2×. (see, e.g., FIG. 14)

This embodiment can be used in multiple ways. In one form, CAGE can be used to enhance its own distribution into the tissue after injection for the treatment of a local condition such as tumor or wart. The effect of CAGE on local tissue can also be used to enhance the distribution of a solubilized drug such as a chemotherapeutic agent.

The term "ionic liquids" as used herein refers to organic salts or mixtures of organic salts which are in liquid state at room temperature. This class of solvents has been shown to be useful in a variety of fields, including in industrial processing, catalysis, pharmaceuticals, and electrochemistry. The ionic liquids contain at least one anionic and at least one cationic component. Optionally, the IL contains an additional hydrogen bond donor (i.e. any molecule that can provide an —OH or an —NH group), examples include but are not limited to alcohols, fatty acids, and amines. In some embodiments, the cationic or anionic component is also a drug.

The behavior of ILs is dominated by ionic interactions, whereas Deep Eutectic Solvents (DESs) exhibit a strong contribution from hydrogen bonding. Classification of systems involving ionic and neutral species is complex, due largely to the limitations of current definitions. In this respect, the definitions and descriptions provided herein for compositions, ionic liquids, and deep eutectic solvents are to be controlling over terminology as it may be applied by others in the field.

The at least one anionic and at least one cationic component may be present in any molar ratio. Exemplary molar ratios (cation:anion) include but are not limited to 1:1, 1:2, 2:1, 1:3, 3:1, 2:3, 3:2, and ranges between these ratios. In some embodiments, the IL is a deep eutectic solvent (DES). A DES is a type of ionic solvent with special properties composed of a mixture which forms a eutectic with a melting point much lower than either of the individual components. Exemplary DES include, but are not limited to, choline oleate, choline hexanoate, choline geranate, choline malonate (choline disodium malonate), and urea-choline. In these the formulation is a DES and not a true ionic liquid because excess carboxylate precludes 1:1 ion pairing. The ions used to prepare IL/DES can include molecules other than choline or generic acid. For example, derivatives or analogs of choline can be used as cations. At the same time, analogs or derivatives or geranic acid can also be used as anions.

The drug to be delivered may include a small molecule, peptide, protein, nucleic acid, antibody or any other therapeutically active molecule.

Example 3: Ionic Liquids for Oral Insulin Delivery

With the rise in diabetes mellitus cases worldwide and lack of patient adherence to glycemia management using injectable insulin, there is an urgent need for the development of efficient oral insulin formulations. However, the gastrointestinal tract presents a formidable barrier to oral delivery of biologics. Described herein is the development of a highly effective oral insulin formulation using Choline and Geranate (CAGE) ionic liquid. CAGE significantly enhanced paracellular transport of insulin, while protecting it from enzymatic degradation and by interacting with the mucus layer resulting in its thinning. In vivo, insulin-CAGE demonstrated exceptional pharmacokinetic and pharmacodynamic outcome after jejunal administration in rats. Low insulin doses (3-10 U/kg) brought about a significant decrease in blood glucose levels, which were sustained for longer periods (up to 12 h), unlike subcutaneously injected insulin. When 10 U/kg insulin-CAGE was orally delivered in enterically coated capsules using an oral gavage, a sustained decrease in blood glucose of up to 45% was observed. The formulation exhibited high biocompatibility and was stable for 2 months at room temperature and for at least 4 months under refrigeration. Taken together, the results indicate that CAGE is a promising oral delivery vehicle for oral delivery of insulin and other biologics that are currently marketed as injectables.

Insulin is currently available as an injectable formulation, but an oral product would enjoy higher patient compliance and would significantly improve the quality of life of diabetic patients worldwide. However, oral delivery of proteins such as insulin is challenging due to various gastrointestinal barriers to oral absorption of macromolecules. Described herein is the development of a safe and highly effective ionic liquid-based oral insulin formulation that significantly enhanced oral insulin absorption by efficiently circumventing the gastrointestinal barriers. Besides, the formulation demonstrated good stability at room temperature and under refrigeration.

The oral route of drug administration is preferred over injections due to its ease of administration, high patient compliance and low manufacturing costs. However, due to various gastrointestinal barriers to drug absorption, it is unsuitable for the delivery of biologics. For example, insulin is an indispensable medication for Type 1 diabetes management. It is currently administered as a subcutaneous injection but is associated with lack of patient adherence due to pain and needle-phobia associated with injections (1). Orally delivered insulin could significantly enhance patient compliance. In addition, it would closely mimic the physiological path of pancreatic insulin (2, 3). Oral/pancreatic insulin is transported to the liver via the portal vein where 80% is retained and the rest reaches systemic circulation, creating up to 3-fold higher insulin concentration in the portal vein compared to systemic circulation (3). This portal-peripheral insulin gradient is disrupted when insulin is injected subcutaneously due to a higher systemic insulin concentration compared to that in the portal vein (only ~20%) which disrupts the liver's fine balance between glycogen storage and glucose output. This often results in hyperglycemia, which when treated with higher insulin dose, can lead to hypoglycemia (3, 4).

The pursuit of an oral insulin product began many decades ago. Several strategies have been developed to overcome the gastrointestinal barriers to oral absorption of biologics. However, no formulation has successfully cleared all clinical hurdles and therefore no oral insulin products are commercially available. Products that have completed or are currently in phase II clinical trials include enterically coated capsules with additives to improve oral insulin uptake (Capsulin™ by Diabetology Ltd and ORMD-0801 by Oramed Ltd), hepatic directed liposomal insulin (HDV-Insulin by Diasome Pharmaceuticals Inc.), polyethylene glycol (PEG) conjugated insulin (IN-105 by Biocon Ltd.), insulin-proinsulin-c-peptide in Oshadi carrier (Oshadli Icp by Oshadi drug administration Ltd) and long-acting insulin analog tablets using gastrointestinal permeation enhancer technology (GIPET 1 by Novo Nordisk) (5-7). In addition, many products require multi-step formulation procedures, various additives or chemical modification of the protein, which have their own shortcomings. With the emerging global diabetes epidemic, there is a sense of urgency to develop safe, effective and easily scalable oral insulin products.

Described herein is an ionic liquid (IL)-based oral formulation of insulin and demonstrations of its safety, efficacy and long-term stability. Ionic liquids consist of organic/inorganic salts with melting points below 100° C. (8-10). Herein, a room temperature stable choline and geranate (CAGE) deep eutectic solvent was utilized (11, 12). Insulin was dispersed in CAGE in a single step process and its safety and efficacy was evaluated both in vitro and in vivo as well as its storage stability. The study demonstrates an unprecedented improvement in oral bioavailability of insulin with excellent oral efficacy, biocompatibility and long-term stability.

Results

Insulin was Stable in CAGE for Long Periods of Time.

Figure 15:
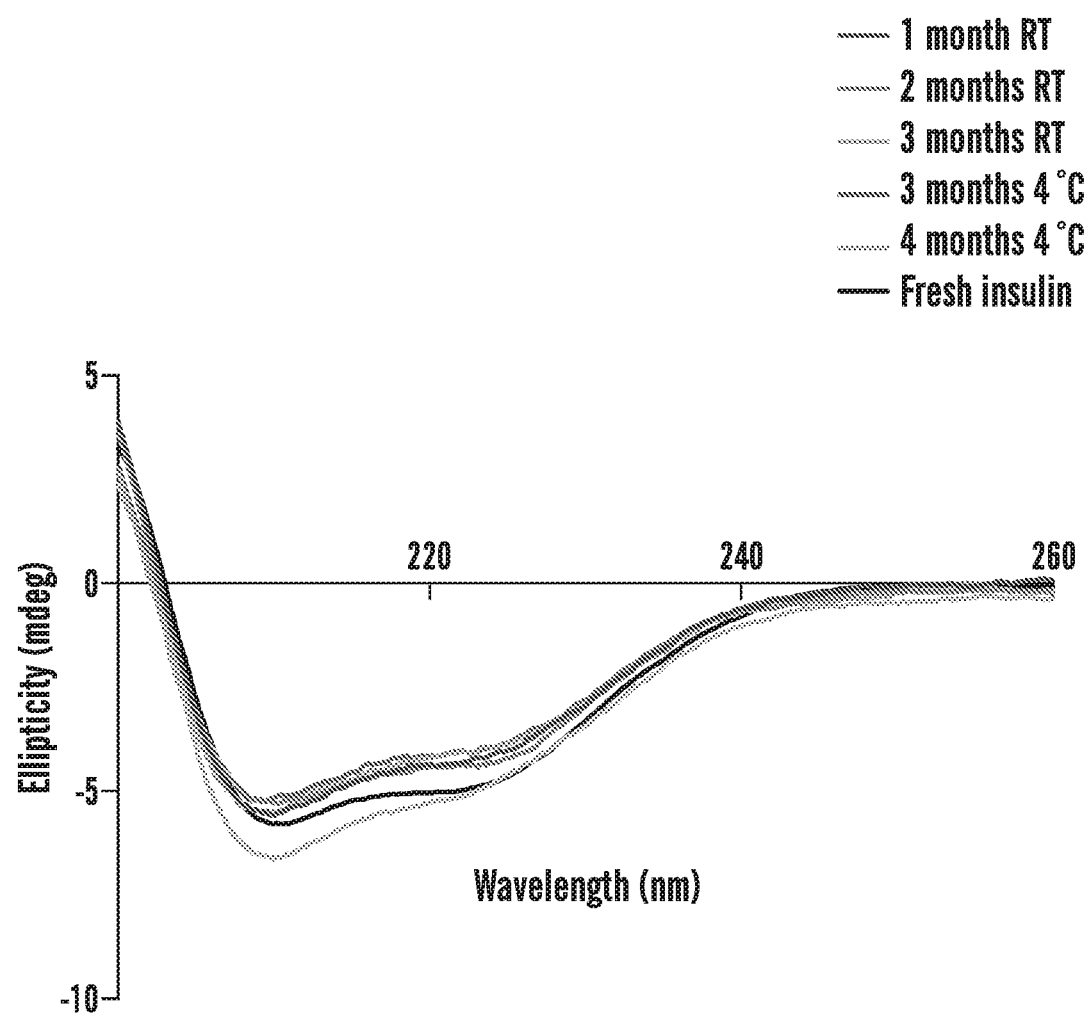
FIG. 15 depicts circular dichroism spectra of insulin isolated from CAGE at different months. Insulin was dispersed in CAGE and stored at room temperature (25° C.) or under refrigeration at 4° C. for up to 4 months. The alpha-helical secondary conformation of insulin was retained in CAGE for extended periods of time.

Insulin has an inherent alpha-helical conformation, which is essential for its receptor interaction, and hence its bioactivity (13). Prior to performing functional tests of oral delivery with CAGE, it was assessed whether insulin is stable in CAGE for extended periods of time. Insulin-CAGE was stored at room temperature (away from direct sunlight) or under refrigeration at 4° C. and the secondary structure of insulin isolated from CAGE every month for a period of 4 months were evaluated using circular dichroism (CD). Results showed the presence of double negative troughs at around 207 and 222 nm, which is a typical representation of an alpha-helix in a CD graph (FIG. 15). No difference in the shape or degree of ellipticity was noticed between freshly prepared insulin solution and insulin stored in CAGE at RT or 4° C. for up to 3 and 4 months respectively. The result indicates that CAGE preserves the secondary structure of insulin for long periods of time.

To validate the CD stability data, the biological activity of insulin isolated from CAGE at different times was evaluated in non-diabetic rats. For this purpose, rats that were fasted overnight were subcutaneously injected with insulin (isolated from CAGE and re-suspended in sterile saline) and blood glucose was monitored for a period of 8 h. No significant difference in biological activity was seen between fresh insulin and insulin-CAGE stored at RT for 1-2 months or at 4° C. for 1-4 months (FIG. 10). An attenuated efficacy was observed for insulin stored at RT for 3 months while insulin stored at 4° C. with CAGE, did not show any loss in bioactivity even after 4 months of storage. This clearly illustrates that CAGE is an excellent solvent for long-term storage of insulin.

Insulin-CAGE Caused Profound Hypoglycemia and Demonstrated Exemplary Pharmacokinetics Upon Intrajejunal Administration.

Figure 16A:
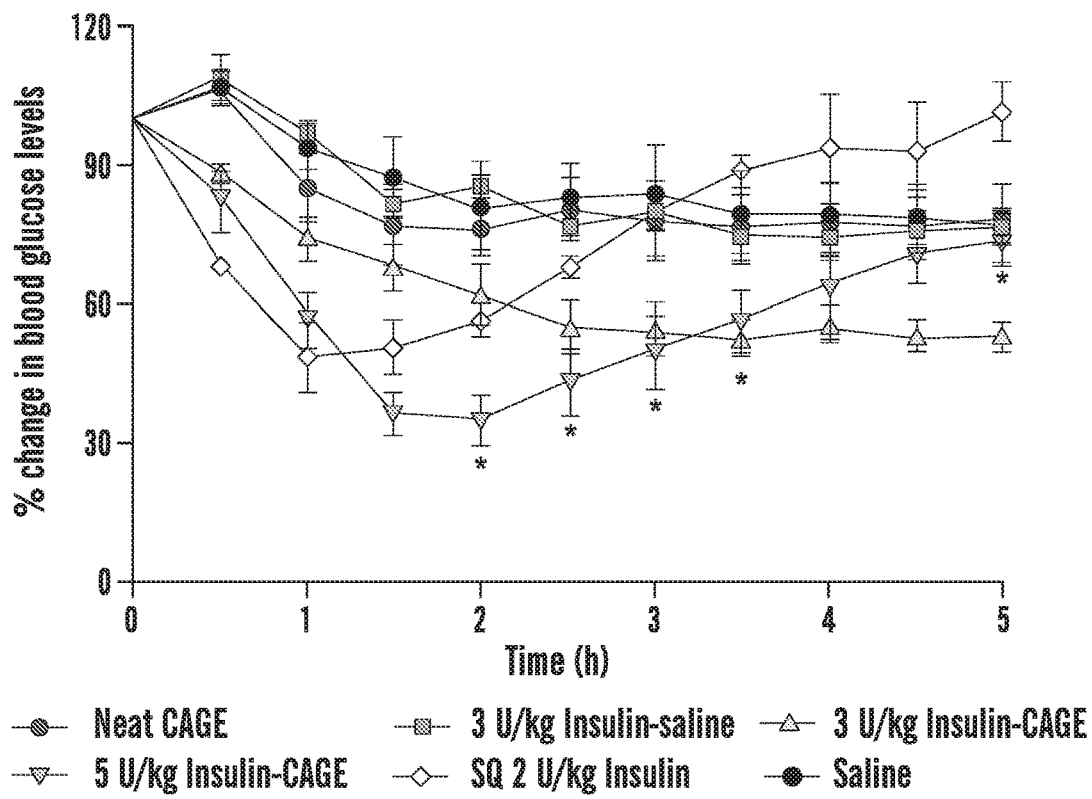
FIGS. 16A-16B demonstrate the efficacy of Insulin-CAGE in lowering blood glucose levels upon intrajejunal administration in non-diabetic rats.
Figure 16B:
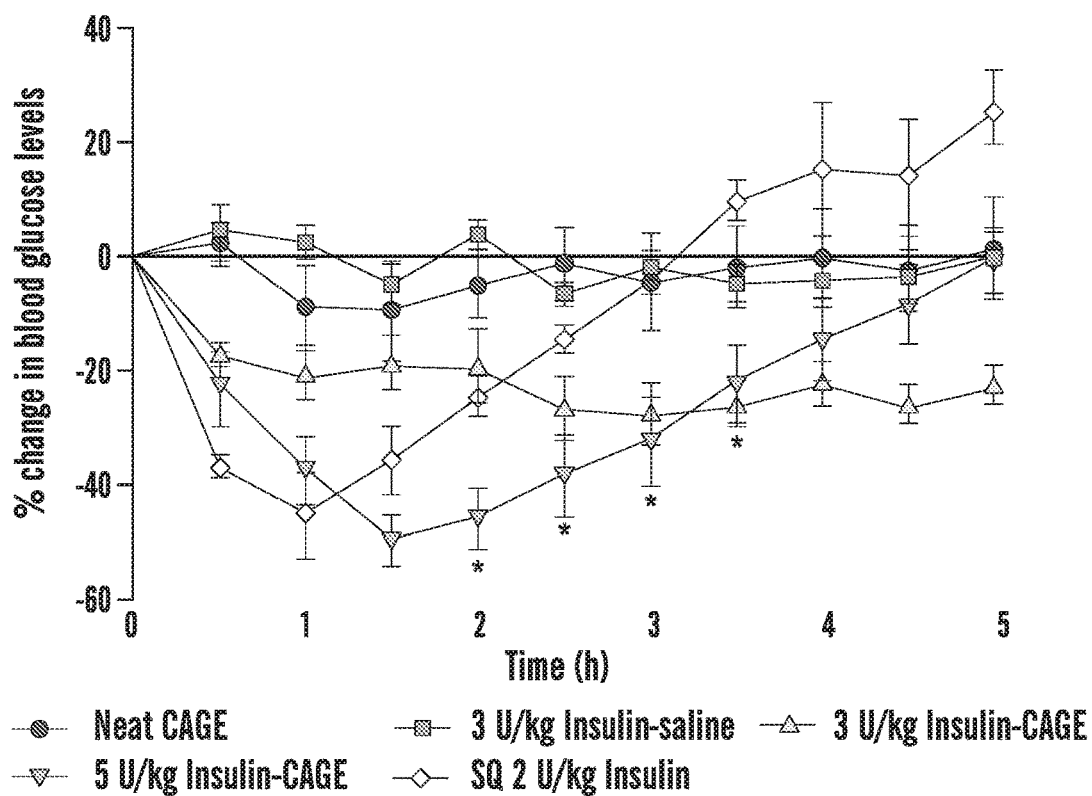
Figure 17:
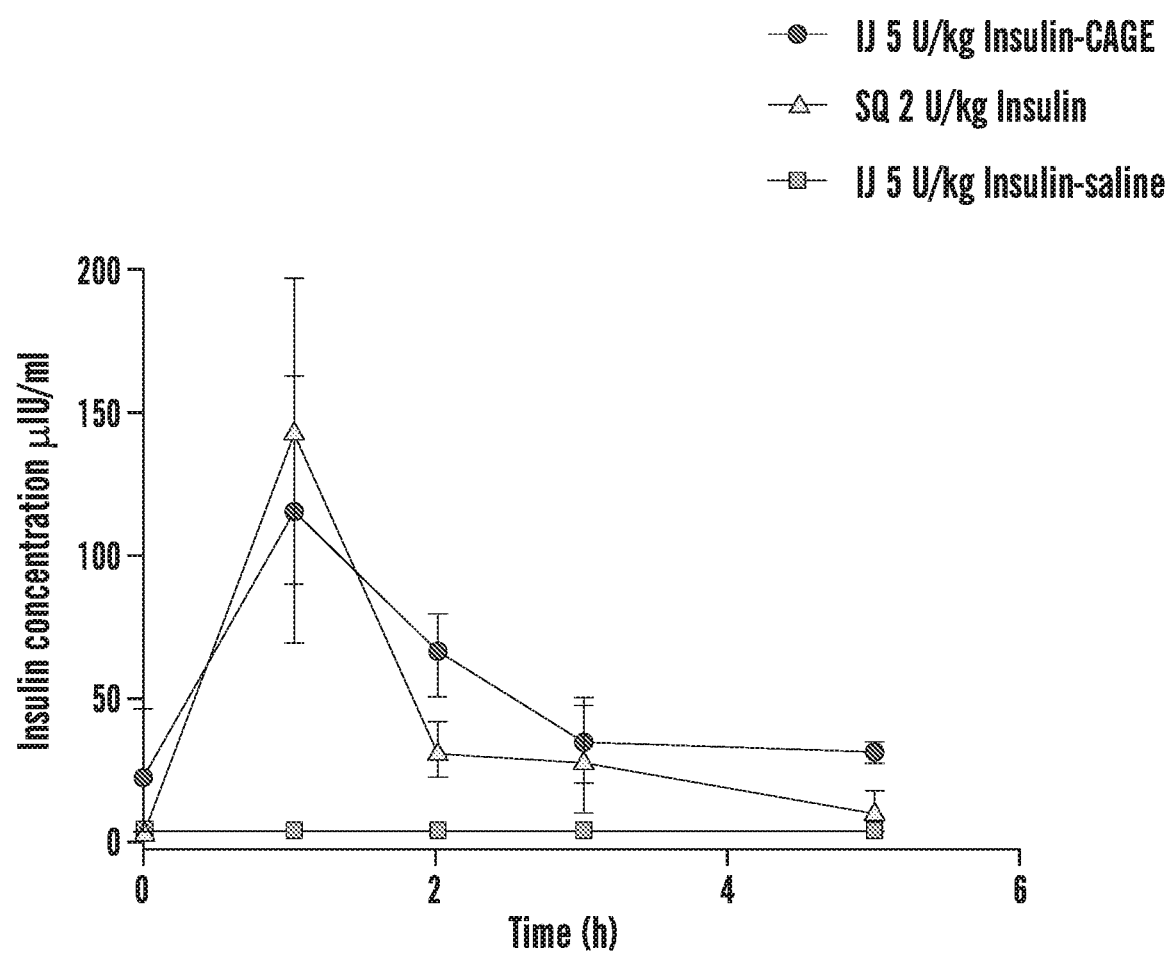
FIG. 17 depicts the efficacy of CAGE in enhancing the oral bioavailability of insulin. Data represented as mean±S.E. (n=4).

To gauge the efficacy of insulin-CAGE in lowering blood glucose levels, 3-5 U/kg insulin was dispersed in CAGE and administered to anesthetized non-diabetic rats intrajejunally, followed by blood glucose monitoring every 0.5 h for a total of 5 h (FIG. 16). Rats administered with 3 U/kg insulin-CAGE showed a steady drop in blood glucose levels from 0.5 h till it dropped by 45% of its initial value (55±6%) in 2.5 h. Beyond this point, the blood glucose levels plateaued, ending at 47% in 5 h. The group treated with 5 U/kg insulin-CAGE showed a sharp decrease in blood glucose levels that culminated in ~65% drop within 1.5 and 2 h (37±5 and 35±5% respectively). Blood glucose increased thereafter, which is a typical homeostatic response in non-diabetic rats that are subjected to a sudden and rapid decrease in blood glucose levels. At the end of 5 h, the blood glucose level was 74% of initial levels. The rats that were subcutaneously injected with 2 U/kg insulin also showed a similar pattern of blood glucose drop but to a lesser extent compared to 5 U/kg insulin-CAGE. A maximum drop of 51% was observed in 1 h (49±8% of initial level), which rapidly recovered to 100% at the end of the study at 5 h (101±7%). Controls such as neat CAGE, saline or 3 U/kg insulin-saline intrajejunal administration did not bring about a significant drop in blood glucose. In all these control groups, blood glucose decreased slowly (most likely due to continued fasting) to about 25% of initial levels in 5 h. The pharmacokinetics of insulin absorption and elimination was determined by measuring serum insulin levels at different time points (FIG. 17). Insulin concentration rapidly increased within an hour after SQ injection of 2 U/kg insulin and intrajejunal (IJ) administration of 5 U/kg insulin-CAGE and subsequently dropped to follow a similar pattern in elimination. The pharmacokinetic parameters calculated using serum insulin concentrations showed that the elimination half-life of intrajejunally administered insulin-CAGE was almost two-fold higher than SQ insulin (Table 2). The oral bioavailability of 5 U/kg IJ Insulin-CAGE thus calculated was found to be 51%. The pharmacodynamic bioavailability of the formulation as calculated from efficacy plots was 66%. On the contrary, 5 U/kg insulin-saline administered IJ, did not show any increase in insulin level with time.

TABLE 2

Pharmacokinetic parameters of insulin-CAGE given intrajejunally and insulin solution administered subcutaneously

| Formulation | $K_{el}$ (h$^{-1}$) | $t^{1/2}$ (h) | $AUC_{total}$ (µIU · h/mL) | % F |
|---|---|---|---|---|
| Insulin-CAGE IJ | 0.32 | 2.2 | 300.6 | 51 |
| Insulin SQ | 0.58 | 1.2 | 237.6 | |

*elimination rate constant ($K_{el}$); half-life ($t^{1/2}$); area under curve (AUC); bioavailability (F)

Insulin-CAGE Administered Orally in Capsules Demonstrated Notable Efficacy in Lowering Blood Glucose Levels.

The remarkable efficacy of CAGE in enhancing oral bioavailability of insulin upon intrajejunal administration prompted us to investigate its efficacy upon oral delivery using capsules. To this end, 10 U/kg insulin-CAGE or its controls was placed in enterically coated elongated size 9 capsules and administered to non-diabetic rats using an oral gavage.

Figure 18A:
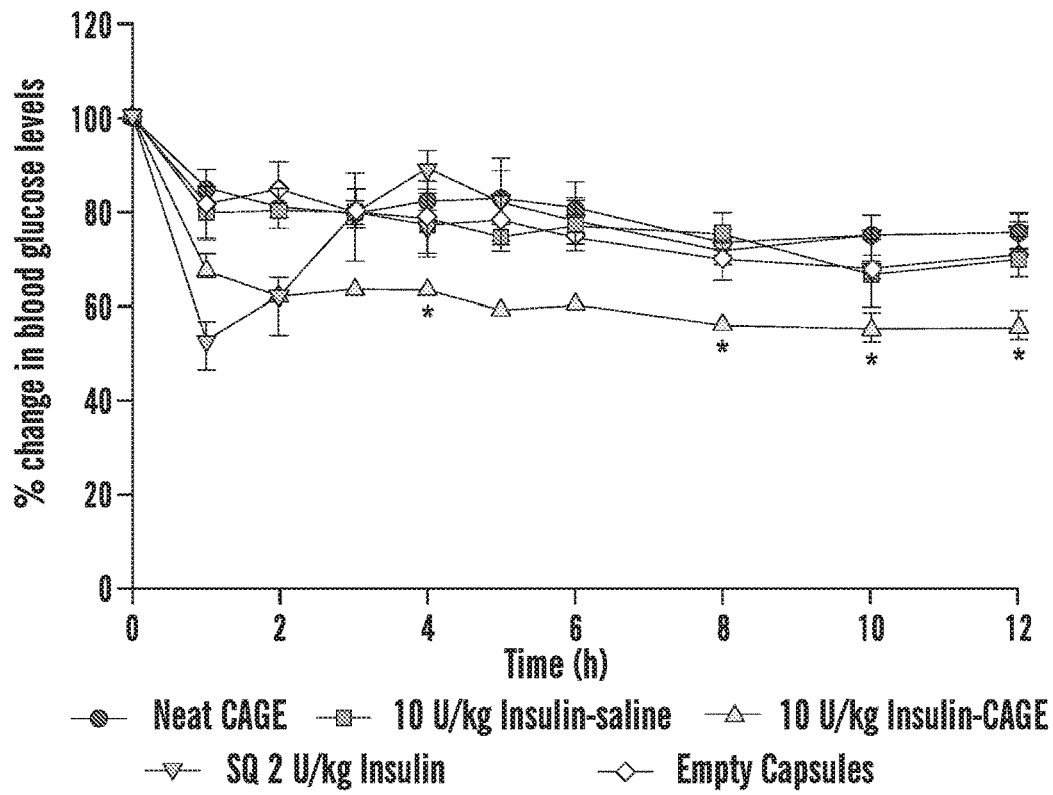
FIGS. 18A-18B demonstrate the In vivo efficacy of insulin-CAGE orally administered in capsules.
Figure 18B:
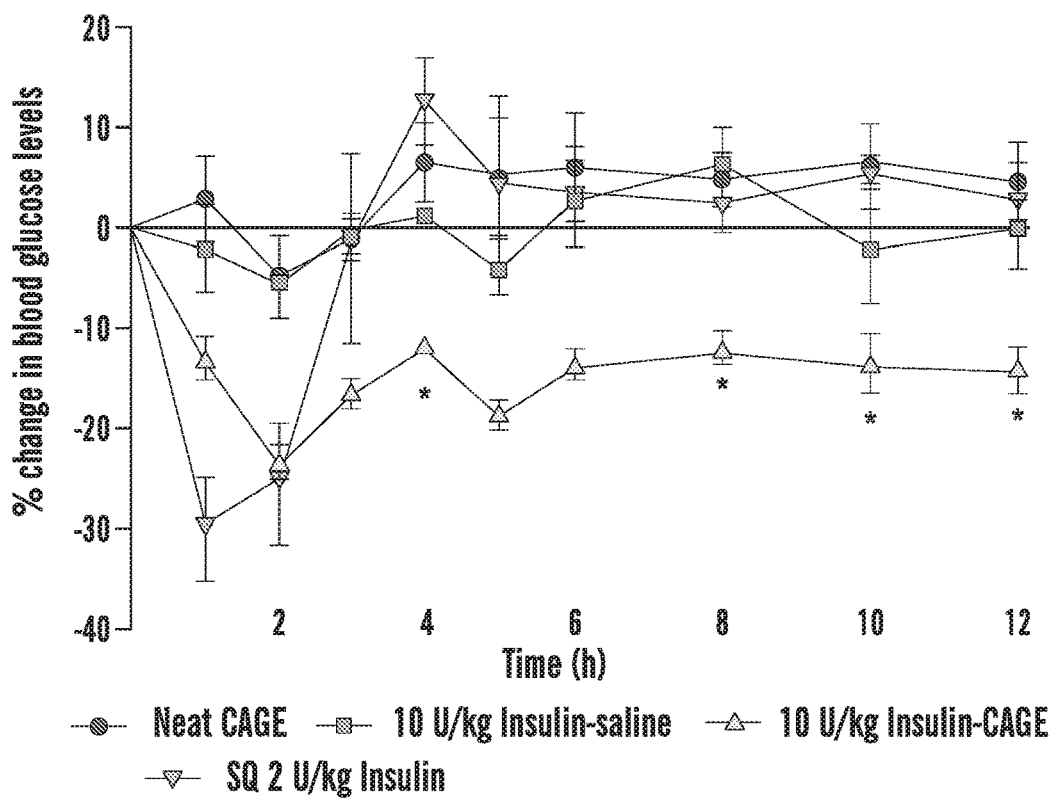

The group treated with 10 U/kg insulin-CAGE demonstrated a rapid 38% drop in blood glucose levels within 2 h post capsule administration (62±2% of initial level) (FIG. 18). Beyond this point, blood glucose dropped slowly but steadily to around 45% at 10 h (55±3%). In comparison, subcutaneous administration of 2 U/kg insulin led to a sharp 49% drop in blood glucose levels (51±5%) in 1 h, which rose steadily and subsequently peaked at 88% of the initial value in 4 h. Thereafter, blood glucose levels dropped in a pattern similar to formulation controls of neat CAGE, empty capsules and insulin-saline. As earlier observed with IJ administration, insulin-CAGE in capsules demonstrated significantly sustained efficacy till the end of study, unlike SQ insulin.

Figure 20:
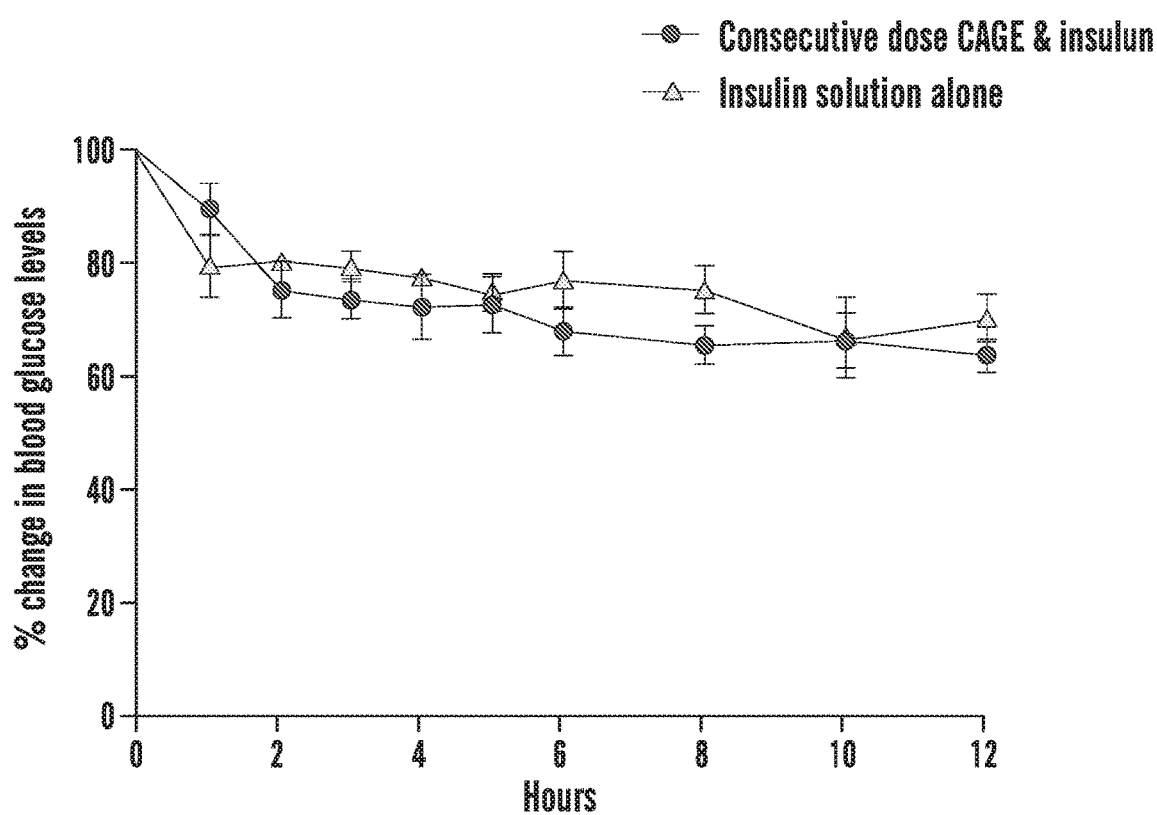
FIG. 20 demonstrates blood glucose lowering efficacy upon consecutive dosing of neat CAGE capsule followed by 10 U/kg insulin capsule after 0.5 h. No significant difference in efficacy was observed between 10 U/kg insulin solution and consecutive capsule dosing of CAGE and 10 U/kg insulin. Data represented as mean±S.E. (n=6).

To assess whether CAGE is acting solely as a permeation enhancer, we administered rats were administered neat CAGE in capsules followed by 10 U/kg insulin powder in capsules after a 0.5 h delay (FIG. 20). A significant difference in efficacy between insulin-CAGE co-administration and consecutive administration was observed in the first few hours of the study (compare FIG. 20 and FIG. 18), while no significant difference between insulin solution (no CAGE) and consecutive dosing of insulin and CAGE was observed through all time points (FIG. 20). The study further indicates that administering insulin and CAGE together provides significant efficacy.

CAGE Demonstrated Good Oral Biocompatibility In Vivo.

Figure 19:
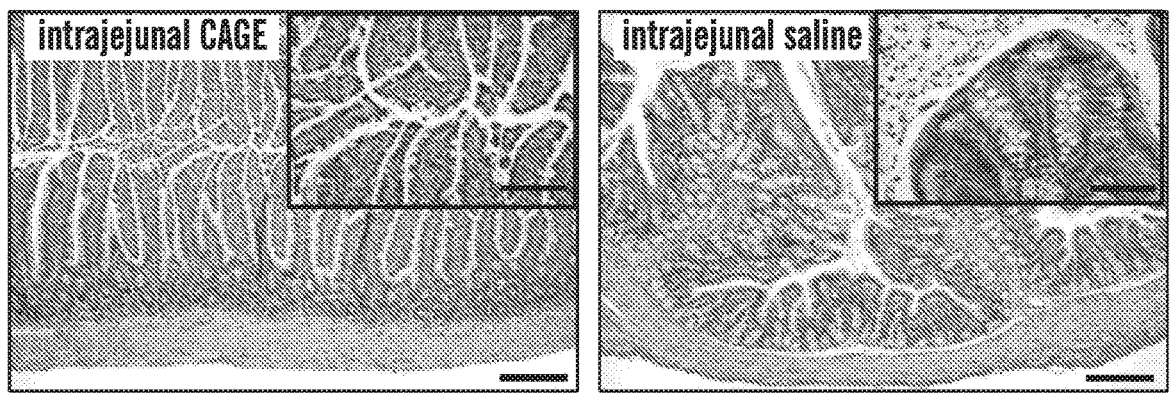
FIG. 19 depicts photomicrographs of hematoxylin and eosin staining of small intestine tissue sections. Sections represent intrajejunal administration of neat CAGE or saline; oral administration of neat CAGE, insulin-saline or insulin-CAGE capsules; and after once a day for 7 day repeat dosing of insulin, CAGE or insulin-CAGE capsules. Scale bar: 200 Inserts are mucosal surface with scale bar of 50 µm.

Histological examination of small intestine samples collected 5 h after intrajejunal administration, 12 h after oral capsule dosing or after 7 days of once-a-day repeat dosing showed no remarkable difference in morphology between CAGE and saline-treated animals/insulin-treated animals (FIG. 19). Additionally, no significant structural damage to the small intestine tissues was noted. Particularly, fingerlike villi were found in all the tissues. The results clearly showcase the excellent biocompatibility of CAGE with intestinal tissue, thereby validating the suitability of the formulation for oral administration.

Discussion

Over the last few decades, the prevalence of diabetes mellitus has grown so steadily that it is now being referred to as the 'epidemic of the century' (14). A rise in diabetes mellitus cases has been reported in every country with the most rapid growth in low and middle-income countries and the largest prevalence in the Middle East and North African regions (14-16). According to a recent World Health Organization report, diabetes was responsible for 1.5 million deaths globally in 2012 with an additional 3.2 million deaths due to hyperglycemia-associated co-morbidities (16). In the United States, 30.3 million people (about 9.4% of the population) were reported suffering from the disease in 2015 and 1.5 million new cases are diagnosed each year (17). Current recommendations for management of the disease include insulin therapy alone or in combination with oral hypoglycemics such as metformin (18). Individuals on insulin therapy alone often require either administration of intermediate-acting insulin two times a day or long-acting insulin once a day (18). Insulin is not available in the clinic as an oral pill and is exclusively administered as a subcutaneous injection. However, despite its effectiveness in the management of hyperglycemia and mitigating risks of neuropathy, nephropathy and retinopathy, injectable insulin has lower patient compliance due to pain, interference with daily activities and embarrassment, resulting in intentional omission and poor long-term glycemic control in as much as 60% of patients (5, 19). This leads to higher hemoglobin A1C levels and increased hospitalization due to diabetes associated complications (19). To circumvent this issue, Mann-Kind Corporation developed an inhalable rapid-acting insulin formulation Afrezza® for post-prandial glycemia management, however it is associated with pulmonary risks such as higher incidences of lung cancer and diabetic ketoacidosis, decreased lung function and higher risk of development of acute bronchospasms in patients with chronic lung disease (20). Given the rapid growth and magnitude of diabetes, it is imperative to develop an insulin therapy that would appeal to patients and avoid formulation-based adverse effects.

Oral delivery enjoys a high patient compliance but is not suitable for delivery of biologics. This is due to the fact that orally delivered drugs need to traverse through the acidic environment of the stomach which can degrade protein/peptide drugs. This can be avoided by encapsulating them in enteric or other protective coated systems. However, upon release in the intestine from their protective casings, peptide/protein drugs are pitched into the proteolytic milieu of the intestine where they are easily cleaved into smaller amino acid units by resident enzymes. If a proportion of the drug escapes proteolysis, its absorption through the intestinal mucus layer and enterocytes into the systemic circulation as an intact molecule is challenging. Oral insulin absorption is further impeded due to erratic GI transit time and lack of specific insulin uptake mechanisms in the intestine (21). A perturbation in insulin structure during GI transit may lead to significant denaturation and loss in biological activity. Therefore, not surprisingly, protein and peptide drugs have a negligible oral bioavailability of less than 1%, a stark divergence from injectable formulations where 100% of the dose is available for pharmacological activity (22). Several researchers have attempted to resolve the perennial problem of low oral bioavailability of insulin by modifying insulin molecules, encapsulating it in novel carriers, or employing enteric coatings, absorption enhancers or proteolytic inhibitors. Some examples include use of poly[lactic-co-glycolic acid] (PLGA) or chitosan-based nanoparticles for oral insulin delivery. Pan et al. obtained a pharmacological bioavailability of 10.3% using 10 U/kg insulin loaded in PLGA nanoparticles and 15.3% using 21 U/kg insulin in chitosan nanoparticles while Cui and co-workers obtained an oral bioavailability of 3.7 and 6.3% using 20 U/kg insulin placed in PLGA and PLGA-55 nanoparticles respectively (23-25). Sarmento and colleagues used chitosan-dextran nanoparticles to encapsulate insulin and observed a pharmacological bioavailability of 5.6 and 3.4% after placing 50 and 100 U/kg insulin respectively in the particles (26). Alginate-chitosan nanoparticles improved oral bioavailability of insulin to 6.8 and 3.4% for 50 and 100 U/kg insulin doses respectively (27). Zhang and co-workers encapsulated 50 U/kg insulin in solid lipid nanoparticles (SLN) and wheat germ agglutinin modified SLN and obtained pharmacological bioavailabilities of 4.5 and 6.1% respectively (28). In the same vein, Ansari et al. reported a five-fold enhancement in oral bioavailability of insulin using SLN compared to orally administered insulin solution (8.3% vs 1.7%) (29). A high oral bioavailability (37.6%) of insulin was achieved by orally delivering insulin in biodegradable polyisobutylcyanoacrylate nanospheres, but high doses of 75 U/kg were used (30). Other strategies of improving oral delivery of proteins involve using proteolytic enzyme inhibitors such as sodium glycocholate, aprotinin, soybean trypsin inhibitor, bacitracin and camostat mesilitate (31). Chemical modifications of insulin such as attaching a targeting ligand like transferrin or cell penetrating peptides like TAT peptide have shown to assist transcytosis of insulin across enterocytes (32, 33). IN-105, an insulin analog obtained through conjugation of a short chain of PEG to insulin has demonstrated an oral dose-dependent reduction in blood glucose postprandially in patients with Type 2 diabetes mellitus through improvement in solubility, stability against proteolytic degradation and intestinal absorption (34, 35). Absorption enhancers include bile salts, surfactants, fatty acids, calcium ion chelating agents, certain polymers such as chitosan/thiolated chitosan and zona occluden toxins that operate by either modulation of the cell membrane structure of intestinal epithelium for transcellular uptake or tight junction permeability for paracellular transport (31).

ILs constitute a group of salts with an organic cation and organic/inorganic anion that are typically liquid below 100° C. (36). Both choline and geranic acid are recognized by the Food and Drug Administration (FDA) as GRAS (Generally Regarded as Safe) ingredients. Choline, an important constituent of lecithin is present in both plants and animals and required for various physiological functions, has an oral lethal dose 50% ($LD_{50}$) of 3,400 mg/kg while geranic acid, commonly used as a flavoring agent in foods has an oral $LD_{50}$ of 3,700 mg/kg in rats (43, 44). Moreover, in a comprehensive review of toxicity of ionic liquids, choline was found to demonstrate the least toxicity amongst various other cationic head groups (45). In this study, the oral CAGE dose after single administration was 80 mg (80 µL) which comprises ~27 mg choline and 53 mg geranic acid. Therefore, a much lower dose than the oral $LD_{50}$ of individual constituents was administered. An adequate choline intake is considered to be 550 mg in men and 425 mg in women per day (46). On the other hand, geranic acid is a common food additive and found in cardamom, lemon grass, petitgrain and other essential oils (47).

CAGE was found to significantly decrease viscosity of mucin hydrogel at 1 and 5% w/v concentrations (FIG. 21) indicating that CAGE assists in mucus penetration in vivo, a key barrier in oral uptake of macromolecules.

In Vivo,

CAGE demonstrated outstanding efficacy in enhancing oral uptake of insulin when administered either intrajejunally or in capsules. Intrajejunally injected 3 U/kg insulin-CAGE led to a 47% drop in blood glucose levels in 5 h, which was comparable to the drop observed with subcutaneously injected 2 U/kg insulin. Using 5 U/kg insulin-CAGE an even more drastic 65% drop in blood glucose levels was observed in 2 h and levels remained significantly lower compared to subcutaneously injected insulin for the remaining period of study. This is one of the lowest oral insulin doses found in the literature demonstrating such remarkable efficacy. Amongst other notable work, Pan and co-workers demonstrated a 52% drop in blood glucose levels in 4 h upon oral administration of 10 U/kg insulin in PLGA particles (24). Using vitamin B12 conjugated dextran nanoparticles loaded with 20 U/kg insulin, Chalasani et al. obtained a 70-75% drop in blood glucose and an oral bioavailability of 29.4% (51). Intrajejunal administration of 10 U/kg insulin in dogs using bile salt mixed micelles exhibited an absolute bioavailability of 1.8% (52). Intrajejunal placement of rectangular mucoadhesive patches loaded with 50 U/kg insulin in rats led to a relative bioavailability of 3.9%. In the presence of permeation enhancer drug dimethyl palmitoyl ammonio propanesulfonate (PPS), the relative bioavailability increased to 7.7% (53). Yin and colleagues showed that intestinal injection of trimethyl chitosan-cysteine conjugate nanoparticles encapsulating 50 U/kg insulin decreased blood glucose levels in rats by 70% (54). Using Labrasol™ to improve oral absorption of insulin, Takada and group observed a bioavailability of 0.25 and 0.2% for intra-ileum and intra-colonic administrations respectively (55). An intragastric delivery of lecithin-based microemulsion containing 200 IU/kg resulted in a bioavailability of 0.148 (without aprotinin) and 0.159 (with aprotinin) in normal rats (56).

Herein, a high jejunal bioavailability of insulin was noted. It is also to be noted that elimination half-life of the insulin-CAGE was almost two-fold higher than subcutaneously injected insulin, indicating a more sustained efficacy. To validate the significant efficacy observed thus far, insulin-CAGE was further encapsulated in enterically coated capsules and administered orally to rats. Enteric coating prevents breakdown of capsules in the acidic environment of the stomach and releases encapsulated material only in the more alkaline environment of the small intestine (57).

Bypassing the stomach using enteric coating technology therefore prevents degradation of biologics by gastric acids. To account for dose dilution upon release of insulin-CAGE in the intestine, a higher insulin dose (10 U/kg) was used than that used in the IJ delivery. Again, insulin-CAGE produced a similar extent of blood glucose drop compared to subcutaneously injected insulin. However, unlike SQ insulin, the effectiveness of insulin-CAGE was sustained till the end of study at 12 h, demonstrating suitability for a long acting oral insulin formulation. Administration of neat CAGE followed by insulin after 0.5 h did not result in any significant blood glucose lowering efficacy (FIG. 20). This indicates that co-administration of insulin and CAGE is required for achieving significant in vivo efficacy.

In addition to high efficacy, CAGE exhibited biocompatibility and long-term stability for potential application in the clinic (FIG. 19). For safety determination in vivo, small intestine sections of rats treated with neat CAGE or insulin-CAGE either after single dose or once-a-day repeat dose administration for a week were isolated and it was found that there was no toxicity at the morphological level after intrajejunal or oral administration, demonstrating excellent oral tolerability of CAGE in vivo.

Insulin-CAGE was stable at RT for 2 months and at 4° C. for at least 4 months as assessed through secondary structure and in vivo bioactivity evaluation (FIGS. 15 and 10). Physico-chemical degradation of insulin occurs primarily due to hydrolysis, aggregation and intermolecular transformation reactions leading to loss of potency (60). Ionic liquids can prevent interaction of proteins with water molecules while protic ionic liquids have been reported to stabilize several amino acids as well as insulin's native conformation and mitigate its self-aggregation propensity (59, 61). Without wishing to be bound by theory, it is contemplated herein that storage of insulin with neat CAGE prevented interaction of the protein with water, mitigating hydrolytic interaction and stabilizing its alpha-helical secondary structure. Given that the monomeric form of insulin is the bioactive form, the enhanced oral bioactivity of insulin in CAGE may also be partly attributed to presentation of insulin molecules to intestinal cells and systemic circulation as monomers.

Overall, described herein is the development of a highly effective oral insulin formulation that has tremendous potential for clinical use. Insulin-CAGE can be prepared effortlessly in a single-step process and therefore can be easily scaled-up for industrial production. The product does not require modification in insulin structure or development of complex nanostructures and therefore precludes generation of immunological reactions to modified protein or loss of active ingredient during multi-step formulation development. Moreover, it is a simple and robust formulation comprising only insulin and an ionic liquid made of GRAS ingredients that eliminates the necessity to use any additives to enhance efficacy. The formulation demonstrated profound efficacy in vivo at very low insulin doses. By delivering insulin-CAGE in enterically coated capsules, we evade gastrointestinal degradation of insulin and enhance its intestinal permeability, thereby overcoming the barriers of oral delivery of biologics. Furthermore, the formulation is biocompatible and has good long-term stability. Outcomes of this study can facilitate realization of oral insulin delivery in the clinic.

Materials and Methods

Materials.

Geranic acid, choline bicarbonate, dimethyl sulfoxide (DMSO), FITC-insulin, FITC-dextran, sodium caprate (98% purity), mucin, and human insulin were purchased from Sigma-Aldrich (St. Louis, Mo., USA), while bovine trypsin was obtained from MP Biomedicals (Santa Ana, Calif., USA). Caco-2 human colorectal adenocarcinoma cells were bought from American Type Culture Collection (Manassas, Va., USA) while Dulbecco modified eagle medium (DMEM) with or without phenol red, fetal bovine serum (FBS), penicillin/streptomycin (P/S) solution, Hank's balanced salt solution (I-BSS), Dulbecco's phosphate buffered saline (DPBS) and 0.25% trypsin solution were purchased from Thermo Fisher Scientific (Waltham, Mass., USA). Intestinal epithelium growth medium comprising basal seeding medium (BSM), enterocyte differentiation medium (EDM) and MITO+ serum extender was purchased from Corning (Corning, N.Y., USA). Millicell®-PCF cell culture inserts (3.0 μm pore size, 12 mm diameter) and TEER measuring device, Millicell®-ERS were obtained from Millipore Sigma (Burlington, Mass., USA) while TEER measuring electrodes were obtained from World Precision Instruments, Inc (Sarasota, Fla., USA). Paraformaldehyde (16% w/v) and metoclopramide hydrochloride were purchased from Alfa Aesar (Ward Hill, Mass., USA) and Vectashield Hardset™ with 4',6-diamidino-2-phenylindole, dihydrochloride (DAPI) was obtained from Vector laboratories Inc. (Burlingame, Calif., USA). 3-(4,5-dimethylthiazol-2-yl)-2,5-diphenyltetrazolium bromide (MTT) cytotoxicity kit and human insulin ELISA kit were obtained from ThermoFisher Scientific (Waltham, Mass., USA). Male Wistar rats weighing between 200-300 g were purchased from Charles River Laboratories (Wilmington, Mass., USA) and blood glucose measuring meter (Aimstrip plus) along with its strips were purchased from Fisher Scientific (Pittsburgh, Pa., USA). Capsule oral gavage and size 9 elongated capsules were obtained from Torpac (Fairfield, Mass., USA). Hematoxylin and eosin solutions were purchased from Sigma Aldrich (St. Louis, Mo., USA). All other reagents used were of analytical grade.

Preparation of CAGE and Insulin-CAGE.

CAGE was synthesized as per our previous study (38). Briefly, two equivalents of neat geranic acid (20 g, 0.119 mol) that had been recrystallized at least 5 times in acetone at <−70° C. to remove impurities, were added to one equivalent of choline bicarbonate (80 wt % solution, 12.275 g, 0.059 mol) in a 500 mL round-bottom flask. The mixture was stirred at 40° C. until $CO_2$ evolution ceased, and the water was removed by rotary evaporation at 60° C. for 2 h followed by drying in a vacuum oven for 48 h at 60° C. Physical characterization at 25° C. showed good agreement with previous values. The NMR spectra (collected using a 500-MHz Varian instrument, Palo Alto, Calif.) was also in good agreement with previous preparations: $^1$H NMR (DMSO-$d_6$), δ5.60 (s, 2H), 5.07 (t, J=6.1, 2H), 3.86 (t, J=6.6, 2H), 3.42 (t, J=6.6, 2H), 3.12 (s, 9H), 2.57 (m, 4H), 2.01 (m, 4H), 1.97 (s, 6H), 1.73 (s, 2H), 1.64 (s, 6H), and 1.57 (s, 6H); $^{13}$C NMR (DMSO-$d_6$), δ170.1, 150-1, 131.5, 124.1, 122, 67.6, 55.5, 53.6, 53.5, 32.8, 25.9, and 17.9. Insulin-CAGE was prepared by adding pre-determined amount of insulin powder to specific volume of CAGE, followed by vortexing for 5 min.

Assessment of Insulin Stability in CAGE.

Samples containing human insulin (100 U, 3.5 mg) were suspended in either 1 mL CAGE or phosphate buffered saline (PBS) in 2 mL micro centrifuge tubes and incubated at room temperature (25° C.) or under refrigeration (4° C.). After 1 month, and approximately each month thereafter for 4 months total, samples were centrifuged for 10 min at 10000×g, CAGE was removed via pipette, and the soft insulin pellet was washed with 1 mL PBS and centrifuged again. PBS-CAGE was removed, and the washing/centrifugation steps repeated until the insulin did not form a pellet during centrifugation. The collected insulin was analyzed for its stability using CD and bioactivity in vivo (described in SI). To collect spectra in the far-UV region (190-250 nm) indicating protein secondary structures, CD spectrophotometry (Jasco J-1500, Easton, Md.) was performed with rectangular quartz cells (1 mm path length, Starna Cells, 1-Q-q, Atascadero, Calif.) loaded with 400 µL of sample Determination of Efficacy of Insulin-CAGE Upon Intrajejunal Administration and Evaluation of Pharmacokinetic Parameters.

The efficacy of insulin-CAGE injected intrajejunally was determined in adult non-diabetic male Wistar rats fasted overnight but given free access to water. Fasting prior to anti-diabetic efficacy studies is routinely done (29, 62, 63). It helps avoid fluctuations in the blood glucose levels as a result of eating, which can vary between animals based on the amount and time of food intake. All animal experiments were performed in accordance with the University of California Santa Barbara animal care committee guidelines and to the Guide for the Care and Use of Animals of the Institute of Laboratory Animal Resources, National Research Council. Before the start of the study, the rats were anesthetized, abdominal hair clipped, and the surgery area was prepped using 70% ethanol and betadine. An incision was made in the abdomen to expose the intestine. The jejunum was located and injected with 100 µL of either 3 or 5 U/kg insulin-CAGE or 100 µL of controls. The time zero blood glucose was taken after the intestine was exposed i.e. immediately prior to the injections. Each formulation was tested in 6 rats with the exception of saline which was tested in only 3 rats. Thereafter, intestinal section was placed back into the abdomen and the muscle and skin sutured. Blood glucose was determined using a commercial glucose meter at the beginning and at every 0.5 h till the end of study at 5 h. Loss in body temperature in the animals during anesthesia was prevented by placing the animals on temperature controlled warming pads prior to surgery followed by additional towel cover after surgery. The animals remained anesthetized throughout the study and were euthanized after 5 h. At the end of study at 5 h, the intestinal section around the injection site was removed for further histological examination to determine toxicity, if any. A separate group of 3 rats were subcutaneously injected with 2 U/kg insulin in saline for comparison of efficacy. The results were plotted as % change in blood glucose levels with respect to initial reading vs time. In addition, the saline group was considered as fasting control and graphs were plotted after subtracting blood glucose levels of the saline group. Pharmacokinetics of insulin-CAGE was evaluated by collecting around 250 µL blood in BD Vacutainer® red top tubes (Becton, Dickinson and Company, Franklin Lanes, N.J., USA) at 0, 1, 2, 3 and 5 h from rats injected with 5 U/kg insulin-CAGE intrajejunally, 5 U/kg insulin-saline intrajejunally and 2 U/kg insulin-saline subcutaneously. Standard protocol was followed for separation of serum from whole blood. Briefly, blood samples were left undisturbed at RT for 15-30 minutes to clot, followed by centrifugation at 2,000 g for 10 minutes. The clear supernatant (serum) was then collected into clean tubes, stored in ice during the procedure and subsequently at −20° C. till further analysis of insulin content. For evaluation of insulin concentration in the serum samples, human insulin ELISA was used, and the manufacturer's protocol followed to determine insulin concentration at each time point. Pharmacokinetic parameters such as elimination rate constant ($K_{el}$), half-life ($t^{1/2}$), area under the curve (AUC) and % bioavailability (F) were calculated from serum insulin concentrations vs time plots. Pharmacodynamic bioavailability was calculated using AUC obtained from efficacy plots.

In Vivo Oral Efficacy.

To determine the efficacy of insulin-CAGE administered through the oral route, elongated size 9 capsules were used. These capsules were filled with 80 µL of either 10 U/kg insulin-CAGE, neat CAGE or left empty. Following this, the capsules were enterically coated three times with 12.5% w/v Eudragit® L-100 dissolved in isopropanol. For the oral efficacy study, adult non-diabetic male Wistar rats were fasted overnight but given free access to water. Next day, the capsules were administered to the rats using an oral gavage followed by subcutaneous administration of 5 mg/kg metoclopramide HCl to promote gastric emptying. Blood glucose was thereafter measured using a commercial glucose meter and subsequently every hour till 12 h. Rats were fasted throughout the period of study. A control of 10 U/kg insulin in saline was also tested by orally administrating the formulation as a solution (sans capsule). In addition, the efficacy of subcutaneously injected 2 U/kg insulin-saline was evaluated. For 10 U/kg insulin-CAGE and neat CAGE, a group of 6 rats per formulation was used while 3 rats per group was utilized for studying the efficacy of empty capsules, 10 U/kg insulin solution and 2 U/kg insulin-saline administered subcutaneously. The results were plotted as percent change in blood glucose level vs time. In addition, the empty capsule group was considered as fasting control and graphs were plotted after subtracting blood glucose levels of the empty capsule group. After 12 h of study, rats were euthanized, and small intestinal sections were collected for tissue histology.

Repeat Dose Biocompatibility.

The biocompatibility of CAGE upon repeat dose administration was evaluated after once a day repeat administration of neat CAGE capsules, 10 U/kg insulin-CAGE capsules and 10 U/kg insulin in capsules for a period of 7 days in non-diabetic rats. All animals were euthanized on day 8 and their small intestinal tissue sections collected for tissue histology.

Tissue Histology.

Small intestinal tissue was fixed in 10% buffered formalin, dehydrated in ethanol, and embedded in paraffin. Five-micron cross-sections of intestine tissue was deparaffinized, rehydrated, and stained with Hematoxylin and Eosin. Histological morphology was examined using a light microscope at 10× and 40× magnification (Olympus BX60™ Upright Compound Microscope).

Data Analysis.

All data are presented as mean±standard error (S.E.). For statistical analysis, student's T-test was utilized. Significant difference was considered at p<0.05. All experiments were conducted in at least triplicates.

REFERENCES

1. Fu A Z, Qiu Y & Radican L (2009) Impact of fear of insulin or fear of injection on treatment outcomes of patients with diabetes. *Curr Med Res Opin* 25(6): 1413-1420.
2. Matteucci E, et al (2015) Insulin administration: Present strategies and future directions for a noninvasive (possibly more physiological) delivery. *Drug Des Devel Ther* 9: 3109-3118.

3. Arbit E & Kidron M (2017) Oral insulin delivery in a physiologic context: Review. *J Diabetes Sci Technol* 11(4): 825-832.
4. Fonte P, et al Polymer-based nanoparticles for oral insulin delivery: Revisited approaches. *Biotechnol Adv*
5. Fonte P, Araujo F, Reis S & Sarmento B (2013) Oral insulin delivery: How far are we?. *J Diabetes Sci Technol* 7(2): 520-531.
6. Zijlstra E, Heinemann L & Plum-Morschel L (2014) Oral insulin reloaded: A structured approach. *J Diabetes Sci Technol* 8(3): 458-465.
7. Aguirre T A S, et al (2016) Current status of selected oral peptide technologies in advanced preclinical development and in clinical trials. *Advanced Drug Delivery Reviews* 106(Part B): 223-241.
8. Rogers R D & Seddon K R (2003) Chemistry. ionic liquids—solvents of the future?. *Science* 302(5646): 792-793.
9. Shamshina J L, Barber P S & Rogers R D (2013) Ionic liquids in drug delivery. *Expert Opin Drug Deliv* 10(10): 1367-1381.
10. Lei Z, Chen B, Koo Y M & MacFarlane D R (2017) Introduction: Ionic liquids. *Chem Rev* 117(10): 6633-6635.
11. Banerjee A, Ibsen K, Iwao Y, Zakrewsky M & Mitragotri S (2017) Transdermal protein delivery using choline and geranate (CAGE) deep eutectic solvent. *Adv Healthc Mater* 6(15): 10.1002/adhm.201601411. Epub 2017 Mar. 24.
12. Zakrewsky M, et al (2016) Choline and geranate deep eutectic solvent as a broad-spectrum antiseptic agent for preventive and therapeutic applications. *Adv Healthc Mater* 5(11): 1282-1289.
13. Huang K, et al (2004) How insulin binds: The B-chain alpha-helix contacts the L1 beta-helix of the insulin receptor. *J Mol Biol* 341(2): 529-550.
14. Kharroubi A T & Darwish H M (2015) Diabetes mellitus: The epidemic of the century. *World J Diabetes* 6(6): 850-867.
15. Olokoba A B, Obateru O A & Olokoba L B (2012) Type 2 diabetes mellitus: A review of current trends. *Oman Med J* 27(4): 269-273.
16. World Health Organization (2016) Global report on diabetes
17. Centers for Disease Control (2017) National diabetes statistics report, 2017. estimates of diabetes and its burden in the united states. *National Center for Chronic Disease Prevention and Health Promotion:* 1-20.
18. McCulloch D K (2017) Patient education: Diabetes mellitus type 2: Insulin treatment (beyond the basics) 2017 (Nov. 8)
19. Peyrot M, Rubin R R, Kruger D F & Travis L B (2010) Correlates of insulin injection omission. *Diabetes Care* 33(2): 240-245.
20. Oleck J, Kassam S & Goldman J D (2016) Commentary: Why was inhaled insulin a failure in the market?. *Diabetes Spectr* 29(3): 180-184.
21. Soares S, Costa A, Fonte P & Sarmento B (2017) in *Drug Delivery: An Integrated Clinical and Engineering Approach*, eds Rosen Y, Gurman P & Elman N (Taylor and Francis,
22. Shaji J & Patole V (2008) Protein and peptide drug delivery: Oral approaches. *Indian J Pharm Sci* 70(3): 269-277.
23. Cui F D, Tao A J, Cun D M, Zhang L Q & Shi K (2007) Preparation of insulin loaded PLGA-Hp55 nanoparticles for oral delivery. *J Pharm Sci* 96(2): 421-427.
24. Pan Y, Xu H, Zhao H Y, Wei G & Zheng J M (2002) Study on preparation and oral efficacy of insulin-loaded poly(lactic-co-glycolic acid) nanoparticles. *Yao Xue Xue Bao* 37(5): 374-377.
25. Pan Y, et al (2002) Bioadhesive polysaccharide in protein delivery system: Chitosan nanoparticles improve the intestinal absorption of insulin in vivo. *International Journal of Pharmaceutics* 249(1): 139-147.
26. Sarmento B, Ribeiro A, Veiga F, Ferreira D & Neufeld R (2007) Oral bioavailability of insulin contained in polysaccharide nanoparticles. *Biomacromolecules* 8(10): 3054-3060.
27. Sarmento B, et al (2007) Alginate/chitosan nanoparticles are effective for oral insulin delivery. *Pharm Res* 24(12): 2198-2206.
28. Zhang N, et al (2006) Lectin-modified solid lipid nanoparticles as carriers for oral administration of insulin. *Int J Pharm* 327(1-2): 153-159.
29. Ansari M J, et al (2016) Enhanced oral bioavailability of insulin-loaded solid lipid nanoparticles: Pharmacokinetic bioavailability of insulin-loaded solid lipid nanoparticles in diabetic rats. *Drug Deliv* 23(6): 1972-1979.
30. Radwan M A (2001) Enhancement of absorption of insulin-loaded polyisobutylcyanoacrylate nanospheres by sodium cholate after oral and subcutaneous administration in diabetic rats. *Drug Dev Ind Pharm* 27(9): 981-989.
31. Wong C Y, Martinez J & Dass C R (2016) Oral delivery of insulin for treatment of diabetes: Status quo, challenges and opportunities. *J Pharm Pharmacol* 68(9): 1093-1108.
32. Shah D & Shen W C (1996) Transcellular delivery of an insulin-transferrin conjugate in enterocyte-like caco-2 cells. *J Pharm Sci* 85(12): 1306-1311.
33. Liang J F & Yang V C (2005) Insulin-cell penetrating peptide hybrids with improved intestinal absorption efficiency. *Biochem Biophys Res Commun* 335(3): 734-738.
34. Khedkar A, et al (2010) A dose range finding study of novel oral insulin (IN-105) under fed conditions in type 2 diabetes mellitus subjects. *Diabetes Obes Metab* 12(8): 659-664.
35. Buckley S T, Hubalek F & Rahbek U L (2016) Chemically modified peptides and proteins—critical considerations for oral delivery. *Tissue Barriers* 4(2): e1156805.
36. Adawiyah N, Moniruzzaman M, Hawatulaila S & Goto M (2016) Ionic liquids as a potential tool for drug delivery systems. *Medicinal Chemistry Communications* 7: 1881-1897.
37. Yang M, et al (2014) Using ionic liquids in whole-cell biocatalysis for the nucleoside acylation. *Microb Cell Fact* 13: 143-014-0143-y.
38. Zakrewsky M, et al (2014) Ionic liquids as a class of materials for transdermal delivery and pathogen neutralization. *Proc Natl Acad Sci USA* 111(37): 13313-13318.
39. Sivapragasam M, Moniruzzaman M & Goto M (2016) Recent advances in exploiting ionic liquids for biomolecules: Solubility, stability and applications. *Biotechnol J* 11(8): 1000-1013.
40. Patel R, Kumari M & Khan A B (2014) Recent advances in the applications of ionic liquids in protein stability and activity: A review. *Appl Biochem Biotechnol* 172(8): 3701-3720.
41. Williams H D, et al (2014) Ionic liquids provide unique opportunities for oral drug delivery: Structure optimization and in vivo evidence of utility. *Chem Commun (Camb)* 50(14): 1688-1690.

42. Sahbaz Y, et al (2015) Transformation of poorly water-soluble drugs into lipophilic ionic liquids enhances oral drug exposure from lipid based formulations. *Mol Pharm* 12(6): 1980-1991.
43. Davis K L, Hollister L E, Vento A L & Simonton S (1978) Choline chloride in methylphenidate- and apomorphine-induced stereotypy. *Life Sciences* 22(24): 2171-2177.
44. Anonymous (1979) Geranic acid. *Food and Cosmetics Toxicology* 17(Supplement): 785-786.
45. Amde M, Liu J F & Pang L (2015) Environmental application, fate, effects, and concerns of ionic liquids: A review. *Environ Sci Technol* 49(21): 12611-12627.
46. Zeisel S H & da Costa K A (2009) Choline: An essential nutrient for public health. *Nutr Rev* 67(11): 615-623.
47. National Center for Biotechnology Information. PubChem Compound Database <br/>3,7-dimethylocta-2,6-dienoic acid. CID=9989. *PubChem Compound Database* 2018 (Apr. 8)
48. Konsoula R & Barile F A (2005) Correlation of in vitro cytotoxicity with paracellular permeability in caco-2 cells. *Toxicol in Vitro* 19(5): 675-684.
49. Krug S M, et al (2013) Sodium caprate as an enhancer of macromolecule permeation across tricellular tight junctions of intestinal cells. *Biomaterials* 34(1): 275-282.
50. Simovic S, Song Y, Nann T & Desai T A (2015) Intestinal absorption of fluorescently labeled nanoparticles. *Nanomedicine* 11(5): 1169-1178.
51. Chalasani K B, Russell-Jones G J, Jain A K, Diwan P V & Jain S K (2007) Effective oral delivery of insulin in animal models using vitamin B12-coated dextran nanoparticles. *J Controlled Release* 122(2): 141-150.
52. Catharine Scott-Moncrief J, Shao Z & Mitra A K (1994) Enhancement of intestinal insulin absorption by bile Salt-Fatty acid mixed micelles in dogs. *Journal of Pharmaceutical Sciences* 83(10): 1465-1469.
53. Gupta V, et al (2016) Oral delivery of exenatide and insulin using mucoadhesive intestinal devices. *Annals of Biomedical Engineering* 44(6): 1993-2007.
54. Yin L, et al (2009) Drug permeability and mucoadhesion properties of thiolated trimethyl chitosan nanoparticles in oral insulin delivery. *Biomaterials* 30(29): 5691-5700.
55. Eaimtrakarn S, et al (2002) Absorption enhancing effect of labrasol on the intestinal absorption of insulin in rats. *J Drug Target* 10(3): 255-260.
56. Cilek A, Celebi N, Tırnaksiz F & Tay A (2005) A lecithin-based microemulsion of rh-insulin with aprotinin for oral administration: Investigation of hypoglycemic effects in non-diabetic and STZ-induced diabetic rats. *Int J Pharm* 298(1): 176-185.
57. Thakral S, Thakral N K & Majumdar D K (2013) Eudragit: A technology evaluation. *Expert Opin Drug Deliv* 10(1): 131-149.
58. Schroder C (2017) Proteins in ionic liquids: Current status of experiments and simulations. *Top Curr Chem (Cham)* 375(2): 25-017-0110-2. Epub 2017 Feb. 7.
59. Micaelo N M & Soares C M (2008) Protein structure and dynamics in ionic liquids. insights from molecular dynamics simulation studies. *J Phys Chem B* 112(9): 2566-2572.
60. Brange J & Langkjoer L (1993) Insulin structure and stability. *Pharm Biotechnol* 5: 315-350.
61. A. Kumar P V (2013) Prevention of insulin self-aggregation by a protic ionic liquid. *Royal Society of Chemistry Advances* 3: 362-367.
62. Lee S, et al (2005) A new drug carrier, nalpha-deoxycholyl-L: -Lysyl-methylester, for enhancing insulin absorption in the intestine. *Diabetologia* 48(3): 405-411.
63. Lee J J, et al (2003) Characterization of streptozotocin-induced diabetic rats and pharmacodynamics of insulin formulations. *Biosci Biotechnol Biochem* 67(11): 2396-2401.

Example 4: Supplemental Material for Example 3

Results

Bioactivity of Insulin Isolated from CAGE was Retained after Long-Term Storage.

To verify long-term stability data of insulin-CAGE obtained using CD, the biological activity of insulin isolated from CAGE at different months in non-diabetic rats was evaluated (FIG. 10). Freshly prepared insulin solution (insulin in saline) brought about a 49% drop in blood glucose levels (51±2%) in 1 h that was sustained in the next hour (50±4%). Blood glucose levels thereafter rose to 92% (92±5%) in 5 h that again slowly declined to about 30% of initial value as a result of continuous fasting. In comparison, insulin isolated from CAGE stored at various temperatures and at different time points followed a similar pattern and drop in blood glucose levels at 1 and 2 h post-injection with no significant difference in percent drop compared to fresh insulin. However, a significantly reduced efficacy was observed for insulin stored at room temperature (RT) for 3 months. In 1 and 2 h after insulin injection a significantly lower 38% drop in blood glucose level was noted (62±2% and 62±3% respectively) in this group, indicating that insulin loses some of its bioactivity after 2 months of storage at RT. However, insulin stored at 4° C. with CAGE, retained its bioactivity for at least 4 months of storage.

Co-Administration of CAGE and Insulin is Required for Significant Therapeutic Efficacy.

When neat CAGE and 10 U/kg insulin were administered separately after 0.5 h, blood glucose dropped slowly and no significant difference was obtained at any time point compared to 10 U/kg insulin solution (FIG. 20). At 10 h of study, blood glucose drop was around 34% of initial levels for both groups (66.3±4.9 and 66.9±7.1% for consecutive dosing and insulin solution respectively). This indicated that CAGE does not cause any long-term permeabilization of intestinal membrane and significant blood glucose lowering efficacy can only be achieved upon co-administration of insulin and CAGE as insulin-CAGE admixture.

Impact of CAGE on Caco-2 Monolayer Viability.

Figure 21:
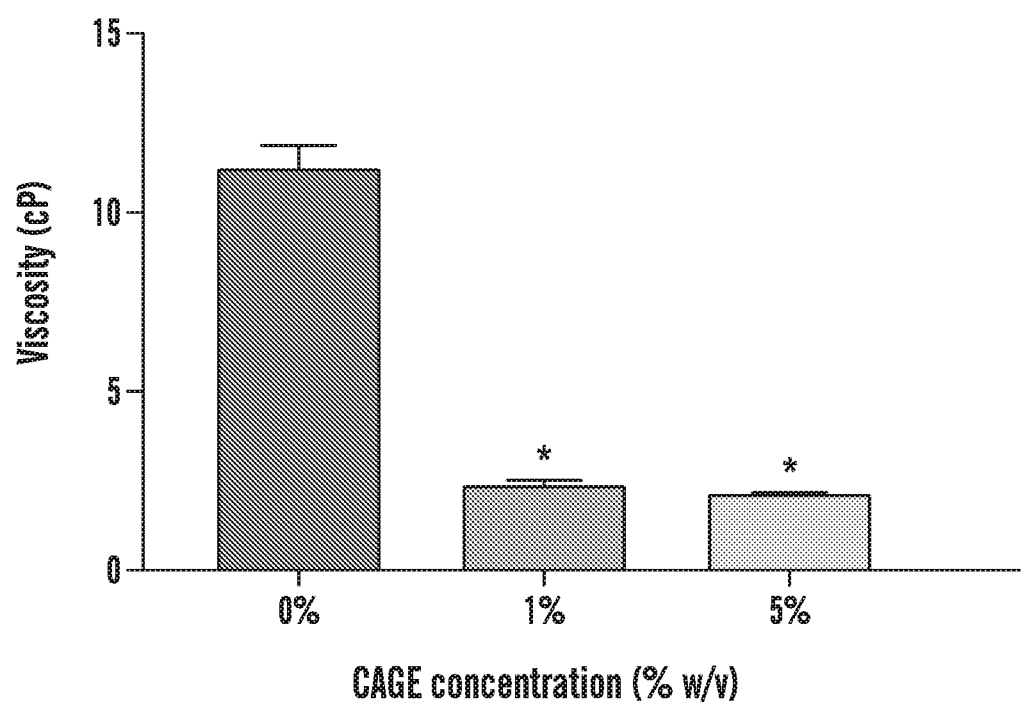
FIG. 21 depicts the reduction in mucus viscosity by CAGE. Mean viscosity values in cP at a shear rate of 50.12 l/s are shown for simulated mucus with no CAGE (0%), 1 and 5% w/v CAGE. Data represented as mean±S.E (n=3); (* p<0.001, CAGE treatment compared to no CAGE treatment).
Figure 22:
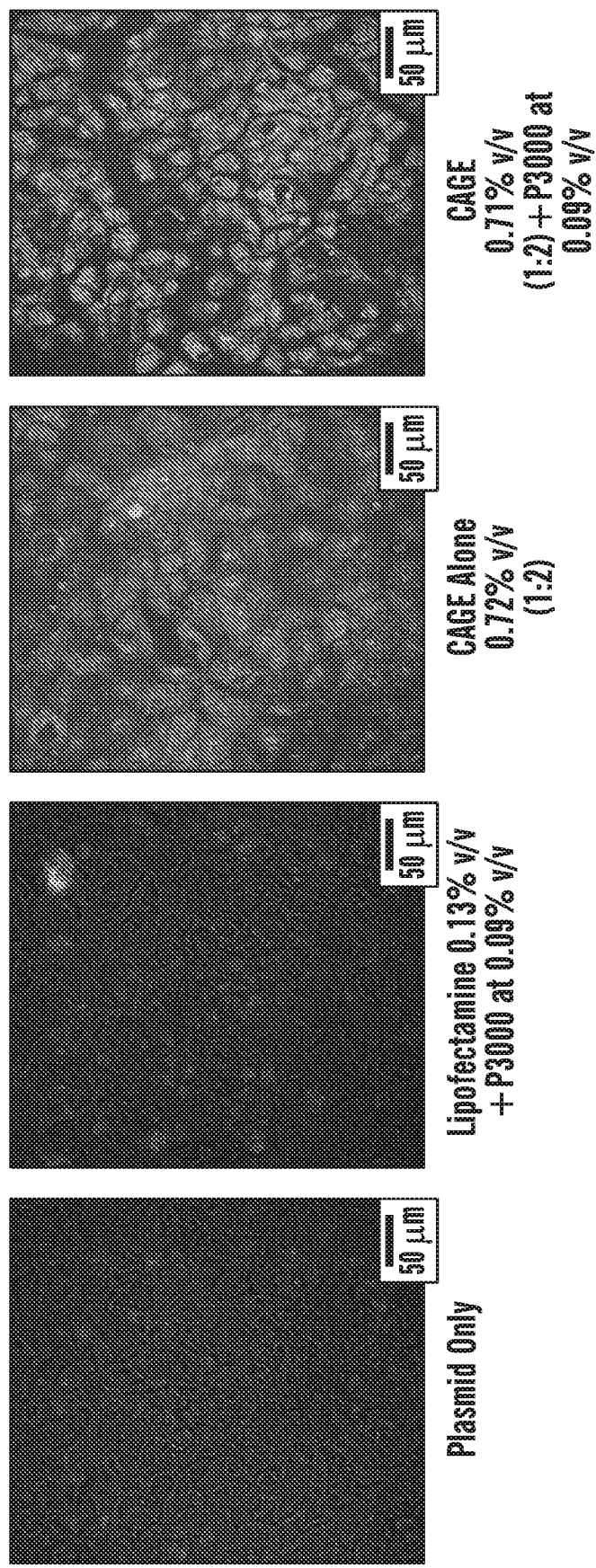
FIG. 22 depicts Confocal Images using GFP-Plasmid. P3000™ Reagent aids in the efficient delivery of the plasmid to the nucleus in conjugation with a delivery vehicle, aiding in improved transfection efficiency. P3000 is most likely a small molecule, not a liposome. Transfection occurred over 3 days before complete media change.
Figure 23:
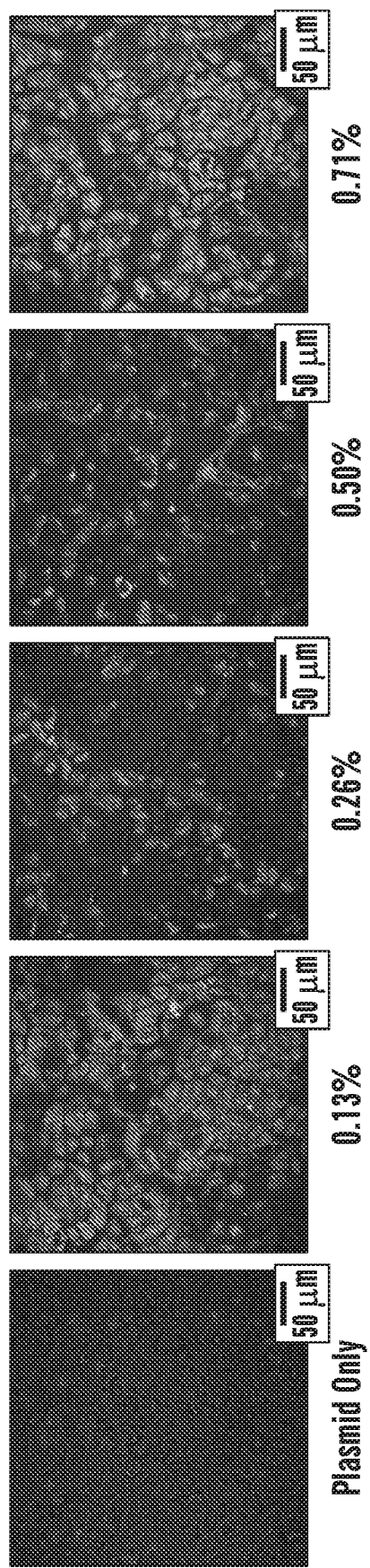
FIG. 23 depicts Concentration Dependence: CAGE (1:2)+ P3000. % refers to CAGE concentration. P3000 (enhancer reagent) concentration kept constant at 0.09% v/v. Transfection occurred over 3 days before complete media change.
Figure 24:
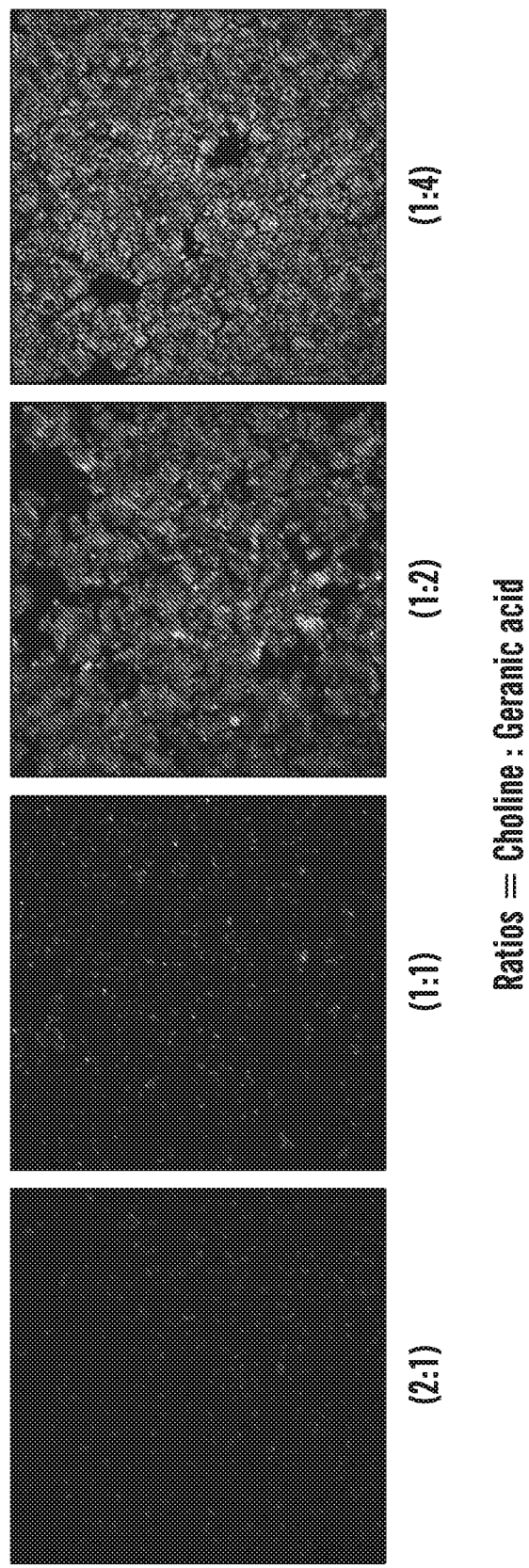
FIG. 24 depicts the effect of CAGE Composition: Concentration of 0.9%. Greatest transfection occurred when excess geranic acid was present (1:2 and 1:4). P3000 enhancer concentration kept constant at 0.09 v/v %. Transfection occurred over 1 day with IL+plasmid before complete media change.
Figure 25:
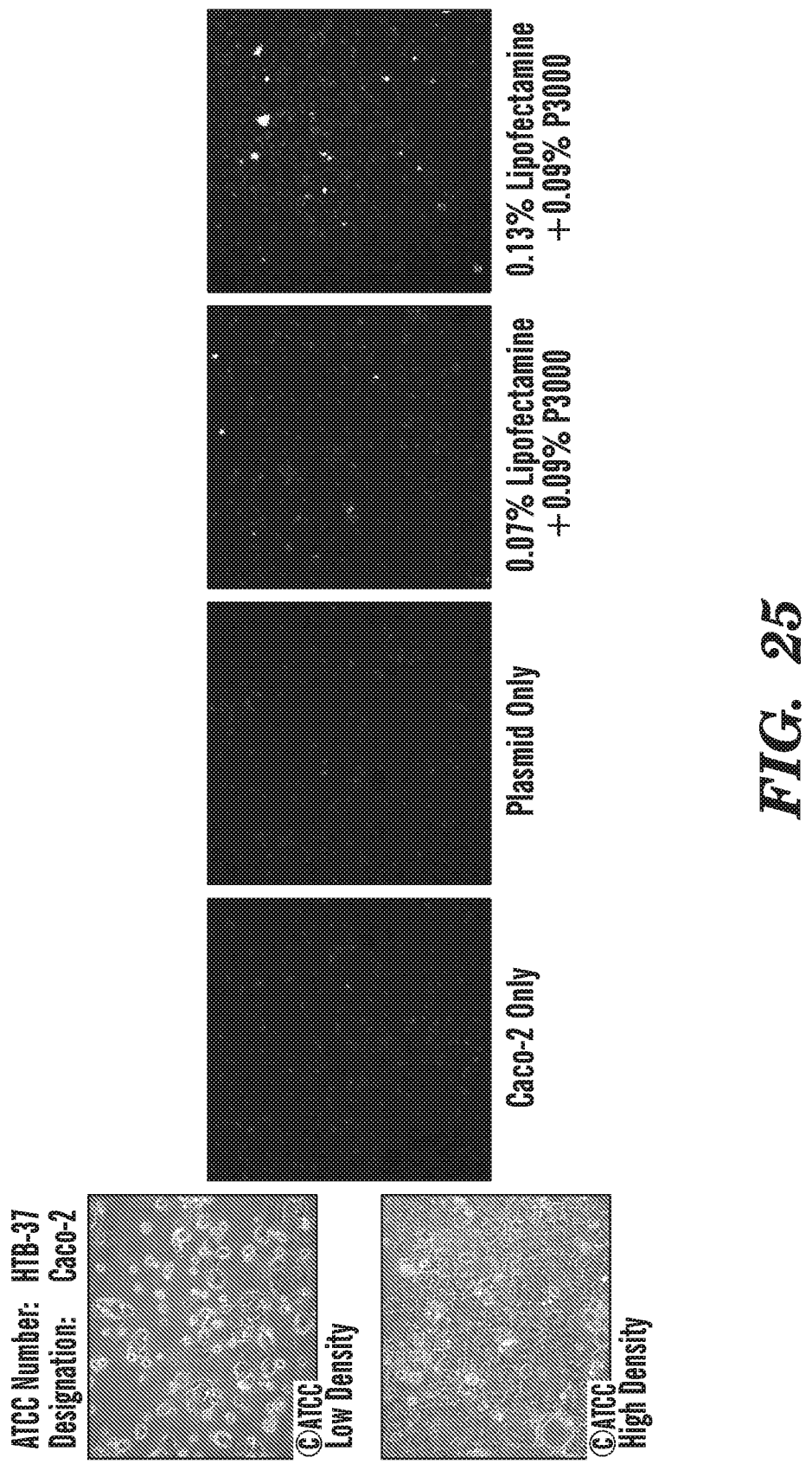
FIG. 25 depicts Confocal Images using GFP-Plasmid: Controls. Transfection occurred over 3 days before complete media change.

Effect of CAGE on Caco-2 intestinal cells was studied in vitro. Cell viability was first determined using MTT (3-(4, 5-dimethylthiazol-2-yl)-2,5-diphenyltetrazolium bromide) cell proliferation assay. Monolayers were exposed to CAGE at various concentrations for 5 h and cell viability values were normalized to no CAGE treatment control (FIG. 21). No adverse effect on cell proliferation was observed with 10 mM CAGE while high cell viability of 86% was obtained using 25 mM CAGE. With 50 mM CAGE, a slightly diminished viability of 69% was obtained.

CAGE Significantly Enhanced Transport of Insulin Across Intestinal Monolayers.

A 5 h-long transport experiment of fluorescein isothiocyanate (FITC)-insulin across Caco-2 monolayers was developed using 0, 10, 25 and 50 mM CAGE. FITC-insulin transport steadily increased with time in both groups throughout the study (data not shown).

These results were corroborated through confocal images of transwell membranes at the end of the study at 5 h. The images clearly show higher uptake of FITC-insulin by Caco-2 cells with increasing concentration of CAGE compared to control cells (data not shown).

CAGE Mediated Drug Transport Across Intestinal Cells is Primarily Paracellular.

Transport of molecules across intestinal epithelia can be either paracellular or transcellular. To evaluate the mechanism by which CAGE enhances transport of drugs across Caco-2 monolayers, both paracellular and passive transcellular transport was investigated in the presence of varying concentrations of CAGE using specific markers for their transport. To this end, the transport of 4 kDa FITC-dextran (specific markers for paracellular transport) was assessed (1).

The transport of 4 kDa FITC-dextran with a size similar to that of insulin was also significantly enhanced in the presence of 25 and 50 mM CAGE (data not shown) at various time points. However, to confirm whether CAGE improved paracellular transport of molecules, the tight junction integrity of Caco-2 cells treated with varying concentrations of CAGE was assessed by measuring trans epithelial electrical resistance (TEER) and comparing it with an established permeation enhancer, sodium caprate (data not shown) (2). In control cells, TEER dropped slightly by ~10% in the first 3 h after which it recovered to its initial value by 5 h and did not change till end of study at 24 h. However, upon treatment with 10 mM CAGE, TEER dropped by 29% in 1 h and was significantly different from control at 1 and 5 h. This TEER drop was found to be transient and the cells completely recovered their tight junction integrity within 24 h.

While TEER drop due to sodium caprate was similar to that of 50 mM CAGE, the tight junction integrity in this group further decreased to 36% of initial levels by the end of study at 24 h. The changes in TEER brought about by 10-25 mM CAGE suggest that at these concentrations, CAGE temporarily opens up the intestinal tight junctions that aid insulin transport across the cells. Other oral absorption enhancement mechanisms mediated by CAGE such as mucus penetration and stability against enzymatic degradation were also subsequently evaluated.

CAGE LED to Mucus Thinning.

CAGE incubated with simulated mucus (SM) resulted in a very significant drop in viscosity (FIG. 21). SM exhibited a similar shear-thinning profile as reported for gastric mucus (4), and the SM viscosity profile compared well to literature values for healthy human duodenal gastric mucus (5). For example, at a shear rate of 46 1/s, the literature value was 12.3 cP compared to the measured SM mean value of 11.3 cP at 50.12 1/s. The addition of 1 and 5% CAGE (23 and 115 mM respectively) reduced the viscosity throughout the entire measured shear range. Viscosity reduction indicates that CAGE would assist in mucus penetration in vivo, thus facilitating delivery of insulin to the intestinal epithelia, while protecting it from proteolytic degradation at the luminal, mucosal and epithelial sites.

Methods

In Vivo Assessment of Long-Term Stability of Insulin in CAGE.

The biological activity of insulin-CAGE stored at RT or 4° C. was evaluated at different months by subcutaneously injecting 1 U/kg insulin isolated from CAGE into adult non-diabetic male Wistar rats. Blood glucose levels were monitored using a commercial glucose meter for 8 h and compared to freshly prepared 1 U/kg insulin solution injected subcutaneously. Prior to insulin injections, rats were fasted overnight but given free access to water and fasting continued throughout the study to eliminate variability in blood glucose due to food consumption. The results were plotted as % change in blood glucose compared to initial level vs time.

Consecutive Dosing of Insulin and CAGE.

Non-diabetic Wistar rats were fasted overnight for 8 h but given access to water ad libitum. Thereafter, rats were orally administered with neat CAGE in enterically coated capsules followed by 5 mg/kg metoclopramide injection for inducing gastric emptying. The blood glucose for time 0 was evaluated at this point. About 0.5 h later, 10 U/kg insulin powder in enterically coated capsule was administered to the rats. Fasting was continued with free access to water till the end of study at 12 h and blood glucose was evaluated at various time points. The results were plotted as % change in blood glucose compared to initial level vs time.

Caco-2 Monolayer Culture in 96-Well Plate and Transwells.

For transport experiments in transwells, a 3-day rapid Caco-2 growth system was used. Cells were placed in Corning® basal seeding medium (BSM) supplemented with MITO serum+ extender and seeded at density of 400,000 cells/mL on Millicell® PCF inserts placed inside 24-well plates. 500 µL of cells containing medium was placed in apical side while 1000 µL of cell free BSM was put in the basolateral side as per manufacturer recommendation. After 24 h of incubation at 37° C., 5% CO2, the medium was replaced with same volume of enterocyte differentiation medium supplemented with MITO serum+ extender for another 2-4 days. TEER was measured on a regular basis and when it reached above 200 ohms. cm2, indicating sufficient tight junction integrity between cells, transport study was performed.

Caco-2 Cell Viability Evaluation of CAGE.

For this study, Caco-2 cells grown in 96-well plates were used. CAGE was diluted with Dulbecco's modified eagle medium (DMEM) to concentrations ranging from 10-50 mM. Three different sets of CAGE dilutions were made (3 dilution replicates). The media was aspirated from each well and each dilution was dispensed (100 µL per well) into 6 wells (6 cell replicates). Control wells were filled with media only. The cells were incubated with different concentrations of CAGE at 37° C., 5% CO2 for 5 h followed by replacement of media with fresh DMEM. The cells were allowed to grow for an additional 19 h (to a total of 24 h) and cell viability was assessed using MTT assay. MTT powder was mixed with media to a concentration of 0.5 mg/mL, added to each well (100 µL), and incubated at 37° C., 5% CO2 for 4 h. Thereafter, MTT solution was removed and 100 µL of dimethyl sulfoxide (DMSO) was added to each well. The plates were wrapped in foil and shaken for 20 min, then absorbance was read at 570 nm using a microplate reader (M220 Infinite Pro, Tecan Group Ltd, Morrisville, N.Y.). Absorbance readings were normalized using the non-treated cell viability values.

Insulin Transport Assay In Vitro.

Before the start of the experiment, the existing medium in the transwell was replaced with DMEM devoid of phenol red, fetal bovine serum (FBS) and penicillin/streptomycin (P/S) in both the apical (200 µL) and basolateral side (600 µL) and the cells were incubated for 30 minutes. Thereafter, the medium in the apical side was replaced with 200 µL of 500 µg/mL FITC-insulin prepared with or without 10, 25 or 50 mM CAGE and solubilized in DMEM free of phenol red, FBS and P/S. Immediately after addition of FITC-insulin at the apical side, a 100 µL aliquot was withdrawn from the basolateral side and replaced with equal volume fresh DMEM. This was repeated at 1, 2, 3, 4 and 5 h. During the study, the transwell plates were placed inside an incubator at 37° C., 5% CO2 on a shaker rotating at 100 rpm and only taken out to remove aliquots at the aforementioned time periods. After the end of study at 5 h, the FITC-insulin concentration in the aliquots were measured using a plate reader (Tecan, Infinite M1000, Mannedorf, Switzerland) at 495/520 nm excitation/emission wavelengths and plotted as % FITC-insulin transport vs time. Furthermore, TEER was measured at every time point when aliquots were withdrawn from the transwells and plotted as basolateral chamber concentration vs time.

For qualitative analysis of FITC-insulin uptake by Caco-2 cells, the transwells from FITC-insulin transport study were washed two times with HBSS at the end of study, followed by addition of 100 µL of 4% paraformaldehyde and kept at 4° C. overnight. On the next day, paraformaldehyde was aspirated from the wells, membranes washed with PBS two times and the transwell membrane were cut and gently placed on glass slides. Mounting media containing (4',6-Diamidino-2-Phenylindole, Dihydrochloride) DAPI was added to the membranes and covered with cover slips. Confocal imaging of the membranes was taken using Olympus Fluoview™ 1000 Spectral Confocal instrument at 40× magnification.

FITC-Dextran Transport Assay In Vitro.

Before the start of the experiment, the medium in the transwells was replaced with DMEM devoid of phenol red, FBS and P/S in both the apical (200 µL) and basolateral side (600 µL) and the cells were incubated for 30 minutes. Thereafter, the medium in the apical side was replaced with 200 µL of 500 µg/mL of 4 kDa FITC-dextran in DMSO (10% final concentration), prepared with or without 10, 25 and 50 mM CAGE and solubilized in DMEM free of phenol red, FBS and P/S. Immediately after addition of the test article to the apical side, a 100 µL aliquot was withdrawn from the basolateral side and replaced with an equal volume of fresh DMEM. This was repeated at 1, 2, 3, 4 and 5 h. During the study, the transwell plates were placed inside an incubator at 37° C., 5% CO2 on a shaker rotating at 100 rpm and only taken out to remove aliquots at each time point. After the end of study at 5 h, fluorescence in the aliquots with FTIC-dextran concentrations were measured using a plate reader (BioTek Synergy NEO HTS™ microplate reader (Winooski, Vt., USA) at 485/530, 495/520 and 468/568 nm excitation/emission wavelengths, respectively. Calibration solutions for each test article were prepared and analyzed using fluorescence readings for FITC-dextran which was used to plot of basolateral chamber concentration vs time plots.

Effect of CAGE and Sodium Caprate on TEER Values.

Before the start of the experiment, the existing medium in the transwell was replaced with DMEM devoid of phenol red, FBS and P/S in both the apical (200 µL) and basolateral side (600 µL) and the cells were incubated for at least 30 minutes. TEER values were recorded for each insert. Thereafter, the medium in the apical side was replaced with 200 µL of either 10, 25 and 50 mM CAGE or 10 mM sodium caprate. During the study, the transwell plates were placed inside an incubator at 37° C., 5% CO2 on a shaker rotating at 100 rpm and only taken out to perform additional TEER measurements at 1, 2, 3, 4, 5 and 24 h. TEER was plotted as % change from initial value vs time.

Interaction of CAGE with Mucin.

Simulated mucus was made by mixing 2% dried pig mucin with saline and vortexing until the mucin was completely dissolved. About 1 and 5% of CAGE (23 and 115 mM respectively) were added to the SM and viscosity was measured across a shear rate range of 1-100 l/s at 25° C. using an AR-G2 rheometer with a 40 mm diameter aluminum 2° cone geometry (TA Instruments, New Castle, Del., USA).

Example 5

GFP Plasmid Transfection Protocol

Caco-2 cells were seeded at 80% confluency in either 96-well half area or 24-well tissue culture treated plates a day prior to adding transfection reagents. For lipofectamine transfection studies, Lipofectamine 3000 reagent (final concs. 0.07% or 0.13%) was prepared in Opti-Mem Medium and mixed. A master mix of plasmid DNA was prepared separately by diluting the GFP plasmid (50 ng/well for 96-well half area plate or 250 ng/well for 24-well plate) in Opti-Mem Medium with P3000 enhancer reagent (final conc. 0.09% v/v). The master mix of plasmid DNA was added to tubes of the diluted lipofectamine 3000 reagent at a 1:1 ratio. The mixture was allowed to incubate for 20 minutes at room temperature to allow for the plasmid to become incorporated into the cationic lipofectamine. The DNA-lipid complex mixture was then added directly to cells in complete cell culture media at final concs. of 0.07% or 0.13%. Total volume of 96-well half area plate was 100 uL and for the 24-well plate 500 uL. This transfection mixture was removed after 3 days of incubation, washed with DPBS, and replaced with complete DMEM cell culture media.

The same protocol as above was used with different variants of CAGE (1:1, 1:2, 1:4, 2:1) at final concs. of 0.13%, 0.26%, 0.5%, 0.71%, and 0.9% in lieu of lipofectamine 3000. If P3000 enhancer reagent was used, the final conc. was maintained at the same 0.09%. The transfection mixtures were removed after 1 day or 3 days, washed with DPBS, and replaced with complete DMEM cell culture media.

Confocal microscopy was used to image for presence of GFP expression (FIGS. 22-25). This data demonstrates that CAGE can deliver DNA into cells.

Example 6: Nanostructure Transitions in Hydrated CAGE

Ionic liquids such as Choline and Geranic Acid Eutectic (CAGE) have found exciting biomedical applications, however, their structure under hydrating conditions is poorly understood. Described herein are the hydration-induced and component-dependent transitions in the nanostructure of a model amphiphilic deep eutectic solvent, CAGE. Wide-angle X-ray scattering and cryo-transmission electron microscopy confirmed nanoscale morphological transitions. Hydration disrupted the native molecular and ionic clusters, reorganizing the polar and non-polar domains, cation and anions alternations, and atom adjacency. At a high degree of hydration (>75% H2O) the nanoscale clusters self-assembled into vesicles, micelles, or microemulsion depending on the concentration and composition. These nanoscale morphological changes also led to changes in macroscopic behavior. Specifically, hydrated CAGE underwent a transition from a Newtonian solvent to a shear-thinning non-Newtonian gel at higher molar ratios of geranic acid. These results demonstrate that the nanostructures of ionic liquids can be tuned by controlling their hydration and molar ratios of the components, presenting new approaches to customise these materials for specific applications.

Deep Eutectic Solvents (DESs) are a special category of ionic liquids formulated by mixing Lewis or Brønsted-Lowry acids and bases in varied molar ratios.[1-3] DESs are a complex assembly of nonsymmetric molecular and ionic clusters linked by coordinating or hydrogen bonding networks[3-18] that are tuned by the chemistry and/or molar ratio of precursors. Eventually, the nanostructure of DESs depends on the integrity of the coordination or hydrogen-bonding network, and is, therefore, susceptible to hydrogen donors including water.[5] The hydrogen bonding networks make these solvents hygroscopic and water retentive,[5] a characteristic behavior that affects their physicochemical properties. For instance, absorbed water decreases the melting temperature[19] and disrupts the nanostructure of pristine DESs.[5] By definition, the behavior of ILs is dominated by ionic interactions, whereas DESs exhibit a strong contribution from hydrogen bonding. CAGE fits the definition of an IL since it comprises largely ionic species, cholinium and geranate, and has a melting point below 100° C. At the same time, CAGE is not a classical IL since it also contains neutral geranic acid. Classification of systems involving ionic and neutral species is complex, due largely to the limitations of current definitions. Accordingly, the definitions and descriptions of compositions, ionic liquids, and DESs provided herein are to be controlling over how terms may be applied elsewhere in the art.

Previous approaches to deconstruct these interactions focus on wholly hydrophilic DESs such as the archetypal choline chloride/urea[4,5,10,15,17,19,20] or entirely hydrophobic analogs such as those derived from long chain fatty acids salts and long chain fatty acids.[18] Amphiphilic deep eutectic solvents and ionic liquids[3,21] open new opportunities.

Described herein is investigation of hydration-induced and component-dependent nanostructure reorganization of CAGE Using wide-angle X-ray scattering (WAXS), fluorescence spectroscopy, and cryo-transmission electron microscopy, the nanostructure transitions induced by increasing hydration and changing molar ratio of precursors are systematically probed. The pervasiveness of water in chemical and biochemical processes informs the selection of hydration as the model trigger to investigate these transitions. Described herein are remarkable hydration-induced and component-dependent transitions in the nanoscale morphology and rheology that open new applications for CAGE Results and Discussion Described herein a facile synthesis route to a CAGE-x:y; x and y being the molar equivalences of choline and geranic acid, respectively. The synthesis involved mixing hydrophilic choline bicarbonate with various molar equivalences of hydrophobic geranic acid. Varying the concentration of geranic acid permitted the deconstruction of the role of hydrogen bonding interactions, Van der Waals forces and hydrophobicity in the nanostructures of CAGE. The carboxylic acid functional group in geranic acid is well-known for its hydrogen bonding property while the alkenyl tail is hydrophobic and engages in Van der Waals interactions. On the other hand, CAGE variants having higher molar equivalences of choline than geranic acid were avoided since such design will contain bicarbonate, a chemical species that may interfere with the nanostructure, hindering the goal of this study. Overall, the strategy provided herein conveniently permits the study of how hydration disrupts the molecular and ionic clusters in CAGE to induce structural transitions at the nanoscopic level.

Figure 26:
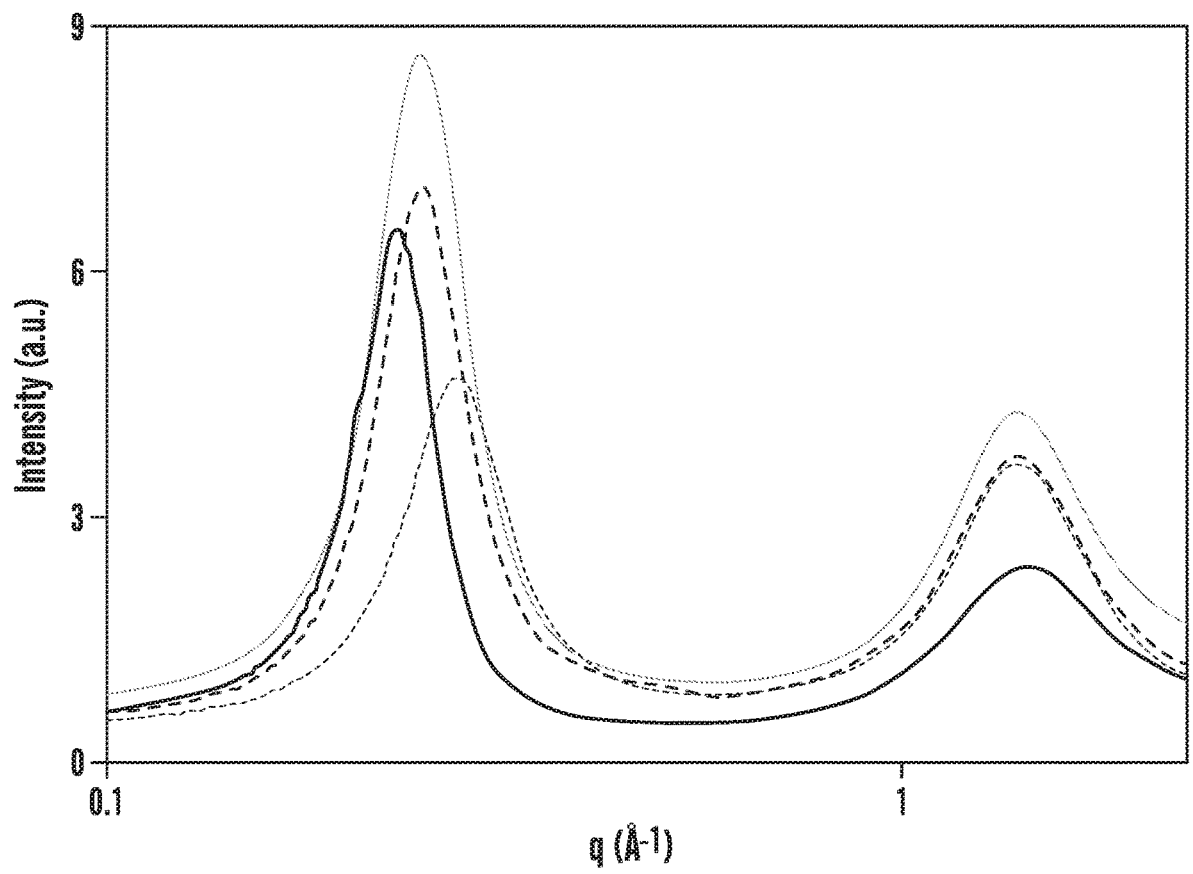
FIG. 26 Wide-angle X-ray scattering patterns for pure CAGE-1:1 (solid black), CAGE-1:2 (solid grey), CAGE-1:3 (black dashed), CAGE-1:4 (grey dashed) at room temperature. The position of the prepeak (low q peak) is sensitive to the molar ratio of geranic acid in CAGE while that of the adjacency peak (high q peak) is insensitive.
Figure 27A:
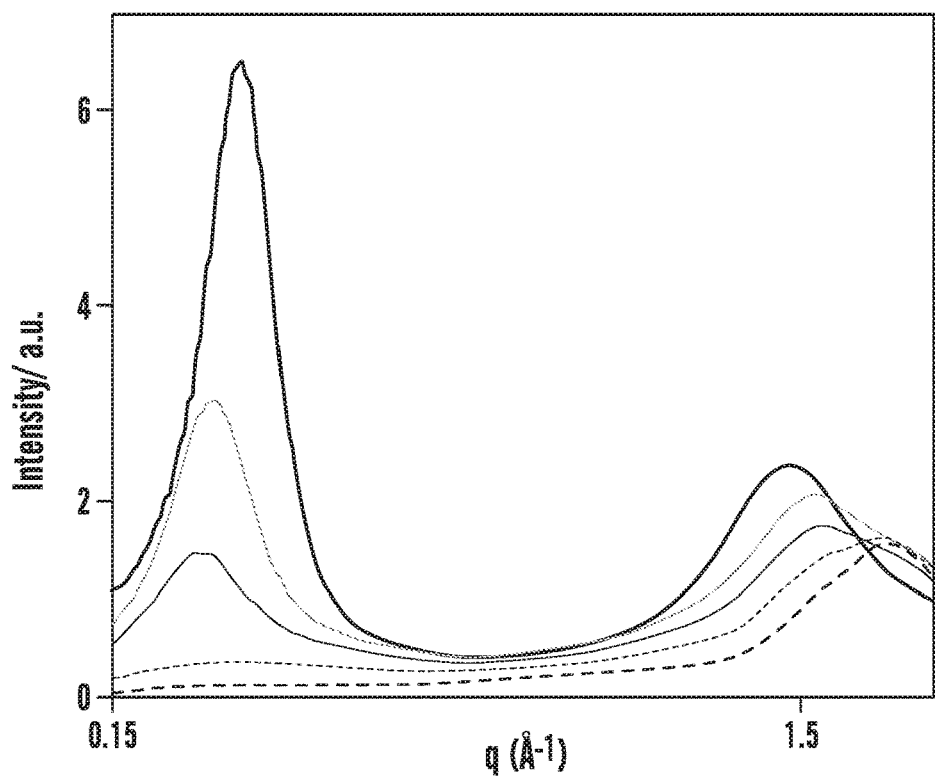
FIGS. 27A-27D depict wide-angle X-ray scattering patterns showing hydration-induced nanostructure transitions in (FIG. 27A) CAGE-1:1, (FIG. 27B) -1:2, (FIG. 27C) -1:3, (FIG. 27D) -1:4 at room temperature. The position and intensity of the prepeak (low q peak) and adjacency peak is sensitive to the amount of water and molar ratio of geranic acid in CAGE. At higher molar ratio of geranic acid as in -1:3 and -1:4, the nanostructure became well-ordered as reflected in the transition from broad to sharp peaks. Heavy black: pure CAGE; solid grey: 75% w/w CAGE; thin black: 50% w/w CAGE; grey/lightly dashed: 25% w/w CAGE; and black/heavily dashed: 5% w/w CAGE.
Figure 27B:
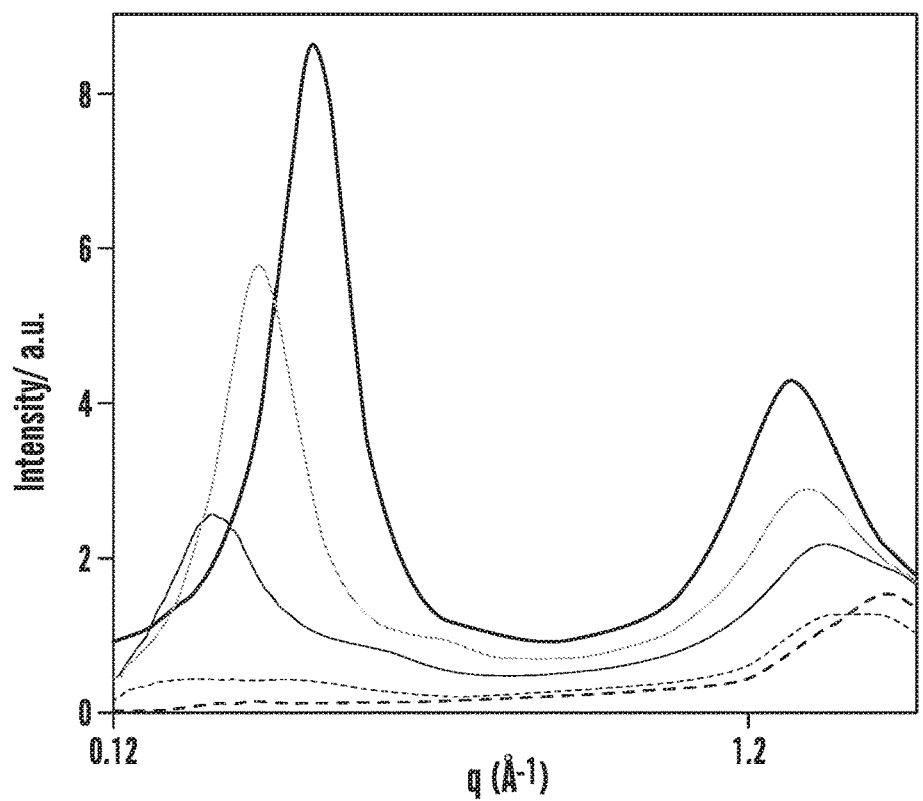
Figure 27C:
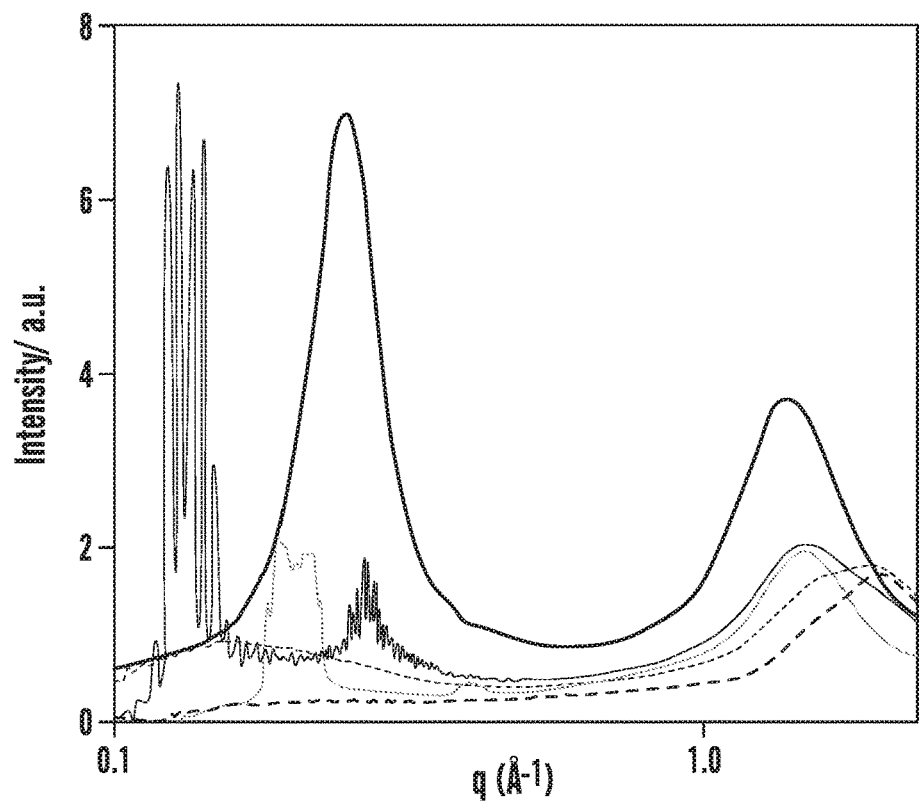
Figure 27D:
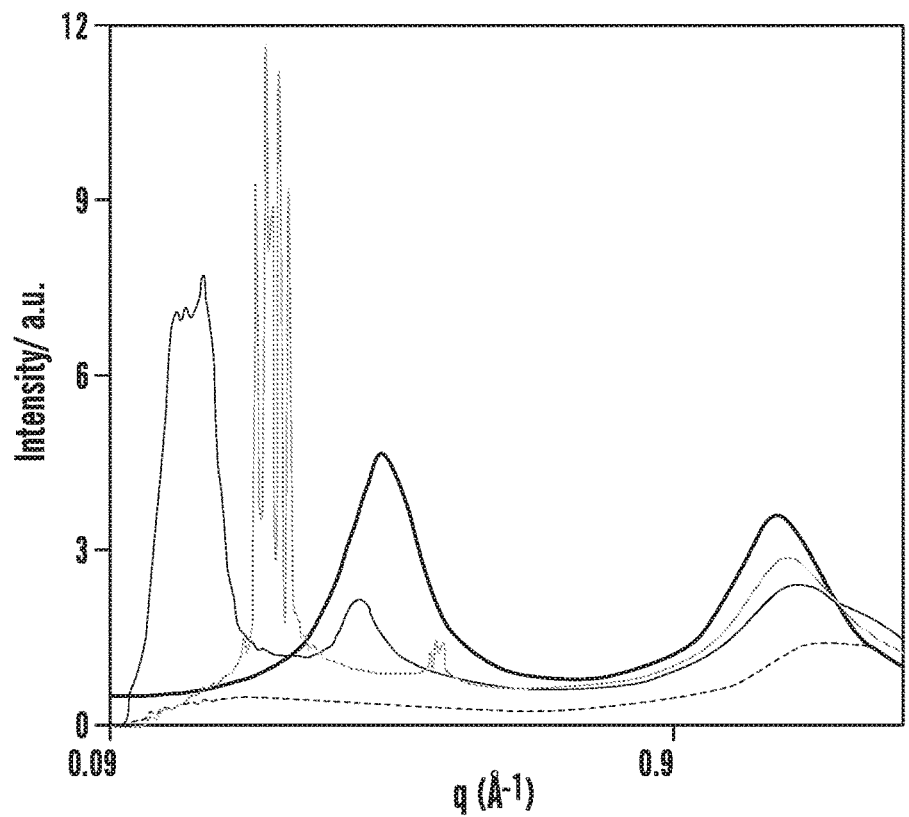

Nanoscale organization of hydrated CAGE was assessed using wide-angle X-ray scattering patterns of the pure CAGE (FIG. 26). All pure CAGE exhibited two prominent scattering peaks at $q=0.22$-$0.28$ Å$^{-1}$ and $q=1.43$ Å$^{-1}$ with the low q peak being sensitive to generic acid concentration (FIG. 26). X-ray scattering profiles of conventional ionic liquids, derived from discrete cations and anions, typically feature three peaks, including a low q "prepeak" due to symmetry from alternating polar and non-polar domains, an intermediate q "charge" peak attributable to alternating cations and anion, and a high q "adjacency" peak arising from inter and intramolecular packing of adjacent atoms.[26-30] Depending on the structure and functional groups on the ionic liquid, the prepeak, charge peak or both could be missing from the scattering profile.[5,28,39,31,32] The low q peak was assigned at 0.22-0.28 Å$^{-1}$ and the high q peak at 1.43 Å$^{-1}$ as prepeak and adjacency peak, respectively. The charge peak was missing from the scattering signal due, perhaps, to cancellation of the peak and antipeak of the subcomponents of the charge peak[28] or absence of alternating discrete cations and anions.

The correlation distance (d) between polar and non-polar domains, calculated from Bragg's law: $d=2\pi/q$, decreased from 27.3 Å to 22.7 Å as the molar equivalence of geranic acid increased from one to four (FIG. 26). This is counter-intuitive since one would expect that increasing geranic acid content will increase the distance between the polar and non-polar domains. Explaining this anomalous behaviour could be complex, but one can rationalize it based on increasing influence of Van der Waals forces on the non-polar alkenyl tail and hydrogen bonding interactions on the polar carboxyl head of the geranic acid at high concentrations. Without wishing to be bound by theory, either or both attractive intermolecular interactions can induce compact packing of the molecular and ionic clusters in the CAGE landscape to decrease d. The observed correlation is peculiar considering that d was previously reported to increase as the non-polar hydrocarbon segment of common ionic liquids increases, specifically when this segment is on the Brønsted base or cation.[26,29,30]

FIGS. 27A-27D depict the WAXS data, which indicate that increasing the degree of hydration, decreased the correlation distance between the polar and non-polar domains. All CAGE variants lost the symmetry due to the alternating polar and non-polar domains as the CAGE concentration dropped to 25% w/w (in other words, 75% hydration) as evidenced by the disappearance of the prepeak (FIGS. 27A-27D). The data imply transitions from the pristine molecular and ionic clusters of the pure CAGE to the liquid structure of water and, importantly, a reorganization of the nanostructure of the CAGE at the inter and intramolecular levels. Without wishing to be bound by theory, it is contemplated that hydration-induced phenomena affecting the polar and non-polar domains, as well as adjacency of atoms, triggers this nanostructure transitions as reflected in changes in intensity and positions of the prepeaks and adjacency peaks (FIGS. 27A-27D). The simultaneous shifts in intensity and position of these peaks are peculiar since increasing hydration decreases only the intensity of the prepeak and has negligible effect on the position of the prepeak or intensity of the adjacency peak.[5,32] Others have reported[27,33] a scenario where disrupting the alternating polar and non-polar domains breaks the symmetry, and ultimately leads to complete disappearance of the prepeak. It is contemplated that the strong hydrogen bonding ability of water with the carboxyl heads of the geranic acid overwhelms and disrupts the attractive Van der Waals forces, segregating the non-polar alkenyl tails at low degree of hydration (<50% H2O, w/w) to increase d and, for thermodynamic reasons, rearranging the pristine nanostructure into different morphologies at high degree of hydration (>75% H2O, w/w) until the symmetry reflected as prepeak disappears.

As the molar ratio of hydrophobic geranic acid to hydrophilic choline increased from one to four, the distance between polar and non-polar domains became more responsive to the effect of hydration. In changing from pure DES to 50% CAGE-water mixture, for instance, the distance between the polar and non-polar domain in CAGE-1:1, -1:2, -1:3, and -1:4 increased by 11%, 37%, 86%, and 88%, respectively. Conversely, the intra and intermolecular distance between atoms, corresponding to the adjacency peak, became less responsive to hydration as demonstrated in CAGE-1:1 and CAGE-1:3 by their 14% and 5% decreases, respectively. The results indicate that adding water to the CAGE segregates the polar and non-polar domains, especially when the molar ratio of the hydrophobic to hydrophilic components is high as in CAGE-1:4 and aggregates the domains when the ratio is low as in CAGE-1:1.

Figure 28:
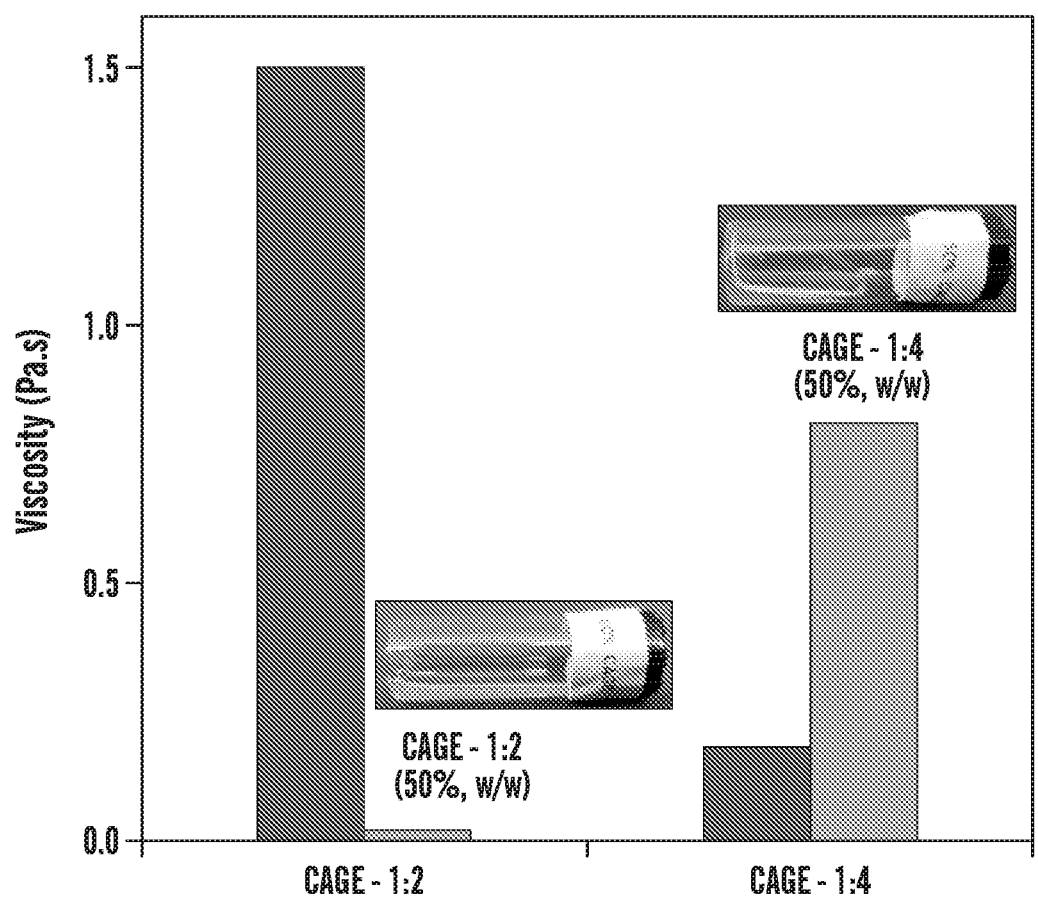
FIG. 28 depicts representative transition in rheological behaviour of pure and 50% hydrated CAGE-1:2 and -1:4 at 25° C. and shear rate of 1 s-1. The viscosity of pure CAGE-1:2 decreased on addition of 50% water while that of pure -1:4 increased. Dark grey: pure; and Light grey: hydrated. Inserts: photographs of less viscous -1:2 (50% H2O, w/w) and gel-like -1:4 (50% H2O, w/w).

The nanostructure transitions in CAGE-1:1 and -1:2 qualitatively differed from those of CAGE-1:3 and -1:4, and therefore, highlight a strong contribution of geranic acid to the nanoarchitecture of the CAGE. Whereas pure and hydrated -1:1 and -1:2 exhibited broad prepeaks and lacked charge peaks, hydrated -1:3 and -1:4 featured sharp multiple scattering prepeaks and charge peaks (FIGS. 27A-27D, 75% w/w and 50% w/w). The transition from broad to sharp peaks in these hydrated -1:3 and -1:4 indicates reorganization of the alternating polar and non-polar domains to a better ordered nanostructure, presumably because of the better alignment of the intermolecular forces in the presence of hydrogen bonding water molecules. Such realignment could affect other macroscopic properties such as viscosity as found in this study (FIG. 28). The near-zero-shear viscosities of 50% hydrated -1:1 and -1:2 were lower than those of their pure analogs, while those of 50% hydrated -1:3 and -1:4 were higher than those of their pure analogs (FIG. 28). Visual examination of the 50% hydrated CAGE-1:4-water mixture reveals a gel-like behavior in contrast with its less viscous pure analog and 50% hydrated -1:2 (FIG. 28). The sol-gel transition of the higher variant, illustrated by CAGE-1:4, provides new possibilities for drug delivery.

Figure 29A:
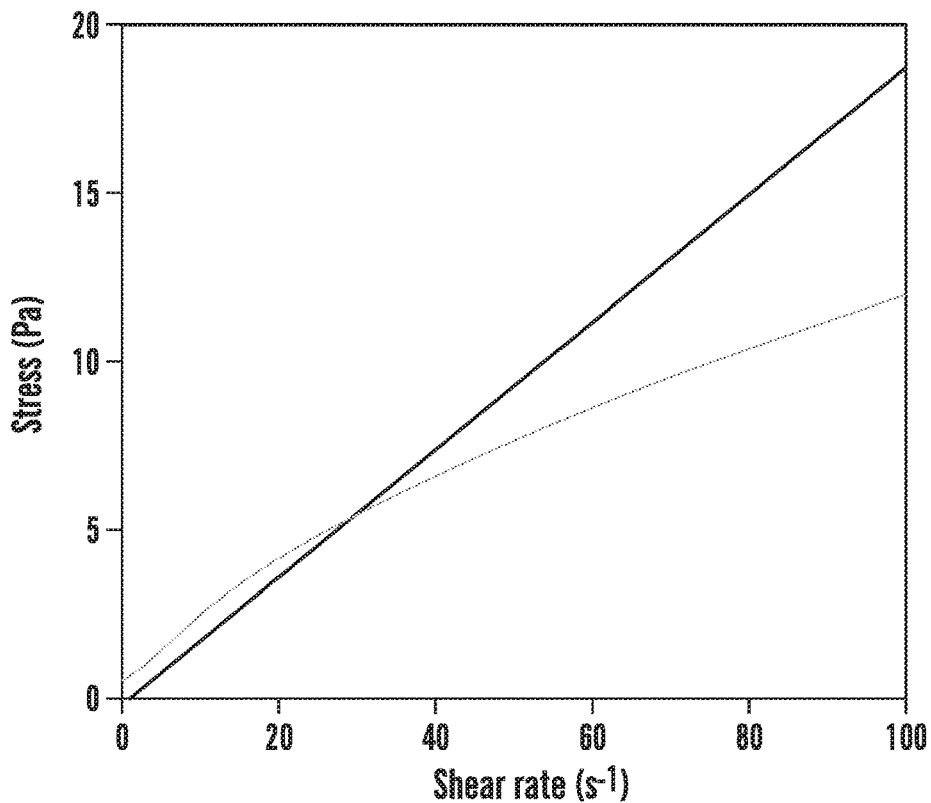
FIG. 29A depicts a graph of the Newtonian property of pure CAGE-1:4 (blue plot) and non-Newtonian property of 50% hydrated -1:4 (red plot).
Figure 29B:
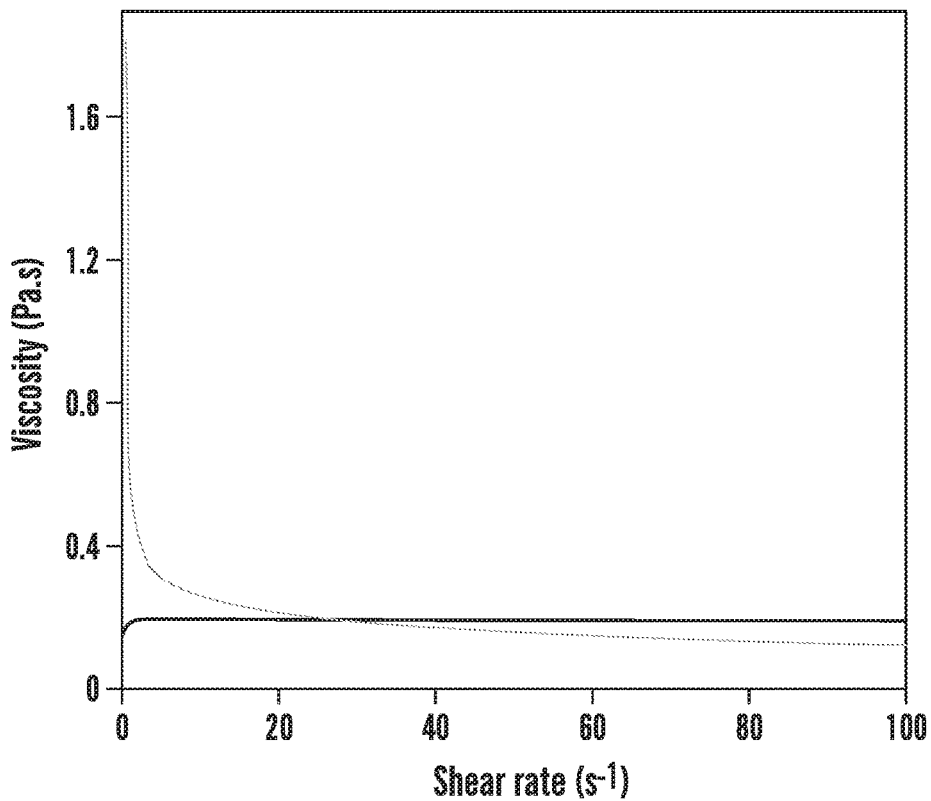
FIG. 29B depicts a graph of shear-thinning behaviour of hydrated 50% hydrated -1:4. Dark grey: pure -1:4; light grey: 50% hydrated -1:4. Rheological experiments carried out at 25° C.
Figure 30A:
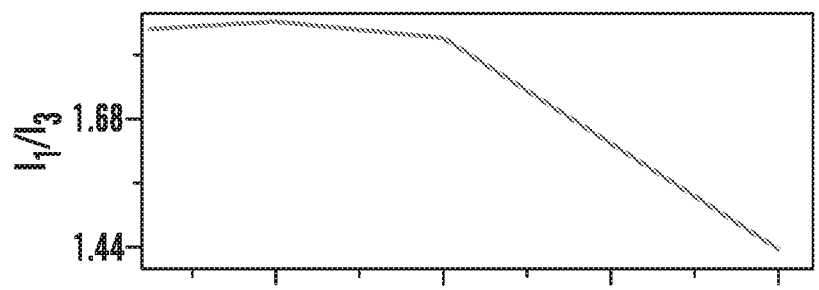
FIGS. 30A-30D depicts plots of ratio of the first (I1) and third (I3) vibronic band of pyrene emission against concentration of (FIG. 30A) CAGE-1:1, (FIG. 30B) -1:2, (FIG. 30C) -1:3, (FIG. 30D) -1:4 showing the CMC, which corresponds to the steep gradient. CAGE-1:3 and -1:4 exhibited two CMCs, presumably due to two self-assembly into two different nanostructures.
Figure 30B:
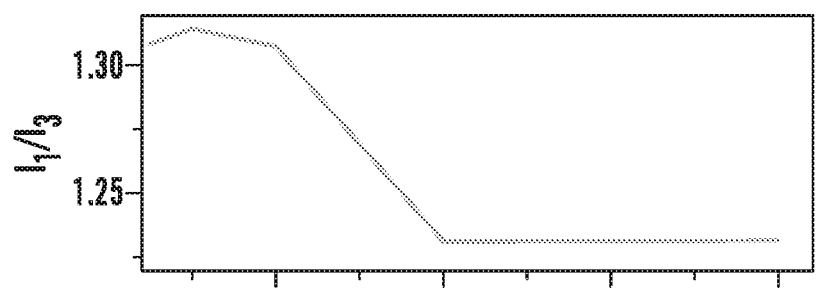
Figure 30C:
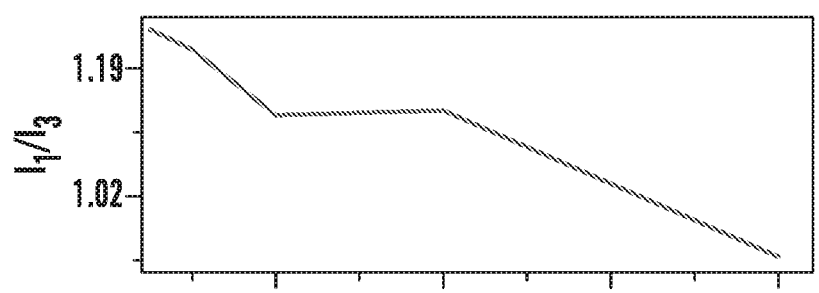
Figure 30D:
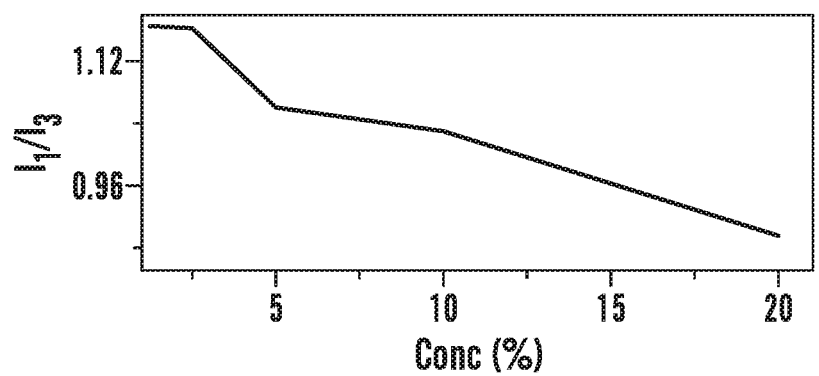
Figure 31A:
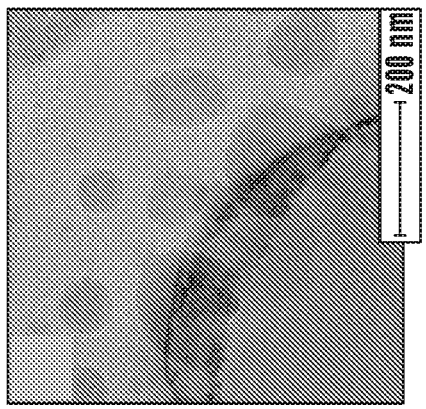
FIGS. 31A-31F depict cryo-TEM micrographs of the DES nanostructures in water. Top panel: Oil-in-water microemulsion of (FIG. 31A) 5%, w/w, CAGE-1:2.
Figure 31B:
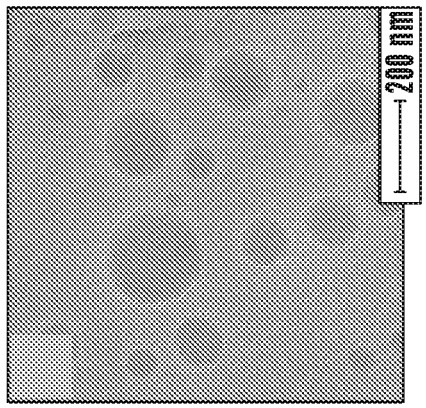
Figure 31C:
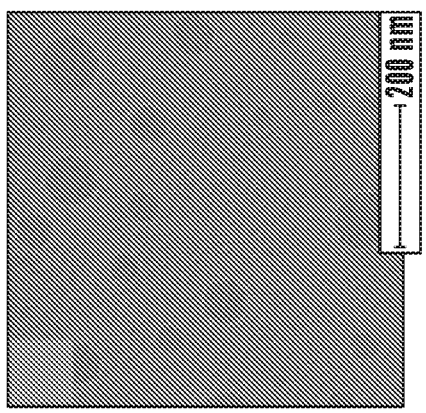
Figure 31D:
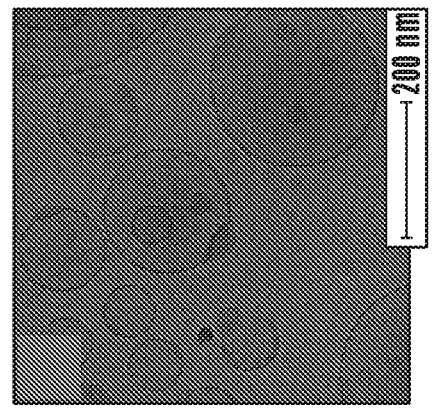
Figure 31E:
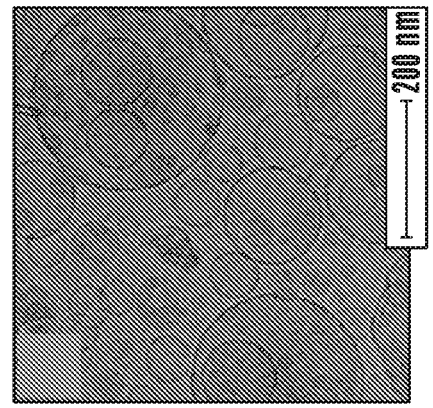
Figure 31F:
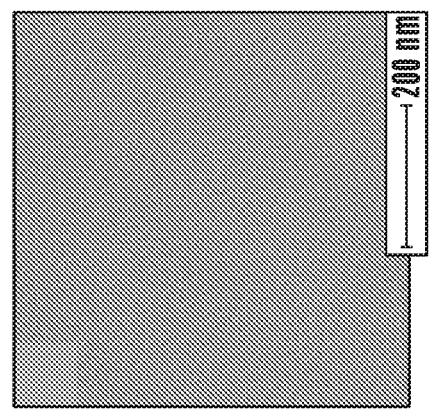

Rheological data indicate that the gel, which is stable for up to 24 hours, exhibited non-Newtonian behaviour, which contrasted with the Newtonian property of the parent CAGE (FIG. 29A). Upon application of increasing shear rates, the viscosity of the gels noticeably decreased (FIG. 29B), apparently due to rupturing of the interconnected hydrogen bonding network. Interestingly, on removal of the shear, the viscosity returned to normal within a finite time, which indicates that rebuilding the ruptured network is fast, and suggest a shear-thinning behavior within the examined shear rates.[34]

All CAGE underwent self-assembly at high degrees of hydration (>75% H2O, w/w) (FIGS. 30A-30D). Based on the intrinsic amphiphilicity of these CAGE variants, self-assembly with increasing hydration was anticipated. Steady-state fluorescence spectroscopic investigation of the pyrene-containing DES-water mixture (>60% H2O, w/w) provides snapshots of the self-assembly by revealing the critical micellization concentrations (CMC) (FIGS. 30A-30D). A prominent change in gradient of a plot of the ratio of the first (I1) to third (I3) vibronic bands in pyrene emission against concentration corresponds to the CMC of the amphiphile. Typically, the plot exhibits a sigmoidal-type profile with the steep gradient corresponding to self-assembly of the amphiphile into well-defined nanostructures with a hydrophobic core into which pyrene preferentially partition. FIGS. 30A-30D show the CMCs and reveals a qualitative difference in the self-assembly processes of the CAGE variants. Compositions with higher geranic acid content, CAGE-1:3 and -1:4, exhibited the lowest CMC (2.5% CAGE, w/w). Qualitatively, the self-assembly process in CAGE-1:1 and -1:2 was different from that for CAGE-1:3 and -1:4. While the former group featured only one prominent slope within the studied concentration range, the latter exhibited two slopes, and therefore two CMCs. The multiple slopes were attributed to transitions in nanostructures of the CAGE in the aqueous medium.

To confirm the assumption, cryo-transmission electron microscopy was used to visually examine the morphologies of the nanostructures in 5% and 20%, w/w, CAGE-water mixtures, concentrations that correspond to different CMCs. A 5%, w/w, CAGE-1:2-, -1:3-, or -1:4-water mixture formed an oil-in-water (o/w) microemulsion (presumably a geranic acid-rich oil phase dispersed in an aqueous phase), which then transitioned into different morphologies as the concentration of the CAGE in the mixture increased to 20% (FIGS. 31A-31F). Evidently, with an increase in CAGE concentration from 5% to 20%, CAGE-1:2 transitioned from characteristic o/w microemulsion morphology[35] into nanostructures that are typical of micelles[36,37] while CAGE-1:3 and -1:4 reorganized into vesicles (FIGS. 31A-31F).

The nanostructure transitions are unusual since very few ionic liquids exhibit this behavior,[38] which is common with some non-ionic surfactant/cosurfactant o/w emulsions.[39,40] In the latter systems, it is hypothesized that, depending on water concentration, o/w droplets nanostructures transition into lamellar structure, which exfoliate into vesicles.[39,40]

The nanostructures of CAGE and their transitions in a concentration- and composition-dependent manner have several fundamental and practical implications. At a fundamental level, these studies provide new insights into the behavior of CAGE at a nanoscale level. Self-assembly is pivotal to many properties in materials science because it drives the reorganization of subcomponents into nanostructures of different morphologies such as lamellae and vesicles. The emerging exploration of amphiphilic CAGE in many chemical and biochemical frontiers creates the need to understand the molecular reorganization induced by water, a most ubiquitous hydrogen donor. This nanostructure reorganization is well-characterised for conventional amphiphilic ionic liquids derived from discrete cations and anions,[26,41-57] but remains unclear for the emerging amphiphilic CAGE.

Understanding of CAGE-water interactions is also important for developing further applications. While the skin environment is rather dry and is unlikely to significantly alter the hydration level of CAGE, the intestinal environment is highly hydrated and will quickly expose CAGE to a high degree of hydration. Understanding the effect of hydration on CAGE properties is thus important in understanding drug transport in these applications as well as in developing its further biomedical applications.

Discussion

It is described herein that the degree of hydration and molar ratio of components are critical to the nanostructure of CAGE. For instance, at 5%, w/w, CAGE-1:4 (95% hydration) formed o/w microemulsion whereas the 20%, w/w (80% hydration), self-assembled into vesicles. The vesicular nanostructures of 20%, w/w, CAGE-1:4 or -1:3 were distinct from the micellar nanostructure of 20%, w/w, CAGE-1:2. The data show that increasing degree of hydration disrupted the native molecular and ionic clusters, leading to a nanoscale reorganization that affected the polar and nonpolar domains, the adjacency of atoms, as well as intra and intermolecular interactions. With a high degree of hydration, >75% $H_2O$, the nanostructures of CAGE self-assembled into vesicles, spheroidal micelles and o/w microemulsion depending on the molar ratio of the precursors. At low molar ratio of the hydrophilic to hydrophobic component, for example in CAGE-1:4, the presence of water, such 50% hydration, induced a sol-gel transitioning due to increasing influence of hydrogen bonding interactions. The data reveal new parameters to tune the nanostructure of CAGE and customize them for specific applications.

Experimental Methods

Materials. Choline bicarbonate (80% in $H_2O$), geranic acid (85%, technical grade), and pyrene (99%, fluorescence grade) were obtained from Sigma Aldrich. Choline bicarbonate and pyrene were used as received from the supplier, and the geranic acid was purified by recrystallisation (5×) from cold (−70° C.) geranic acid-acetone solution (70%, v/v) as previously described.

Preparation of CAGE. CAGE were prepared using a previously described protocol. In brief, an appropriate molar equivalent of choline bicarbonate and recrystallised geranic acid were mixed and stirred at room temperature until evolution of CO2 ceased. As an example, to obtain CAGE-1:2, one molar equivalent of choline bicarbonate was mixed with two molar equivalents of geranic acid. Water, a by-product of the reaction, was removed, first by rotary evaporation at 60° C. for 20 minutes, then in a vacuum oven at 40° C. for 48 hours. This long drying period is adequate to reduce the water content of neat CAGE variances to negligible amount. Hydrated CAGE was prepared by adding an appropriate amount of doubly deionised water to the CAGE, and vortexing for 30 seconds to achieve a consistent mixture.

Wide-angle X-ray Scattering Experiments. SAXSLAB instrument using a Rigaku 002 microfocus X-ray source coupled to an Osmic staggered parabolic multilayer optics and Dectris Pilatus 300K detector was used to acquire WAXS data of CAGE. Hydrated CAGE, containing different percentages of water (0, 25, 50, and 75% $H_2O$, w/w) were loaded into a 1.5 mm capillary tube, sealed with epoxy glue to prevent water absorption or evaporation, then introduced into a large vacuum chamber pumped down to 0.08 mbar. An X-ray wavelength of 0.154 nm and a silver behenate-calibrated sample-to-detector distance of 109.1 mm were used in the experiment. All WAXS experiments were conducted at room temperature. Contribution from a water-filled capillary was subtracted from the scattering profiles of the samples after processing with SAXSGUI v2.15.01 software.

Rheological Experiments. The rheological properties of the CAGE were measured on TA ARES G2 strain-controlled rheometer fitted with a parallel plate geometry (diameter: 50 mm). A flow sweep and flow temperature ramp rheological experiments were carried out on neat and hydrated CAGE (0, 25, and 50% H2O, w/w). Viscosity data were plotted against shear rate and stress to obtain shear thinning and Newtonian behaviour of the CAGE.

Critical Micelle Concentration Determination. Fluorescence spectroscopy with pyrene probe, carried out on Horiba Fluorolog-3 fluorometer, used to determine the critical micelle concentrations (CMCs) of the hydrated CAGE. The CAGE variants were mixed with an appropriate amount of doubly distilled water to obtain CAGE-H2O mixtures (20.0, 10.0, 5.00, 2.50, and 1.25% CAGE, w/w) spiked with pyrene to a concentration of 1×10-6 M. In the fluorescence experiments, the pyrene was excited at 334 nm, emission scanned between 340-550 nm, and the first (I1) at 373 nm and the third (I3) at 384 nm vibronic bands were recorded. The concentration corresponding to the maximum change in the slope of a plot of I1/I3 versus CAGE concentration was taken as the CMC.

Cryo-Transmission Electron Microscope Imaging. For cryo-TEM imaging, we rapidly froze the hydrated CAGE variants (80% and 95% H2O, w/w) in ethane at −80° C. on a Holey Carbon grid and imaged the sample at liquid nitrogen temperature using JEOL 2100 TEM or FEI Tecnai Artica CryoTEM.

REFERENCES

1. Wagle, D. V., Zhao, H., and Baker, G. A. Deep eutectic solvents: sustainable media for nanoscale and functional materials. Acc. Chem. Res. 47, 2299-2308 (2014).
2. Smith, E. L., Abbott, A. P., and Ryder, K. S. Deep eutectic solvents (DESs) and their applications. Chem. Rev. 114, 11060-11082 (2014).
3. McDonald, S., Murphy, T., Imberti, S., Warr, G. G., and Atkin, R. Amphiphilically nanostructured deep eutectic solvents. J. Phys. Chem. Lett. 9, 3922-3927 (2018).
4. Hammond, O. S., Bowron, D. T., and Edler, K. J. Liquid structure of the choline chloride-urea deep eutectic solvent (reline) from neutron diffraction and atomistic modelling. Green Chem. 18, 2736-2744 (2016).
5. Hammond, O. S., Bowron, D. T., and Edler, K. J. The effect of water upon deep eutectic solvent nanostructure: An unusual transition from ionic mixture to aqueous solution. Angew. Chem. Int. Ed. 56, 9782-9785 (2017).
6. Hammond, O. S., Bowron, D. T, Jackson, A. J., Arnold, T., Sanchez-Fernandez, A., Tsapatsaris, N., Sakai, V. G., and Edler, K. J. Resilience of malic acid natural deep eutectic solvent nanostructure to solidification and hydration. J. Phys. Chem. B 121, 7473-7483 (2017).
7. Valvi, A., Dutta, J. and Tiwari, S. Temperature-dependent empirical parameters for polarity in choline chloride based deep eutectic solvents. J. Phys. Chem. B 121, 11356-11366 (2017).
8. Sanchez-Fernandez, A., Hammond, O. S. Jackson, A. J., Arnold, T., Doutch, J., and Edler, K. J. Surfactant-solvent interaction effects on the micellization of cationic surfactants in a carboxylic acid-based deep eutectic solvent. Langmuir 33, 14304-14314 (2017).
9. Passos, H., Tavares, D. J. P., Ferreira, A. M., Freire, M. G., and Coutinho, J. A. P. Are aqueous biphasic systems composed of deep eutectic solvents ternary or quaternary systems? ACS Sustainable. Chem. Eng. 4, 2881-2886 (2016).
10. Pal, M. Rai, R., Yadav, A., Khanna, R., Baker, G. A., and Pandey, S. Self-aggregation of sodium dodecyl sulfate within (choline chloride plus urea) deep eutectic solvent. Langmuir 30, 13191-13198 (2014).
11. Bryant, S. J., Atkin, R., and Warr, G. G. Effect of deep eutectic solvent nanostructure on phospholipid bilayer phases. Langmuir 33, 6878-6884 (2017).
12. Florindo, C., Oliveira, F. S., Rebelo, L. P. N., Fernandes, A. M., and Marrucho, I. M. Insights into the synthesis and properties of deep eutectic solvents based on cholinium chloride and carboxylic acids. ACS Sustainable Chem. Eng. 2, 2416-2425 (2014).
13. Stefanovic, R., Ludwig, M., Webber, G. B., Atkin, R., and Page, A. J. Nanostructure, hydrogen bonding and rheology in choline chloride deep eutectic solvents as a 14. Griffin, P. J., Cosby, T., Holt, A. P., Benson, R. S., and Sangoro, J. R. Charge transport and structural dynamics in carboxylic-acid-based deep eutectic mixtures. J. Phys. Chem. B 118, 9378-9385 (2014).
15. Rumyantsev, M., Rumyantsev, S., and Kalagaev, I. Y. Effect of water on the activation thermodynamics of deep eutectic solvents based on carboxybetaine and choline. J. Phys. Chem. B 122, 5951-5960 (2018).
16. Kaur, S., and Kashyap, H. K. Unusual temperature dependence of nanoscale structural organization in deep eutectic solvents. J. Phys. Chem. B 122, 5242-5250 (2018).
17. Kaur, S., Gupta, A., and Kashyap, H. K. Nanoscale spatial heterogeneity in deep eutectic solvents. J. Phys. Chem. B 120, 6712-6720 (2016).
18. Florindo, C., Celia-Silva, L. G., Martins, L. F. G., Branco, L. C., and Marrucho. I. M. Supramolecular hydrogel based on a sodium deep eutectic solvent. Chem. Commun. 54, 7527-7530 (2018).
19. Meng, X., Ballerat-Busserolles, K., Husson, P., and Andanson, J.-M. Impact of water on the melting temperature of urea plus choline chloride deep eutectic solvent. New J. Chem. 40, 4492-4499 (2016).
20. Sanchez-Fernandez, A., Edler, K. J., Arnold, T., Heenan, R. K., Porcar, L., Terrill, N.J. Terry, A. E., and Jackson, A. J. Micelle structure in a deep eutectic solvent: a small-angle scattering study. Phys. Chem. Chem. Phys. 18, 14063-14073 (2016).
21. Banerjee, A., Ibsen, K., Iwao, Y., Zakrewsky, M., and Mitragotri, S. Transdermal protein delivery using choline and geranate (CAGE) deep eutectic solvent. Adv. Healthc. Mater. 6, 1601411 (2017).
22. Banerjee, A., Ibsen, K. N., Brown, T., Chen, R., Agatemor, C., and Mitragotri, S. Ionic liquids for oral insulin delivery. Proc. Natl Acad. Sci. USA 201722338 (2018).
23. Ibsen, K. N., Banerjee, A., Tanner, E. E. L., Nangia, S., and Mitragotri, S. Mechanism of antibacterial activity of choline-based ionic liquids (CAGE). ACS Biomater. Sci. Eng. Article ASAP (2018).
24. Zakrewsky, M., Banerjee, A., Apte, S., Kern, T. L., Jones, M. R., Del Sesto, R. E., Koppisch, A. T., Fox, D. T., and Mitragotri, S. Choline and geranate deep eutectic solvent as a broad-spectrum antiseptic agent for preventive and therapeutic applications. Adv. Healthc. Mater. 5, 1282-1289 (2016).
25. Zakrewsky, M., Lovejoy, K. S., Kern, T. L., Miller, T. E., Le, V., Nagy, A., Goumas, A. M., Iyer, R. S., Del Sesto, R. E., Koppisch, A. T., Fox, D. J., and Mitragotri, S. Ionic liquids as a class of materials for transdermal delivery and pathogen neutralization. Proc. Natl. Acad. Sci. USA. 111, 13313-13318 (2014).
26. Greaves, T. L., Kennedy, D. F., Mudie, S. T., and Drummond, C. J. Diversity observed in the nanostructure of protic ionic liquids. J. Phys. Chem. B 114, 10022-10031 (2010).
27. Araque, J. C., Hettige, J. J., and Margulis, C. J. Modern room temperature ionic liquids, a simple guide to understanding their structure and how it may relate to dynamics. J. Phys. Chem. B 119, 12727-12740 (2015).
28. Hettige, J. J., Kashyap, H. K., Annapureddy, H. V., and Margulis, C. J. Anions, the reporters of structure in ionic liquids. J. Phys. Chem. Lett. 4, 105-110 (2013).
29. Rauber, D., Zhang, P., Huch, V., Kraus, T., and Hempelmann, R. Lamellar structures in fluorinated phosphonium ionic liquids: the roles of fluorination and chain length. Phys. Chem. Chem. Phys. 19, 27251-27258 (2017).
30. Pott, T., and Méléard, P. New insight into the nanostructure of ionic liquids: a small angle X-ray scattering (SAXS) study on liquid tri-alkyl-methyl-ammonium bis (trifluoromethanesulfonyl) amides and their mixtures. Phys. Chem. Chem. Phys. 11, 5469-5475 (2009).
31. Shen, Y., Kennedy, D. F., Greaves, T. L., Weerawardena, A., Mulder, R. J., Kirby, N., Song, G., and Drummond, C. J. Protic ionic liquids with fluorous anions: physicochemical properties and self-assembly nanostructure. Phys. Chem. Chem. Phys. 14, 7981-7992 (2012).
32. Greaves, T. L., Kennedy, D. F., Weerawardena, A., Tse, N. M. K., Kirby, N., and Drummond, C. J. Nanostructured protic ionic liquids retain nanoscale features in aqueous solution while precursor Brønsted acids and bases exhibit different behavior. J. Phys. Chem. B 115, 2055-2066 (2011).
33. Kashyap, H. K., Santos, C. S., Daly, R. P., Hettige, J. J., Murthy N. S., Shirota, H., Castner, E. W., and Margulis, C. J. How Does the Ionic Liquid Organizational Landscape Change when Nonpolar Cationic Alkyl Groups Are Replaced by Polar Isoelectronic Diethers? J. Phys. Chem. B 117, 1130-1135 (2013).
34. Maestro, A., Gonzalez, C., and Gutierrez, J. M. Shear thinning and thixotropy of HMHEC and HEC water solutions. J. Rheol. 46, 1445-1457 (2002).
35. Kuntsche, J., Horst, J. C., and Bunjes, H. Cryogenic transmission electron microscopy (cryo-TEM) for studying the morphology of colloidal drug delivery systems. Int. J. Pharm. 417, 120-137 (2011).
36. Ruthstein, S., Schmidt, J., Kesselman, E., Talmon, Y., and Goldfarb, D. Resolving intermediate solution structures during the formation of mesoporous SBA-15. J. Am. Chem. Soc. 128, 3366-3374 (2006).
37. Patchornik, G., Wachtel, E., Kesselman, E., Danino, D. Cryo-TEM structural analysis of conjugated nonionic engineering-micelles, Soft Matter, 10, 4922-4928 (2014)
38. Wang, H., Zhang, L., Wang, J., Li, Z., and Zhang, S. The first evidence for unilamellar vesicle formation of ionic liquids in aqueous solutions. Chem. Commun. 49, 5222-5224 (2013).
39. Lee, H. S., Morrison, E. D., Frethem, C. D., Zasadzinski, J. A., and McCormick, A. V. Cryogenic electron microscopy study of nanoemulsion formation from microemulsions. Langmuir 30, 10826-10833 (2014).
40. Fernandez, P., Andre, V., Rieger, J., and Kuhnle, A. Nano-emulsion formation by emulsion phase inversion. Colloid Surf. A Physicochem. Eng. Asp. 251, 53-58 (2004).
41. Celso, F. L., Yoshida, Y., Lombardo, R., Jafta, C., Gontrani, L., Triolo, A., Russina, O. Mesoscopic structural organization in fluorinated room temperature ionic liquids. C. R. Chimie in press (2018).
42. Russina, O., Celso, F. L., Plechkova, N. V., and Triolo, A. Emerging evidences of mesoscopic-scale complexity in neat ionic liquids and their mixtures. J. Phys. Chem. Lett. 8, 1197-1204 (2017).
43. Russina, O., Triolo, A., Gontrani, L., Caminiti, R., Xiao, D., Hines Jr, Bartsch, R. A., Quitevis, E. L., Plechkova, N., and Seddon, K. R. Morphology and intermolecular dynamics of 1-alkyl-3-methylimidazolium bis {(trifluoromethane) sulfonyl} amide ionic liquids: structural and dynamic evidence of nanoscale segregation. J. Phys. Condens. Matter 21,424121 (2009).

44. Russina, O., Triolo, A., Gontrani, L., and Caminiti, R. Mesoscopic structural heterogeneities in room-temperature ionic liquids. J. Phys. Chem. Lett. 3, 27-33 (2012).
45. Triolo, A., Russina, O., Bleif, H.-J., and Di Cola, E. Nanoscale segregation in room temperature ionic liquids. J. Phys. Chem. B 111, 4641-4644 (2007).
46. Triolo, A., Russina, O., Fazio, B., Triolo, R., and Di Cola, E. Morphology of 1-alkyl-3-methylimidazolium hexafluorophosphate room temperature ionic liquids. Chem. Phys. Lett. 457, 362-365 (2008).
47. Triolo, A., Russina, O., Fazio, B., Appetecchi, G. B., Cerewska, M., Passerini, S. Nanoscale organization in piperidinium-based room temperature ionic liquids. J. Chem. Phys. 130, 164521 (2009).
48. Annapureddy, H. V. R., Kashyap, H. K., De Biase, P. M., and Margulis, C. J. What is the origin of the prepeak in the X-ray scattering of imidazolium-based room-temperature ionic liquids? J. Phys. Chem. B 114, 16838-16846 (2010).
49. Li, H., Endres, F., and Atkin, R. Effect of alkyl chain length and anion species on the interfacial nanostructure of ionic liquids at the Au(111)-ionic liquid interface as a function of potential. Phys. Chem. Chem. Phys. 15, 14624-14633 (2013).
50. Atkin, R., and Warr, G. G. The smallest amphiphiles: Nanostructure in protic room-temperature ionic liquids with short alkyl groups. J. Phys. Chem. B 112, 4164-4166 (2008).
51. Hayes, R., Warr, G. G., and Atkin, R. At the interface: solvation and designing ionic liquids. Phys. Chem. Chem. Phys. 12, 1709-1723 (2010).
52. Jiang, H. J., Atkin, R., and Warr, G. G. Nanostructured Ionic Liquids and Their Solutions: Recent Advances and Emerging Challenges. Curr. Opin. Green Sustainable Chem. 12, 27-32 (2018).
53. Hayes, R., Warr, G. G., and Atkin, R. Structure and nanostructure in ionic liquids. Chem. Rev. 115, 6357-6426 (2015).
54. Agatemor, C., Ibsen, K. N., Tanner, E. E., and Mitragotri, S. Ionic liquids for addressing unmet needs in healthcare. Bioeng. Transl. Med. 3, 7-25 (2018).
55. Hayes, R., Imberti, S., Warr, G. G., and Atkin, R. Amphiphilicity determines nanostructure in protic ionic liquids. Phys. Chem. Chem. Phys. 13, 3237-3247 (2011).
56. Jungnickel, C., Luczak, J., Ranke, J., Fernàndez, J. F., Muller, and Thöming, J. Micelle formation of imidazolium ionic liquids in aqueous solution. Colloids Surf A Physicochem. Eng. Asp. 316, 278-284 (2008).
57. Blesic, M., Marques, M. H., Plechkova, N. V., Seddon, K. R., Rebelo, L. P. N., and Lopes, A. Self-aggregation of ionic liquids: micelle formation in aqueous solution. Green Chemistry 9, 481-490 (2007).

Example 7

Figure 32:
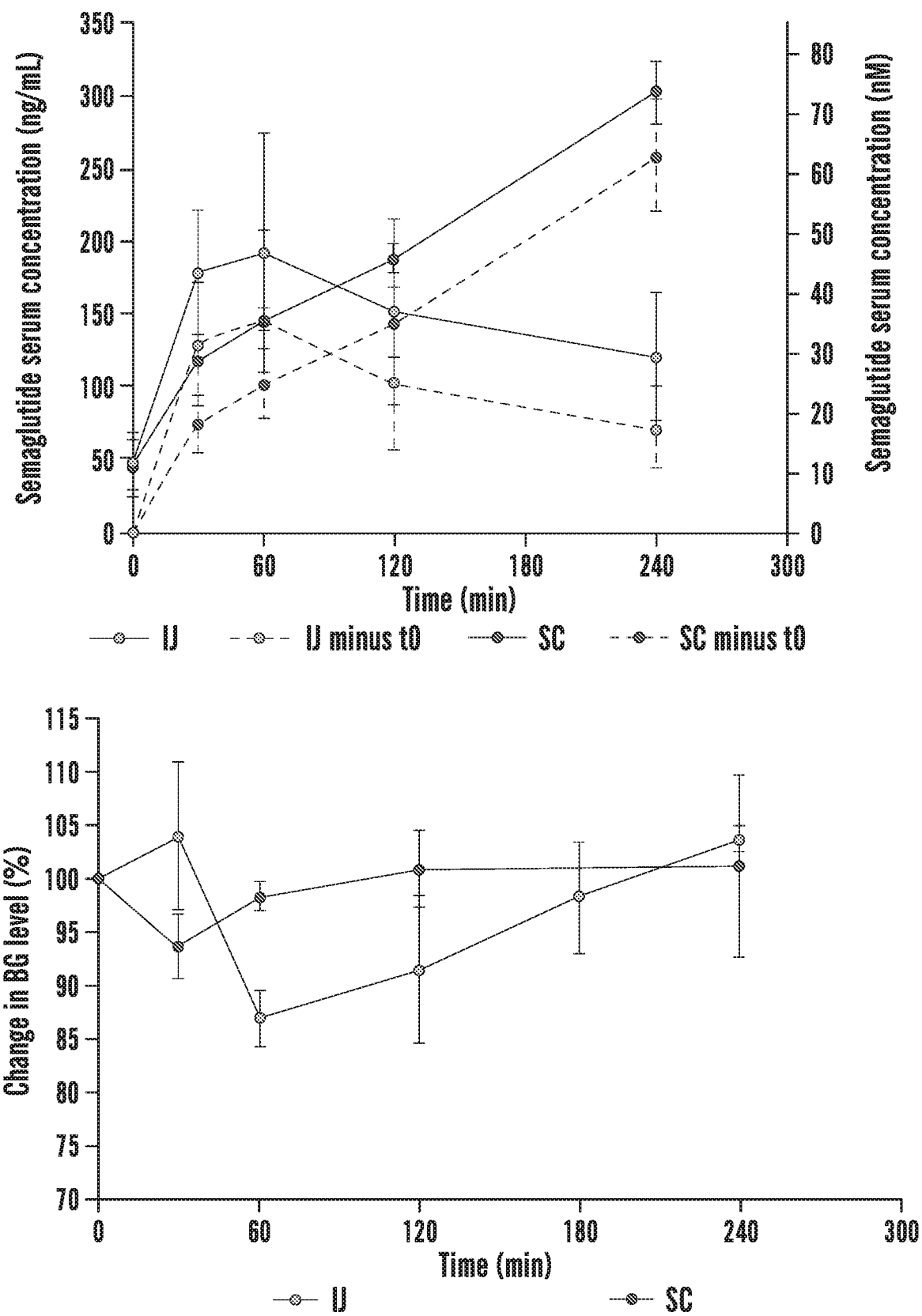
FIG. 32 depicts graphs of the PK and PD of semaglutide administered in CAGE. n=3, mean+/−SEM. T0 timepoints were positive for semaglutide via EIA kit, and these T0 values were subtracted in the dashed line data sets.

Semaglutide Study in Non-Diabetic Male Wistar Rats 0.12 mg/kg (30 nmol/kg) semaglutide in total volume of 250 uL was injected SC into conscious animals. After 4 hours, BG was measured. Serum was collected to measure the semaglutide concentration at 0, 30, 60, 120 and 240 minutes (FIG. 32).

1.2 mg/kg (10×SC dose) semaglutide in 100 uL total volume of CAGE was injected intrajejunally via abdominal surgery into animals under anesthesia for the duration of the experiment. After 4 hours, BG was measured. Serum was collected to measure the semaglutide concentration at 0, 30, 60, 120 and 240 minutes (FIG. 32).

Serum semaglutide concentrations (ng/mL) were determined via competitive EIA, and significant semaglutide was detected in the blood after intrajejunal administration with CAGE.

Example 8

Results

Figure 33:
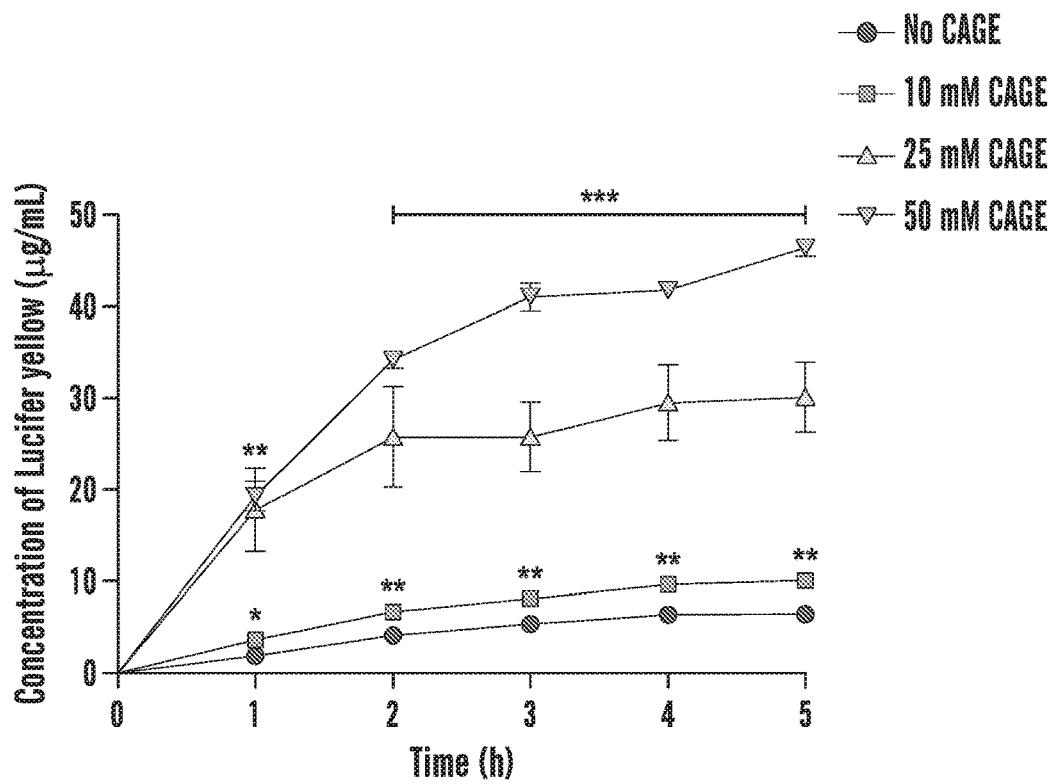
FIG. 33 depicts enhancement in Lucifer yellow transport across Caco-2 monolayers in the presence of different concentrations of CAGE. Data represented as mean±S.E. (n=4) (*p<0.05,  p<0.001, * p<0.0001; all CAGE treatments compared to no CAGE treatment).

Interactions of CAGE with Caco-2 monolayer were studied in vitro. The transport of *Lucifer* yellow exhibited a concentration-dependent enhancement with CAGE (FIG. 33).

Figure 34:
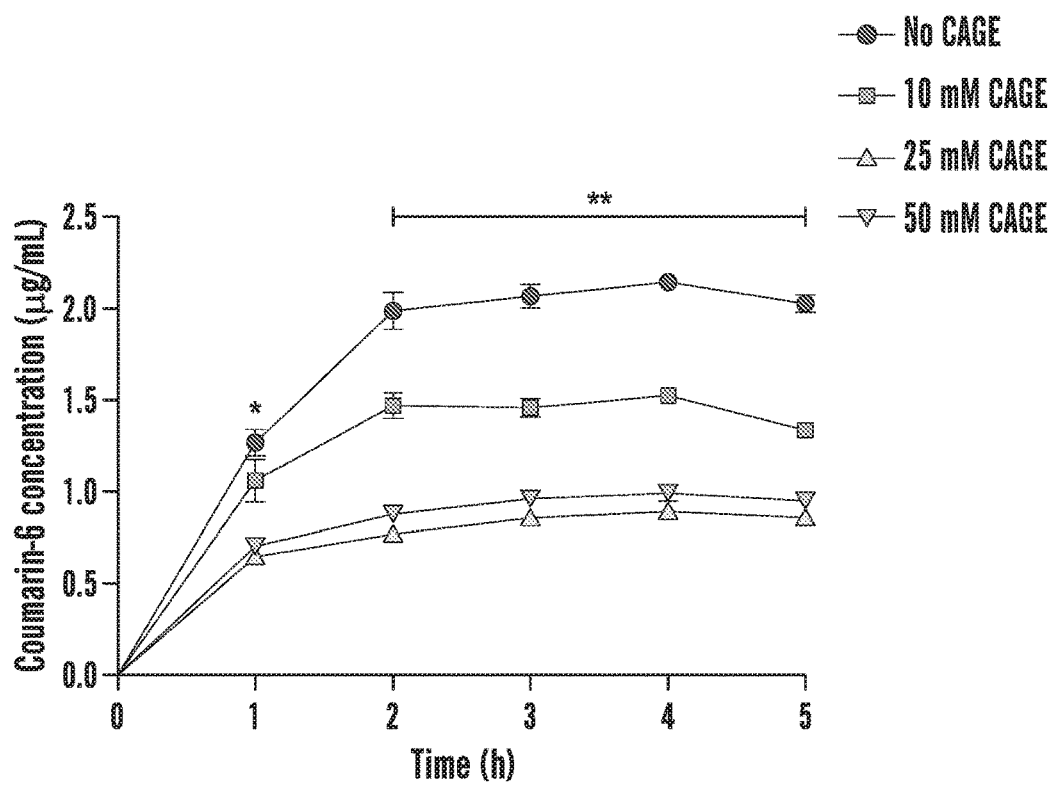
FIG. 34 depicts the effect of various concentration of CAGE on passive transcytosis of coumarin-6. Data represented as mean±S.E. (n=4); (* p<0.05; **p<0.0001; No CAGE treatment compared to 10 mM CAGE treatment group).

The transcellular permeability of coumarin-6 (a fluorescent marker for passive transcytosis) in the presence of CAGE was thereafter assessed. Surprisingly, CAGE reduced the transcellular uptake of coumarin-6 even at low concentrations (FIG. 34).

Results

CAGE Mediated Drug Transport Across Intestinal Cells is Primarily Paracellular.

Transport of molecules across intestinal epithelia can be either paracellular or transcellular. To evaluate the mechanism by which CAGE enhances transport of drugs across Caco-2 monolayers, both paracellular and passive transcellular transport was investigated in the presence of varying concentrations of CAGE using specific markers for their transport. To this end, the transport of Lucifer yellow was assessed. Lucifer yellow transport was enhanced significantly across all time points in the presence of 10-50 mM CAGE (FIG. 33). At the lowest 10 mM CAGE concentration, transport was enhanced by ~2 fold.

Using 50 mM CAGE, the transport of Lucifer yellow was significantly enhanced compared to marker alone, by 7-10 fold at various time points. On the other hand, the transport of 4 kDa FITC-dextran with a size similar to that of insulin was also significantly enhanced by 2-6 and 6-13 fold in the presence of 25 and 50 mM CAGE respectively (FIG. 33) at various time points.

After having explored the paracellular route, the transcellular transport of molecules across the intestinal cells in the presence of CAGE was evaluated using coumarin-6 (a fluorescent marker for passive transcellular transport). In the presence of 10-50 mM CAGE, coumarin-6 transcytosis was significantly decreased at all time points, indicating that CAGE does not primarily assist passive transcytosis of drugs (FIG. 34). This mitigated transcytosis of coumarin-6 in the presence of CAGE, points toward decreased cell membrane perturbation, if any, and thus superior biocompatibility of CAGE with intestinal cells.

Methods

Caco-2 Monolayer Culture in 96-Well Plate and Transwells.

For transport experiments in transwells, a 3-day rapid Caco-2 growth system was used. Cells were placed in Corning® basal seeding medium (BSM) supplemented with MITO serum+ extender and seeded at density of 400,000 cells/mL on Millicell® PCF inserts placed inside 24-well plates. 500 μL of cells containing medium was placed in apical side while 1000 μL of cell free BSM was put in the basolateral side as per manufacturer recommendation. After 24 h of incubation at 37° C., 5% CO2, the medium was replaced with same volume of enterocyte differentiation medium supplemented with MITO serum+ extender for another 2-4 days.

Lucifer Yellow and Coumarin-6 Transport Assay In Vitro.

Before the start of the experiment, the medium in the transwells was replaced with DMEM devoid of phenol red, FBS and P/S in both the apical (200 μL) and basolateral side (600 μL) and the cells were incubated for 30 minutes. Thereafter, the medium in the apical side was replaced with 200 μL of 500 μg/mL of Lucifer yellow (LY) or 5 μg/mL of coumarin-6 in DMSO (10% final concentration), prepared with or without 10, 25 and 50 mM CAGE and solubilized in DMEM free of phenol red, FBS and P/S. Immediately after addition of the test article to the apical side, a 100 μL aliquot was withdrawn from the basolateral side and replaced with an equal volume of fresh DMEM. This was repeated at 1, 2, 3, 4 and 5 h. During the study, the transwell plates were placed inside an incubator at 37° C., 5% CO2 on a shaker rotating at 100 rpm and only taken out to remove aliquots at each time point. After the end of study at 5 h, fluorescence in the aliquots with LY and coumarin-6 concentrations were measured using a plate reader (BioTek Synergy NEO HTS™ microplate reader (Winooski, Vt., USA) at 485/530, 495/520 and 468/568 nm excitation/emission wavelengths, respectively. Calibration solutions for each test article were prepared and analyzed using fluorescence readings for LY and coumarin-6 which was used to plot of basolateral chamber concentration vs time plots.

Materials.

Geranic acid, choline bicarbonate, dimethyl sulfoxide (DMSO), FITC-insulin, FITC-dextran, sodium caprate (98% purity), mucin, coumarin-6 and human insulin were purchased from Sigma-Aldrich (St. Louis, Mo., USA), while bovine trypsin was obtained from MP Biomedicals (Santa Ana, Calif., USA). Caco-2 human colorectal adenocarcinoma cells were bought from American Type Culture Collection (Manassas, Va., USA) while Dulbecco modified eagle medium (DMEM) with or without phenol red, fetal bovine serum (FBS), penicillin/streptomycin (P/S) solution, Hank's balanced salt solution (HBSS), Dulbecco's phosphate buffered saline (DPBS) and 0.25% trypsin solution were purchased from Thermo Fisher Scientific (Waltham, Mass., USA). Intestinal epithelium growth medium comprising basal seeding medium (BSM), enterocyte differentiation medium (EDM) and MITO+ serum extender was purchased from Corning (Corning, N.Y., USA). Millicell®-PCF cell culture inserts (3.0 μm pore size, 12 mm diameter) and TEER measuring device, Millicell®-ERS were obtained from Millipore Sigma (Burlington, Mass., USA) while TEER measuring electrodes were obtained from World Precision Instruments, Inc (Sarasota, Fla., USA). Paraformaldehyde (16% w/v) and metoclopramide hydrochloride were purchased from Alfa Aesar (Ward Hill, Mass., USA) and Vectashield Hardset™ with 4',6-diamidino-2-phenylindole, dihydrochloride (DAPI) was obtained from Vector laboratories Inc. (Burlingame, Calif., USA). 3-(4,5-dimethylthiazol-2-yl)-2,5-diphenyltetrazolium bromide (MTT) cytotoxicity kit and human insulin ELISA kit were obtained from ThermoFisher Scientific (Waltham, Mass., USA). Male Wistar rats weighing between 200-300 g were purchased from Charles River Laboratories (Wilmington, Mass., USA) and blood glucose measuring meter (Aimstrip plus) along with its strips were purchased from Fisher Scientific (Pittsburgh, Pa., USA). Capsule oral gavage and size 9 elongated capsules were obtained from Torpac (Fairfield, Mass., USA). Hematoxylin and eosin solutions were purchased from Sigma Aldrich (St. Louis, Mo., USA). Lucifer yellow was purchased from VWR (Radnor, Pa., USA). All other reagents used were of analytical grade.

Preparation of CAGE and Insulin-CAGE.

CAGE was synthesized as per our previous study. Briefly, two equivalents of neat geranic acid (20 g, 0.119 mol) that had been recrystallized at least 5 times in acetone at <−70° C. to remove impurities, were added to one equivalent of choline bicarbonate (80 wt % solution, 12.275 g, 0.059 mol) in a 500 mL round-bottom flask. The mixture was stirred at 40° C. until $CO_2$ evolution ceased, and the water was removed by rotary evaporation at 60° C. for 2 h followed by drying in a vacuum oven for 48 h at 60° C. Physical characterization at 25° C. showed good agreement with previous values. The NMR spectra (collected using a 500-MHz Varian instrument, Palo Alto, Calif.) was also in good agreement with previous preparations: $^1$H NMR (DMSO-$d_6$), δ5.60 (s, 2H), 5.07 (t, J=6.1, 2H), 3.86 (t, J=6.6, 2H), 3.42 (t, J=6.6, 2H), 3.12 (s, 9H), 2.57 (m, 4H), 2.01 (m, 4H), 1.97 (s, 6H), 1.73 (s, 2H), 1.64 (s, 6H), and 1.57 (s, 6H); $^{13}$C NMR (DMSO-$d_6$), δ170.1, 150-1, 131.5, 124.1, 122, 67.6, 55.5, 53.6, 53.5, 32.8, 25.9, and 17.9. Insulin-CAGE was prepared by adding pre-determined amount of insulin powder to specific volume of CAGE, followed by vortexing for 5 min.

Data Analysis.

All data are presented as mean±standard error (S.E.). For statistical analysis, student's T-test was utilized. Significant difference was considered at $p<0.05$. All experiments were conducted in at least triplicates.

Example 9

Figure 35:
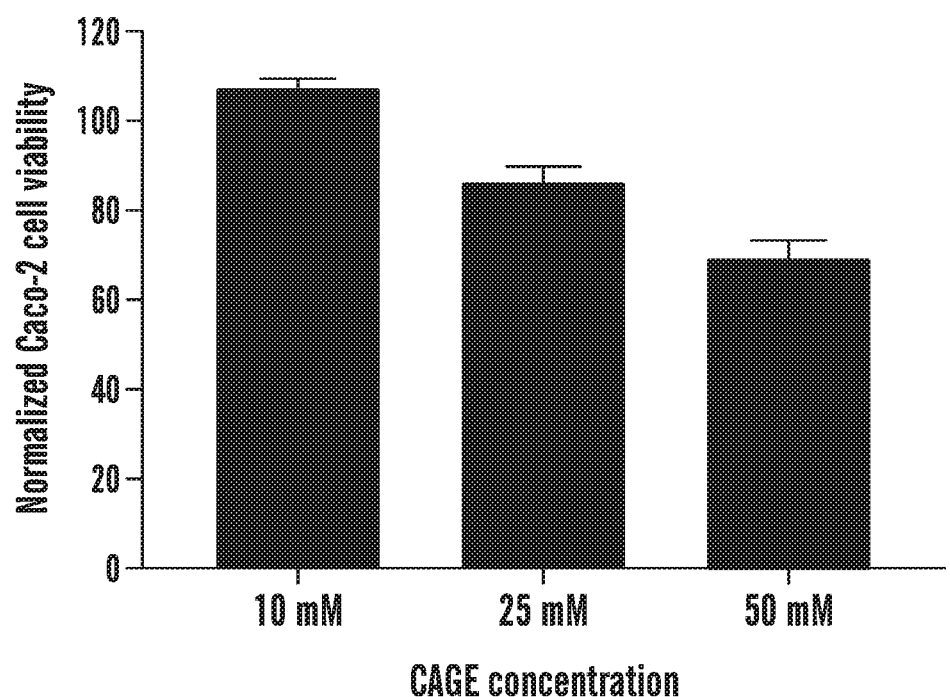
FIG. 35 depicts the viability of Caco-2 cells upon treatment with various concentrations of CAGE. CAGE was removed from culture media after 5 h and replaced with fresh DMEM. Cellular viability was measured after an additional 19 h (total 24 h) using MTT assay. Data represented as mean±S.E. (n=4).
Figure 36:
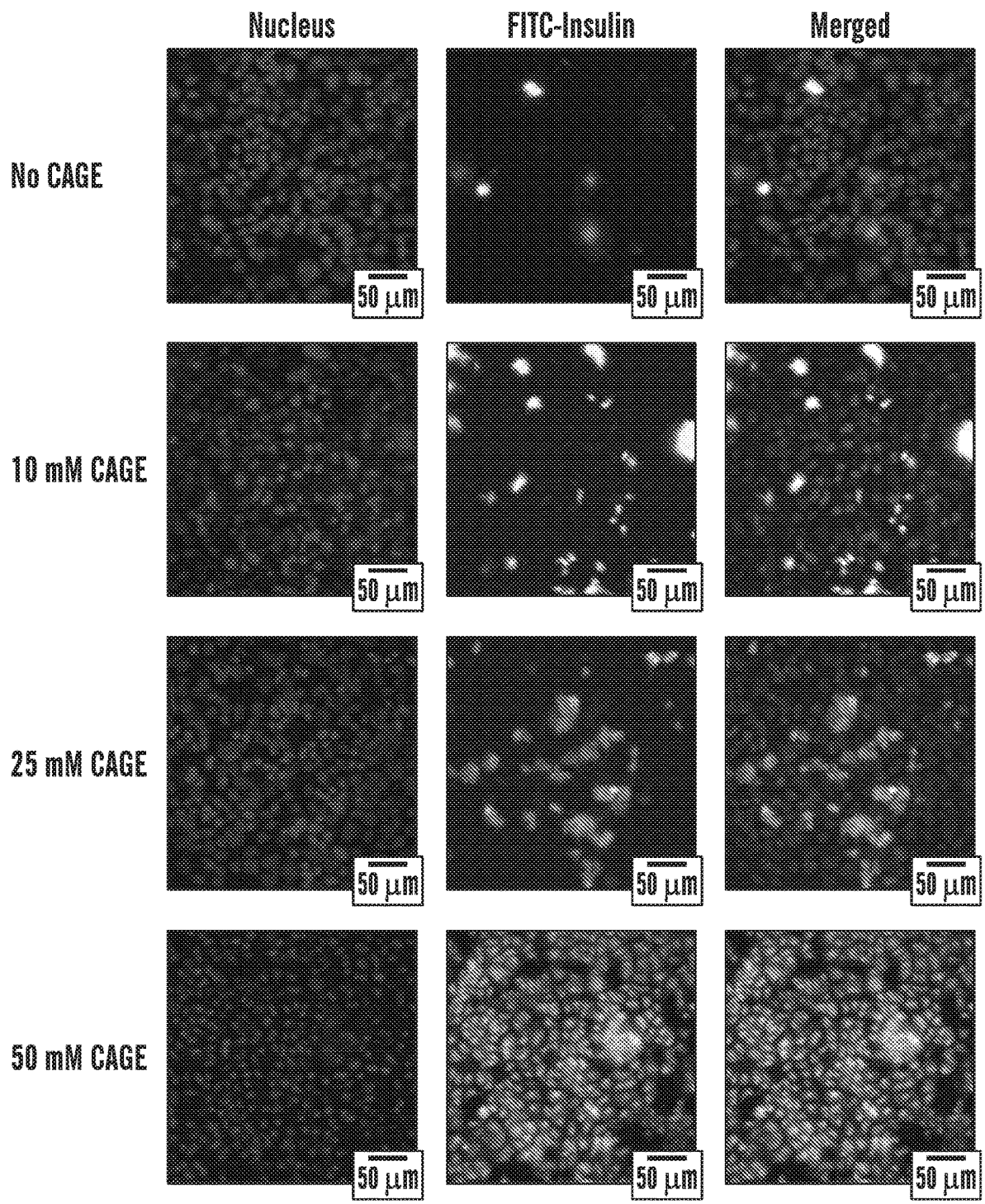
FIG. 36 depicts representative confocal micrograph images of transwell membranes covered with a layer of Caco-2 cells and incubated for 5 h with FITC-insulin dispersed in various concentrations of CAGE or PPS. Images were taken at 40× magnification. The images show DAPI labeled nuclei (blue color), FITC-insulin (green color) and an overlap of DAPI staining and FITC-insulin.
Figure 37:
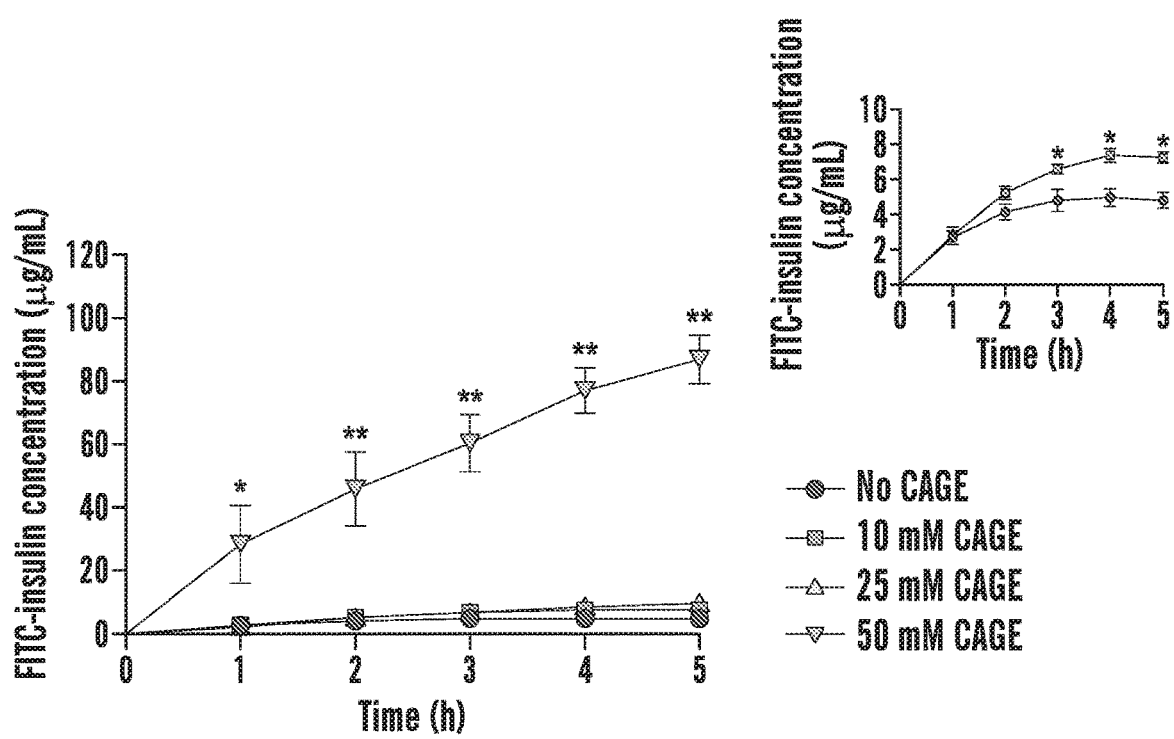
FIG. 37 demonstrates enhancement in FITC-insulin transport across Caco-2 monolayers in the presence of CAGE. Data represented as mean±S.E. (n=4) (* p<0.05, ** p<0.001; CAGE treatments compared to no CAGE treatment).
Figure 38:
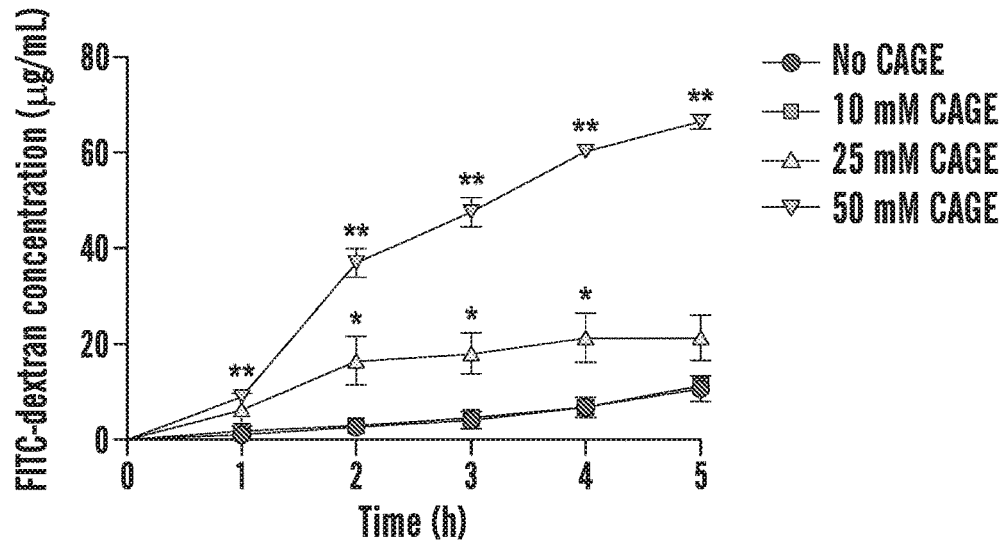
FIG. 38 depicts enhancement in FITC-dextran transport across Caco-2 monolayers in the presence of different concentrations of CAGE. Data represented as mean±S.E. (n=4) (*p<0.01, ** p<0.0001; CAGE treatments compared to no CAGE treatment).
Figure 39:
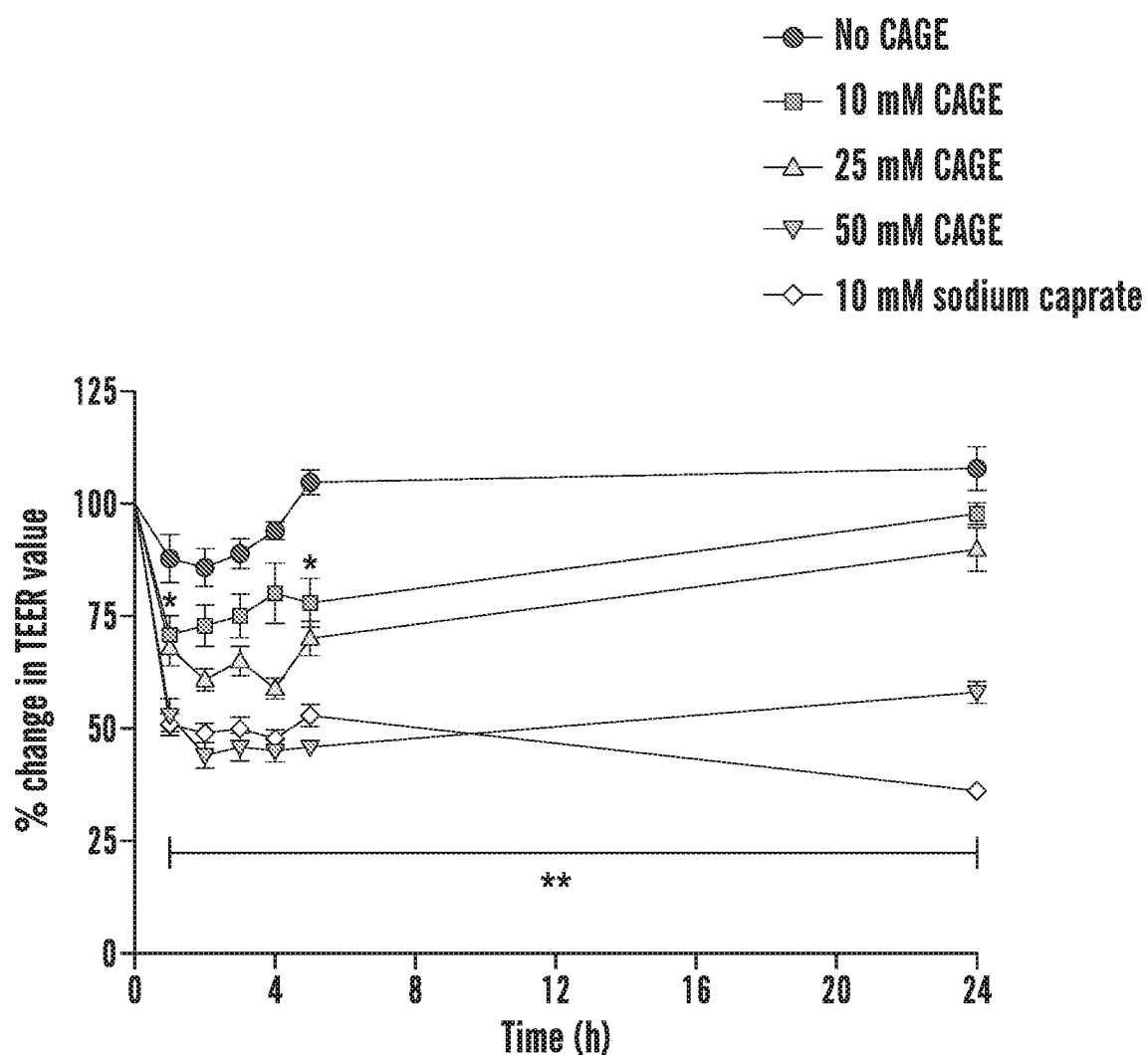
FIG. 39 depicts the effect on tight junction integrity in Caco-2 cells upon treatment with various concentrations of CAGE or 10 mM sodium caprate. Data represented as mean±S.E. (n=4); (* p<0.05; **p<0.0001; all CAGE treatments compared to no CAGE treatment).

CAGE exhibited concentration-dependent effect on Caco-2 cells (FIG. 35). CAGE also exhibited concentration-dependent enhancement of insulin transport, with the enhancement of >10-fold for 50 mM CAGE (FIGS. 36 and 36). The enhancement mechanism is likely mediated by the paracellular route. Furthermore, transport of 4 kDa FITC-dextran (comparable size as insulin) was also increased in a concentration-dependent manner, reaching an enhancement of 13-fold (FIG. 38). This was corroborated by measuring the intestinal tight junction integrity through determination of trans epithelial electrical resistance (TEER). As observed earlier, a concentration-dependent decrease in TEER was observed upon exposure to CAGE for 5 h, followed by concentration-dependent recovery (FIG. 39). Treatment of cells with 10 mM CAGE resulted in significant decrease in TEER at 1 and 5 h, while treatment with 25 and 50 mM CAGE led to a significant (40-50%) decrease in TEER at all time points and TEER recovery to 90 and 58% of initial levels within 24 h respectively. For reference, drop in TEER after exposure to a well-known permeation enhancer drug sodium caprate was also measured.

Materials and Methods

Materials.

Geranic acid, choline bicarbonate, dimethyl sulfoxide (DMSO), FITC-insulin, FITC-dextran, sodium caprate (98% purity), mucin, and human insulin were purchased from Sigma-Aldrich (St. Louis, Mo., USA), while bovine trypsin was obtained from MP Biomedicals (Santa Ana, Calif., USA). Caco-2 human colorectal adenocarcinoma cells were bought from American Type Culture Collection (Manassas, Va., USA) while Dulbecco modified eagle medium (DMEM) with or without phenol red, fetal bovine serum (FBS), penicillin/streptomycin (P/S) solution, Hank's balanced salt solution (HBSS), Dulbecco's phosphate buffered saline (DPBS) and 0.25% trypsin solution were purchased from Thermo Fisher Scientific (Waltham, Mass., USA). Intestinal epithelium growth medium comprising basal seeding medium (BSM), enterocyte differentiation medium (EDM) and MITO+ serum extender was purchased from Corning (Corning, N.Y., USA). Millicell®-PCF cell culture inserts (3.0 μm pore size, 12 mm diameter) and TEER measuring device, Millicell®-ERS were obtained from Millipore Sigma (Burlington, Mass., USA) while TEER measuring electrodes were obtained from World Precision Instruments, Inc (Sarasota, Fla., USA). Paraformaldehyde (16% w/v) and metoclopramide hydrochloride were purchased from Alfa Aesar (Ward Hill, Mass., USA) and Vectashield Hardset™ with 4',6-diamidino-2-phenylindole, dihydrochloride (DAPI) was obtained from Vector laboratories Inc. (Burlingame, Calif., USA). 3-(4,5-dimethylthiazol-2-yl)-2,5-diphenyltetrazolium bromide (MTT) cytotoxicity kit and human insulin ELISA kit were obtained from ThermoFisher Scientific (Waltham, Mass., USA). Male Wistar rats weighing between 200-300 g were purchased from Charles River Laboratories (Wilmington, Mass., USA) and blood glucose measuring meter (Aimstrip plus) along with its strips were purchased from Fisher Scientific (Pittsburgh, Pa., USA). Capsule oral gavage and size 9 elongated capsules were obtained from Torpac (Fairfield, Mass., USA). Hematoxylin and eosin solutions were purchased from Sigma Aldrich (St. Louis, Mo., USA). All other reagents used were of analytical grade.

Preparation of CAGE and Insulin-CAGE.

CAGE was synthesized as per our previous study (38). Briefly, two equivalents of neat geranic acid (20 g, 0.119 mol) that had been recrystallized at least 5 times in acetone at <−70° C. to remove impurities, were added to one equivalent of choline bicarbonate (80 wt % solution, 12.275 g, 0.059 mol) in a 500 mL round-bottom flask. The mixture was stirred at 40° C. until $CO_2$ evolution ceased, and the water was removed by rotary evaporation at 60° C. for 2 h followed by drying in a vacuum oven for 48 h at 60° C. Physical characterization at 25° C. showed good agreement with previous values. The NMR spectra (collected using a 500-MHz Varian instrument, Palo Alto, Calif.) was also in good agreement with previous preparations: $^1$H NMR (DMSO-$d_6$), δ5.60 (s, 2H), 5.07 (t, J=6.1, 2H), 3.86 (t, J=6.6, 2H), 3.42 (t, J=6.6, 2H), 3.12 (s, 9H), 2.57 (m, 4H), 2.01 (m, 4H), 1.97 (s, 6H), 1.73 (s, 2H), 1.64 (s, 6H), and 1.57 (s, 6H); $^{13}$C NMR (DMSO-$d_6$), δ170.1, 150-1, 131.5, 124.1, 122, 67.6, 55.5, 53.6, 53.5, 32.8, 25.9, and 17.9. Insulin-CAGE was prepared by adding pre-determined amount of insulin powder to specific volume of CAGE, followed by vortexing for 5 min.

CAGE Significantly Enhanced Transport of Insulin Across Intestinal Monolayers.

A 5 h-long transport experiment of fluorescein isothiocyanate (FITC)-insulin across Caco-2 monolayers was developed using 0, 10, 25 and 50 mM CAGE. FITC-insulin transport steadily increased with time in both groups throughout the study but 50 mM insulin-CAGE treated cells demonstrated very significantly higher transport from the onset compared to no CAGE control cells (FIG. 36). >10-fold higher insulin transport was observed across all time points in monolayers treated with 50 mM CAGE compared to untreated cells. Meanwhile, 10 and 25 mM CAGE enhanced FITC-insulin transport by 1.5-2 fold.

These results were corroborated through confocal images of transwell membranes at the end of the study at 5 h. The images clearly show higher uptake of FITC-insulin by Caco-2 cells with increasing concentration of CAGE compared to control cells (FIG. 36).

CAGE Mediated Drug Transport Across Intestinal Cells is Primarily Paracellular.

Transport of molecules across intestinal epithelia can be either paracellular or transcellular. To evaluate the mechanism by which CAGE enhances transport of drugs across Caco-2 monolayers, both paracellular and passive transcellular transport was investigated in the presence of varying concentrations of CAGE using specific markers for their transport. To this end, the transport of 4 kDa FITC-dextran (specific markers for paracellular transport) was assessed.

The transport of 4 kDa FITC-dextran with a size similar to that of insulin was also significantly enhanced by 2-6 and 6-13 fold in the presence of 25 and 50 mM CAGE respectively (FIG. 38) at various time points. However, to confirm whether CAGE improved paracellular transport of molecules, the tight junction integrity of Caco-2 cells treated with varying concentrations of CAGE was assessed by measuring trans epithelial electrical resistance (TEER) and comparing it with an established permeation enhancer, sodium caprate (FIG. 39) In control cells, TEER dropped slightly by ~10% in the first 3 h after which it recovered to its initial value by 5 h and did not change till end of study at 24 h. However, upon treatment with 10 mM CAGE, TEER dropped by 29% in 1 h and was significantly different from control at 1 and 5 h. This TEER drop was found to be transient and the cells completely recovered their tight junction integrity within 24 h.

Tight junction integrity also significantly decreased upon incubation with 25 mM (~40% drop) and 50 mM CAGE (~50% drop). However, a good recovery of about 90% of initial levels was observed with 25 mM CAGE. At 50 mM CAGE, TEER slightly recovered to 58% of initial level in 24 h. On the other hand, while TEER drop due to sodium caprate was similar to that of 50 mM CAGE, the tight junction integrity in this group further decreased to 36% of initial levels by the end of study at 24 h. The changes in TEER brought about by 10-25 mM CAGE suggest that at these concentrations, CAGE temporarily opens up the intestinal tight junctions that aid insulin transport across the cells. Other oral absorption enhancement mechanisms mediated by CAGE such as mucus penetration and stability against enzymatic degradation were also subsequently evaluated.

Caco-2 Monolayer Culture in 96-Well Plate and Transwells.

For transport experiments in transwells, a 3-day rapid Caco-2 growth system was used. Cells were placed in Corning® basal seeding medium (BSM) supplemented with MITO serum+ extender and seeded at density of 400,000 cells/mL on Millicell® PCF inserts placed inside 24-well plates. 500 μL of cells containing medium was placed in apical side while 1000 μL of cell free BSM was put in the basolateral side as per manufacturer recommendation. After 24 h of incubation at 37° C., 5% CO2, the medium was replaced with same volume of enterocyte differentiation medium supplemented with MITO serum+ extender for another 2-4 days. TEER was measured on a regular basis and when it reached above 200 ohms. cm2, indicating sufficient tight junction integrity between cells, transport study was performed.

Insulin Transport Assay In Vitro.

Before the start of the experiment, the existing medium in the transwell was replaced with DMEM devoid of phenol red, fetal bovine serum (FBS) and penicillin/streptomycin (P/S) in both the apical (200 μL) and basolateral side (600 μL) and the cells were incubated for 30 minutes. Thereafter, the medium in the apical side was replaced with 200 μL of 500 μg/mL FITC-insulin prepared with or without 10, 25 or 50 mM CAGE and solubilized in DMEM free of phenol red, FBS and P/S. Immediately after addition of FITC-insulin at the apical side, a 100 μL aliquot was withdrawn from the basolateral side and replaced with equal volume fresh DMEM. This was repeated at 1, 2, 3, 4 and 5 h. During the study, the transwell plates were placed inside an incubator at 37° C., 5% CO2 on a shaker rotating at 100 rpm and only taken out to remove aliquots at the aforementioned time periods. After the end of study at 5 h, the FITC-insulin concentration in the aliquots were measured using a plate reader (Tecan, Infinite M1000, Mannedorf, Switzerland) at 495/520 nm excitation/emission wavelengths and plotted as % FITC-insulin transport vs time. Furthermore, TEER was measured at every time point when aliquots were withdrawn from the transwells and plotted as basolateral chamber concentration vs time.

For qualitative analysis of FITC-insulin uptake by Caco-2 cells, the transwells from FITC-insulin transport study were washed two times with HBSS at the end of study, followed by addition of 100 µL of 4% paraformaldehyde and kept at 4° C. overnight. On the next day, paraformaldehyde was aspirated from the wells, membranes washed with PBS two times and the transwell membrane were cut and gently placed on glass slides. Mounting media containing (4',6-Diamidino-2-Phenylindole, Dihydrochloride) DAPI was added to the membranes and covered with cover slips. Confocal imaging of the membranes was taken using Olympus Fluoview™ 1000 Spectral Confocal instrument at 40× magnification.

FITC-Dextran Transport Assay In Vitro.

Before the start of the experiment, the medium in the transwells was replaced with DMEM devoid of phenol red, FBS and P/S in both the apical (200 µL) and basolateral side (600 µL) and the cells were incubated for 30 minutes. Thereafter, the medium in the apical side was replaced with 200 µL of 500 µg/mL of 4 kDa FITC-dextran in DMSO (10% final concentration), prepared with or without 10, 25 and 50 mM CAGE and solubilized in DMEM free of phenol red, FBS and P/S. Immediately after addition of the test article to the apical side, a 100 µL aliquot was withdrawn from the basolateral side and replaced with an equal volume of fresh DMEM. This was repeated at 1, 2, 3, 4 and 5 h. During the study, the transwell plates were placed inside an incubator at 37° C., 5% CO2 on a shaker rotating at 100 rpm and only taken out to remove aliquots at each time point. After the end of study at 5 h, fluorescence in the aliquots with FTIC-dextran concentrations were measured using a plate reader (BioTek Synergy NEO HTS™ microplate reader (Winooski, Vt., USA) at 485/530, 495/520 and 468/568 nm excitation/emission wavelengths, respectively. Calibration solutions for each test article were prepared and analyzed using fluorescence readings for FITC-dextran which was used to plot of basolateral chamber concentration vs time plots.

Effect of CAGE and Sodium Caprate on TEER Values.

Before the start of the experiment, the existing medium in the transwell was replaced with DMEM devoid of phenol red, FBS and P/S in both the apical (200 µL) and basolateral side (600 µL) and the cells were incubated for at least 30 minutes. TEER values were recorded for each insert. Thereafter, the medium in the apical side was replaced with 200 µL of either 10, 25 and 50 mM CAGE or 10 mM sodium caprate. During the study, the transwell plates were placed inside an incubator at 37° C., 5% CO2 on a shaker rotating at 100 rpm and only taken out to perform additional TEER measurements at 1, 2, 3, 4, 5 and 24 h. TEER was plotted as % change from initial value vs time.

Example 10

Figure 40:
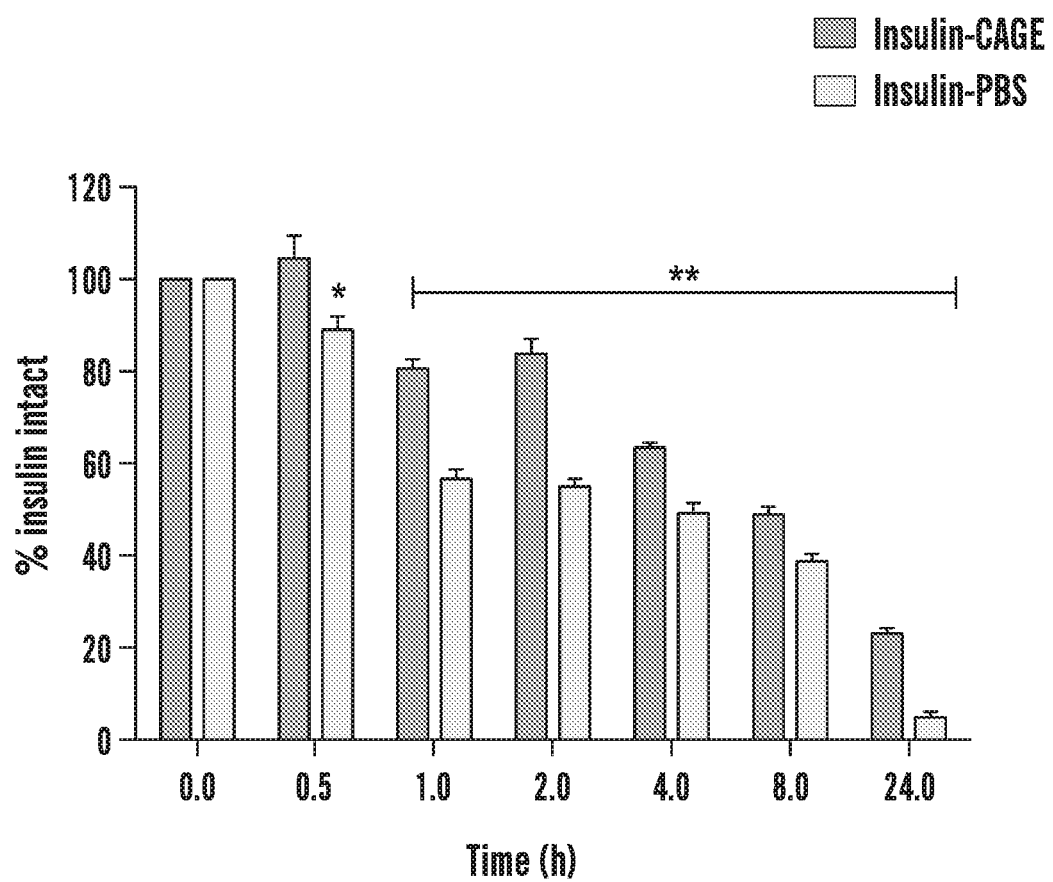
FIG. 40 depicts enhancement in stability of insulin by CAGE against tryptic digestion. Data represented as mean±S.E. (n=3); (* p<0.01; **p<0.001; Insulin-PBS treatment compared to Insulin-CAGE treatment).

CAGE significantly hindered tryptic digestion of insulin compared to buffer control (FIG. 40). This was particularly noted from 1 h onwards till the end of study at 24 h. The protection against enzymatic degradation in the earlier time period is critical to allow maximum oral absorption of intact insulin.

CAGE prevents enzymatic degradation, likely by limiting the access of intestinal enzymes to loaded insulin by forming a physical barrier and tempering their proteolytic activity. Enzyme activity is also modulated by its surrounding environment and molecular dynamics simulation studies have shown that ILs can remove water from the surface of enzymes to the same extent as polar organic solvents like acetonitrile. Based on this information and our mechanistic studies, it is contemplated herein that CAGE protects the insulin from enzymatic degradation.

Enzymatic Degradation of Insulin was Significantly Attenuated by CAGE.

It was postulated that an improved insulin pharmacokinetics/pharmacodynamics observed with CAGE in vivo could be due to improved stability of insulin in CAGE in the proteolytic milieu of the intestine. For this purpose, insulin in CAGE or insulin in buffer were incubated with trypsin for 24 h and the percentage of intact insulin remaining in the solution was determined at various time points. Results indicate that CAGE very significantly ($p<0.001$) prevented proteolytic degradation of insulin from 1 h onwards compared to the buffer control (FIG. 40). A 29% difference in the insulin degradation was obtained after 2 h of incubation with CAGE. At the end of the study at 24 h, while insulin in the buffer control was almost completely degraded (only 5±0.4% intact), about a quarter of insulin in CAGE still remained intact (24±0.2%). The study clearly illustrated that CAGE provides significant stability to insulin against proteolytic degradation which may play a role in improving the half-life of the drug both at the intestinal site as well as in the systemic circulation after oral uptake.

Materials and Methods

Materials.

Geranic acid, choline bicarbonate, dimethyl sulfoxide (DMSO), FITC-insulin, FITC-dextran, sodium caprate (98% purity), mucin, and human insulin were purchased from Sigma-Aldrich (St. Louis, Mo., USA), while bovine trypsin was obtained from MP Biomedicals (Santa Ana, Calif., USA). Caco-2 human colorectal adenocarcinoma cells were bought from American Type Culture Collection (Manassas, Va., USA) while Dulbecco modified eagle medium (DMEM) with or without phenol red, fetal bovine serum (FBS), penicillin/streptomycin (P/S) solution, Hank's balanced salt solution (HBSS), Dulbecco's phosphate buffered saline (DPBS) and 0.25% trypsin solution were purchased from Thermo Fisher Scientific (Waltham, Mass., USA). Intestinal epithelium growth medium comprising basal seeding medium (BSM), enterocyte differentiation medium (EDM) and MITO+ serum extender was purchased from Corning (Corning, N.Y., USA). Millicell®-PCF cell culture inserts (3.0 µm pore size, 12 mm diameter) and TEER measuring device, Millicell®-ERS were obtained from Millipore Sigma (Burlington, Mass., USA) while TEER measuring electrodes were obtained from World Precision Instruments, Inc (Sarasota, Fla., USA). Paraformaldehyde (16% w/v) and metoclopramide hydrochloride were purchased from Alfa Aesar (Ward Hill, Mass., USA) and Vectashield Hardset™ with 4',6-diamidino-2-phenylindole, dihydrochloride (DAPI) was obtained from Vector laboratories Inc. (Burlingame, Calif., USA). 3-(4,5-dimethylthiazol-2-yl)-2,5-diphenyltetrazolium bromide (MTT) cytotoxicity kit and human insulin ELISA kit were obtained from ThermoFisher Scientific (Waltham, Mass., USA). Male Wistar rats weighing between 200-300 g were purchased from Charles River Laboratories (Wilmington, Mass., USA) and blood glucose measuring meter (Aimstrip plus) along with its strips were purchased from Fisher Scientific (Pittsburgh, Pa., USA). Capsule oral gavage and size 9 elongated capsules were obtained from Torpac (Fairfield, Mass., USA). Hematoxylin and eosin solutions were purchased from Sigma Aldrich (St. Louis, Mo., USA). All other reagents used were of analytical grade.

Preparation of CAGE and Insulin-CAGE.

CAGE was synthesized as per our previous study (38). Briefly, two equivalents of neat geranic acid (20 g, 0.119 mol) that had been recrystallized at least 5 times in acetone at <−70° C. to remove impurities, were added to one equivalent of choline bicarbonate (80 wt % solution, 12.275 g, 0.059 mol) in a 500 mL round-bottom flask. The mixture was stirred at 40° C. until $CO_2$ evolution ceased, and the water was removed by rotary evaporation at 60° C. for 2 h followed by drying in a vacuum oven for 48 h at 60° C. Physical characterization at 25° C. showed good agreement with previous values. The NMR spectra (collected using a 500-MHz Varian instrument, Palo Alto, Calif.) was also in good agreement with previous preparations: $^1$H NMR (DMSO-$d_6$), δ5.60 (s, 2H), 5.07 (t, J=6.1, 2H), 3.86 (t, J=6.6, 2H), 3.42 (t, J=6.6, 2H), 3.12 (s, 9H), 2.57 (m, 4H), 2.01 (m, 4H), 1.97 (s, 6H), 1.73 (s, 2H), 1.64 (s, 6H), and 1.57 (s, 6H); $^{13}$C NMR (DMSO-$d_6$), δ170.1, 150-1, 131.5, 124.1, 122, 67.6, 55.5, 53.6, 53.5, 32.8, 25.9, and 17.9. Insulin-CAGE was prepared by adding pre-determined amount of insulin powder to specific volume of CAGE, followed by vortexing for 5 min.

Data Analysis.

All data are presented as mean±standard error (S.E.). For statistical analysis, student's T-test was utilized. Significant difference was considered at p<0.05. All experiments were conducted in at least triplicates.

Effect of CAGE on the Degradation of Insulin.

The effect of CAGE on trypsin-mediated degradation of insulin was studied at 37° C. in a solution containing equimolar concentrations of human insulin and bovine trypsin. In brief, 2 mL of neat CAGE or Dulbecco's phosphate buffered saline (DPBS) solution of insulin (86 μM) was added to a 3 mL of DPBS solution of trypsin (57 μM), vortexed, and incubated at 37° C. Immediately after vortex (time=0 h; t0) and at predetermined time intervals, 0.1 mL of the insulin-trypsin mixture was aliquoted, and the enzyme activity was inhibited by the addition of 0.1 mL of ice-cold 0.1% trifluoroacetic acid/acetonitrile solution (69:31, v/v). The samples were analyzed by liquid chromatography-mass spectrometry (LC-MS) to determine the amount of intact insulin in the solution at different times. An Agilent 1290/6140 Ultra High Performance Liquid Chromatography/Mass Spectrometer consisting of a 1290 Infinity LC™ binary pump, thermostat column compartment, 1290 Infinity autosampler, an Agilent 1290 diode array detector and an Agilent 6140 quadrupole MSD system was used for the analyses. For an analysis, 3 μL of the samples were injected into an Agilent 300SB-C18 2.1×75 mm, 5 μm, maintained at 25° C. and eluted with a mobile phase consisting of a gradient mixture of deionized water with 0.1% formic acid (FA) (A) and acetonitrile (B) with 0.1% FA. A gradient of 95-5% (0 min), 0-100% (10 min), 0-100% (15 min), 95-5% (15.1 min), 95-5% (18 min) A:B was used for each run. The mass spectrometer was set to collect in the selected ion monitoring mode for the (M+5H)+5 and (M+6H)+6 ions and the peak areas extracted to quantify the remaining insulin in the sample. The percentage of remaining insulin at each time interval relative to that at t0 was calculated. All experiments were conducted in triplicate and are reported are mean±standard deviation.

What is claimed herein is:

1. A composition comprising Choline And GEranate or Geranic Acid (CAGE) in combination with a further active compound;

wherein the composition is formulated as an oral formulation; and wherein the composition is encapsulated in an enterically coated capsule.

2. The composition of claim 1, wherein CAGE is at a concentration of at least 5% w/w.

3. The composition of claim 1, wherein the CAGE comprises a ratio of cation to anion of from about 2:1 to about 1:10.

4. The composition of claim 1, wherein CAGE is at a concentration of at least 0.1% w/v.

5. The composition of claim 1, wherein the active compound comprises a nucleic acid molecule; a small molecule; a polypeptide; an antibody; an antibody reagent; or a chemotherapeutic compound.

6. The composition of claim 5, wherein the active compound comprises a GLP-1 polypeptide or mimetic or analog thereof.

7. The composition of claim 5, wherein the active compound comprises insulin.

8. The composition of claim 1, further comprising a further pharmaceutically acceptable carrier.

9. The composition of claim 1, wherein the combination of the active compound and CAGE is an admixture.

10. The composition of claim 1, wherein the combination of the active compound and CAGE comprises nanoparticles comprising the active compound, the nanoparticles in solution or suspension in a composition comprising CAGE.

11. A method of delivery of at least one active compound, the method comprising orally administering the composition of claim 1.

\* \* \* \* \*

SEQUENCE LISTING

<160> NUMBER OF SEQ ID NOS: 4

<210> SEQ ID NO 1
<211> LENGTH: 180
<212> TYPE: PRT
<213> ORGANISM: Homo sapiens

<400> SEQUENCE: 1

Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

```
Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 2
<211> LENGTH: 37
<212> TYPE: PRT
<213> ORGANISM: Homo sapiens

<400> SEQUENCE: 2

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 3
<211> LENGTH: 30
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```